(12) United States Patent
Nasir et al.

(10) Patent No.: US 9,265,905 B2
(45) Date of Patent: Feb. 23, 2016

(54) STOPPER DEVICE

(75) Inventors: Muhammed Aslam Nasir, Bedfordhsire (GB); Surinderjit Jassell, Berkshire (GB)

(73) Assignee: ASHKAL DEVELOPMENTS LIMITED (IM)

( * ) Notice: Subject to any disclaimer, the term of this patent is extended or adjusted under 35 U.S.C. 154(b) by 418 days.

(21) Appl. No.: 13/805,956

(22) PCT Filed: Jun. 24, 2011

(86) PCT No.: PCT/GB2011/051203
§ 371 (c)(1),
(2), (4) Date: Dec. 20, 2012

(87) PCT Pub. No.: WO2011/161473
PCT Pub. Date: Dec. 29, 2011

(65) Prior Publication Data
US 2013/0092172 A1  Apr. 18, 2013

(30) Foreign Application Priority Data
Jun. 24, 2010  (GB) .................................. 1010647.4

(51) Int. Cl.
*A61M 16/00* (2006.01)
*A61M 16/04* (2006.01)

(52) U.S. Cl.
CPC ............ *A61M 16/04* (2013.01); *A61M 16/0409* (2014.02); *A61M 16/0431* (2014.02); *A61M 16/0434* (2013.01); *A61M 16/0463* (2013.01)

(58) Field of Classification Search
CPC ............ A61M 16/04; A61M 16/0402; A61M 16/0409; A61M 16/0415; A61M 16/0431; A61M 16/0486; A61M 16/0463; A61M 2207/00; B29L 2031/753
USPC ........................................ 128/207.15, 207.26
See application file for complete search history.

(56) References Cited

U.S. PATENT DOCUMENTS

| 478,582 | A | 7/1892 | Ermold | .................... 128/207.14 |
| 2,099,127 | A | 11/1937 | Leech | ....................... 128/207.15 |

(Continued)

FOREIGN PATENT DOCUMENTS

| AU | B-52036/90 | 9/1990 | ............ A61M 16/04 |
| AU | B-45803/93 | 2/1994 | ............ A61M 16/04 |

(Continued)

OTHER PUBLICATIONS

Office Action issued in related U.S. Appl. No. 29/428,284, dated Oct. 6, 2014 (66 pgs).

(Continued)

*Primary Examiner* — Jason Flick
*Assistant Examiner* — Victoria Leszczak
(74) *Attorney, Agent, or Firm* — Hayes Soloway P.C.

(57) ABSTRACT

An airway [(10, 310, 410, 510, 610, 710, 810, 1110, 1210, 1310, 1410, 1510, 1610, 710, 1810, 2010, 2110, 2210, 2310, 2410, 2510, 2610, 2710, 2810, 2910, 3010, 3110, 3210, 3310, 3810) device for human or animal use, the device includes an airway tube (12) having a first end (14) and a second end (16), wherein the device further includes a shoulder (26), the shoulder extends laterally from and substantially perpendicular to the airway tube, the shoulder is adapted to contact the faucial pillars of the human or animal patient to prevent over-insertion of the device in use.

38 Claims, 36 Drawing Sheets

(56) References Cited

U.S. PATENT DOCUMENTS

| | | | |
|---|---|---|---|
| 3,616,799 A | 11/1971 | Sparks | 128/351 |
| 3,734,100 A | 5/1973 | Walker et al. | 128/351 |
| 3,968,800 A | 7/1976 | Vilasi | 128/343 |
| 3,995,643 A | 12/1976 | Merav | 128/351 |
| 4,509,514 A | 4/1985 | Brain | 128/207.15 |
| 4,919,126 A | 4/1990 | Baildon | 128/207.14 |
| 4,995,388 A | 2/1991 | Brain | 128/207.15 |
| 5,054,483 A | 10/1991 | Marten et al. | 128/207.14 |
| 5,174,283 A | 12/1992 | Parker | 128/200.26 |
| 5,181,505 A | 1/1993 | Lew | 128/200.26 |
| 5,241,956 A | 9/1993 | Brain | 128/207.15 |
| 5,249,571 A | 10/1993 | Brain | 128/207.14 |
| 5,259,371 A | 11/1993 | Tonrey | 128/200.26 |
| 5,282,464 A | 2/1994 | Brain | 128/207.15 |
| 5,285,778 A | 2/1994 | Mackin | 128/207.15 |
| 5,297,547 A | 3/1994 | Brain | 128/207.15 |
| 5,303,697 A | 4/1994 | Brain | 128/200.26 |
| 5,305,743 A | 4/1994 | Brain | 128/207.15 |
| 5,322,062 A | 6/1994 | Servas | 128/207.14 |
| 5,339,805 A | 8/1994 | Parker | 128/200.26 |
| 5,355,879 A | 10/1994 | Brain | 128/207.15 |
| 5,360,697 A | 11/1994 | Mehra | 128/200.26 |
| 5,391,248 A | 2/1995 | Brain | 156/242 |
| 5,477,851 A | 12/1995 | Callaghan et al. | 128/207.15 |
| 5,584,290 A | 12/1996 | Brain | 128/207.15 |
| 5,623,921 A | 4/1997 | Kinsinger et al. | 128/200.26 |
| 5,632,271 A | 5/1997 | Brain | 128/207.15 |
| 5,655,519 A | 8/1997 | Alfery | 128/200.26 |
| 5,682,880 A | 11/1997 | Brain | 128/207.15 |
| 5,711,293 A | 1/1998 | Brain | 128/200.24 |
| 5,791,341 A | 8/1998 | Bullard | 128/207.15 |
| 5,853,004 A | 12/1998 | Goodman | 128/207.15 |
| 5,865,176 A | 2/1999 | O'Neil | 128/207.15 |
| 5,878,745 A | 3/1999 | Brain | 128/207.15 |
| 5,881,726 A | 3/1999 | Neame | 128/207.15 |
| 5,896,858 A | 4/1999 | Brain | 128/207.15 |
| 5,915,383 A | 6/1999 | Pagan | 128/207.15 |
| 5,921,988 A | 7/1999 | Legrand | 606/87 |
| 5,937,859 A | 8/1999 | Augustine et al. | 128/207.15 |
| 5,937,860 A | 8/1999 | Cook | 128/207.15 |
| 5,964,217 A | 10/1999 | Christopher | 128/200.26 |
| 5,976,072 A | 11/1999 | Greenberg | 600/120 |
| 5,979,445 A | 11/1999 | Neame et al. | 128/207.15 |
| 5,988,167 A | 11/1999 | Kamen | 128/207.15 |
| 6,003,514 A | 12/1999 | Pagan | 128/207.15 |
| 6,055,984 A | 5/2000 | Brain | 128/207.14 |
| 6,070,581 A | 6/2000 | Augustine et al. | 128/207.15 |
| 6,079,409 A | 6/2000 | Brain | 128/200.26 |
| D429,811 S | 8/2000 | Bermudez | D24/110.5 |
| 6,095,144 A | 8/2000 | Pagan | 128/207.15 |
| 6,152,136 A | 11/2000 | Pagan | 128/207.15 |
| 6,216,696 B1 | 4/2001 | van den Berg | 128/207.14 |
| 6,280,675 B1 | 8/2001 | Legrand | 264/262 |
| 6,311,688 B1 | 11/2001 | Augustine et al. | 128/200.26 |
| 6,318,367 B1 | 11/2001 | Mongeon | 128/207.15 |
| 6,422,239 B1 | 7/2002 | Cook | 128/207.15 |
| 6,439,232 B1 | 8/2002 | Brain | 128/207.15 |
| 6,474,332 B2 | 11/2002 | Arndt | 128/200.26 |
| 6,536,437 B1 | 3/2003 | Dragisic | 128/207.18 |
| 6,604,525 B2 | 8/2003 | Pagan | 128/207.15 |
| 6,631,720 B1 | 10/2003 | Brain | 128/207.14 |
| D482,118 S | 11/2003 | Dave et al. | D24/110 |
| 6,679,263 B2 | 1/2004 | Luchetti et al. | 128/207.15 |
| 6,698,430 B2 | 3/2004 | Van Landuyt | 128/207.15 |
| 6,705,318 B1 | 3/2004 | Brain | 128/207.14 |
| 6,705,321 B2 | 3/2004 | Cook | 128/207.15 |
| 6,705,322 B2 | 3/2004 | Chang | 128/207.15 |
| 6,792,948 B2 | 9/2004 | Brain | 128/207.14 |
| 6,799,574 B1 | 10/2004 | Collins | 128/207.15 |
| 6,877,512 B2 | 4/2005 | Imai et al. | 128/207.15 |
| 6,918,388 B2 | 7/2005 | Brain | 128/200.26 |
| 6,918,391 B1 | 7/2005 | Moore | 128/842 |
| 6,971,382 B1 | 12/2005 | Corso | 128/200.26 |
| 7,004,169 B2 | 2/2006 | Brain | 128/207.14 |
| D518,572 S | 4/2006 | Nasir | D24/110.5 |
| D518,890 S | 4/2006 | Nasir | D24/110.5 |
| 7,040,312 B2 | 5/2006 | Alfery et al. | 128/200.26 |
| 7,040,322 B2 | 5/2006 | Fortuna | 128/207.15 |
| 7,047,973 B2 | 5/2006 | Chang | 128/207.15 |
| 7,096,868 B2 | 8/2006 | Tateo et al. | 128/207.15 |
| 7,097,802 B2 | 8/2006 | Brain | 264/255 |
| 7,134,431 B2 | 11/2006 | Brain | 128/200.26 |
| 7,140,368 B1 | 11/2006 | Collins | 128/207.14 |
| D542,675 S | 5/2007 | Luxton et al. | D9/749 |
| 7,263,998 B2 | 9/2007 | Miller | 128/207.15 |
| RE39,938 E | 12/2007 | Brain | 128/207.15 |
| 7,305,985 B2 | 12/2007 | Brain | 128/200.26 |
| 7,357,845 B2 | 4/2008 | Cook | 156/242 |
| 7,506,648 B2 | 3/2009 | Brain | 128/207.15 |
| D611,138 S | 3/2010 | Nasir | D24/110.5 |
| D615,188 S | 5/2010 | Nasir | D24/110.5 |
| D618,788 S | 6/2010 | Dubach | D24/110.5 |
| 7,762,261 B1 | 7/2010 | Fortuna | 128/207.14 |
| 7,806,119 B2 | 10/2010 | Nasir | 128/205.25 |
| 7,896,007 B2 | 3/2011 | Brain | 128/207.15 |
| 7,900,632 B2 | 3/2011 | Cook | 128/207.14 |
| 8,001,964 B2 | 8/2011 | McDonald et al. | 128/200.26 |
| D650,520 S | 12/2011 | Timmermans | D27/163 |
| 8,091,242 B2 | 1/2012 | Teys et al. | 30/324 |
| 8,215,307 B2 | 7/2012 | Nasir | 128/207.15 |
| D665,495 S | 8/2012 | Nasir | D24/110.5 |
| D693,920 S | 11/2013 | Miller | D24/110.5 |
| 2001/0015207 A1 | 8/2001 | Pagan | 128/207.15 |
| 2001/0025641 A1 | 10/2001 | Doane et al. | 128/207.15 |
| 2002/0010417 A1 | 1/2002 | Bertram | 604/96.01 |
| 2002/0010617 A1 | 1/2002 | Hamaguchi et al. | 705/10 |
| 2002/0078961 A1 | 6/2002 | Collins | 128/207.15 |
| 2002/0108610 A1 | 8/2002 | Christopher | 128/200.26 |
| 2002/0112728 A1 | 8/2002 | Landuyt | 128/207.15 |
| 2002/0170556 A1 | 11/2002 | Gaitini | 128/200.14 |
| 2003/0037790 A1 | 2/2003 | Brain | 128/207.14 |
| 2003/0066532 A1 | 4/2003 | Gobel | 128/207.15 |
| 2003/0101998 A1 | 6/2003 | Zocca et al. | 128/207.15 |
| 2003/0136413 A1 | 7/2003 | Brain et al. | 128/207.15 |
| 2003/0172925 A1 | 9/2003 | Zocca et al. | 128/202.22 |
| 2003/0172933 A1 | 9/2003 | Nimmo | 128/207.14 |
| 2004/0020488 A1 | 2/2004 | Kniewasser | 128/204.18 |
| 2004/0020491 A1 | 2/2004 | Fortuna | 128/207.15 |
| 2005/0016529 A1 | 1/2005 | Cook | 128/200.24 |
| 2005/0051173 A1 | 3/2005 | Brain | 128/207.14 |
| 2005/0051175 A1 | 3/2005 | Brain | 128/207.14 |
| 2005/0066975 A1 | 3/2005 | Brain | 128/207.15 |
| 2005/0081861 A1 | 4/2005 | Nasir | 128/207.14 |
| 2005/0103345 A1 | 5/2005 | Brain | 128/207.15 |
| 2005/0104255 A1 | 5/2005 | Mejlhede et al. | 264/328.1 |
| 2005/0274383 A1 | 12/2005 | Brain | 128/207.15 |
| 2006/0081245 A1 | 4/2006 | Gould | 128/200.26 |
| 2006/0207601 A1 | 9/2006 | Nasir | 128/207.14 |
| 2008/0142017 A1 | 6/2008 | Brain | 128/207.15 |
| 2008/0308109 A1 | 12/2008 | Brain | 128/207.14 |
| 2010/0059061 A1 | 3/2010 | Brain | 128/207.14 |
| 2010/0089393 A1 | 4/2010 | Brain | 128/203.12 |
| 2010/0126512 A1 | 5/2010 | Nasir | 128/207.14 |
| 2010/0242957 A1 | 9/2010 | Fortuna | 128/202.22 |
| 2011/0277772 A1 | 11/2011 | Nasir | 128/207.15 |
| 2013/0092172 A1 | 4/2013 | Nasir | 128/207.15 |
| 2013/0247917 A1 | 9/2013 | Brain | 128/207.15 |
| 2015/0000672 A1 | 1/2015 | Jassell | 128/207.15 |

FOREIGN PATENT DOCUMENTS

| | | | |
|---|---|---|---|
| AU | 200076743 | 5/2001 | A61M 16/04 |
| CA | 1 324 551 | 11/1993 | A61M 16/04 |
| CA | 2 191 749 | 12/1995 | A61M 16/01 |
| CA | 2 346 248 | 4/2000 | A61M 16/04 |
| CN | 1 166 138 | 11/1997 | A61M 16/00 |
| CN | 1 236 326 | 11/1999 | A61M 16/04 |
| CN | 1 351 509 | 5/2002 | A61M 16/04 |
| DE | 42 33 933 | 4/1993 | H02N 2/00 |
| DE | 43 30 032 | 4/1994 | H02N 2/00 |
| DE | 195 00 550 | 7/1996 | A61M 16/04 |
| DE | 299 02 267 | 7/1999 | A61M 16/06 |
| DE | 201 00 176 | 5/2001 | A61M 16/01 |
| DE | 202 06 692 | 8/2002 | A61M 16/00 |

(56) References Cited

FOREIGN PATENT DOCUMENTS

| | | | |
|---|---|---|---|
| EM | 000067210-0001 | 8/2003 | |
| EM | 000067210-0002 | 8/2003 | |
| EM | 000197124-0001 | 6/2004 | |
| EM | 000197124-0002 | 6/2004 | |
| EM | 000197124-0003 | 6/2004 | |
| EM | 000197124-0004 | 6/2004 | |
| EM | 000197124-0005 | 6/2004 | |
| EM | 000180757-0001 | 7/2004 | |
| EM | 000482195-0001 | 2/2006 | |
| EM | 000482195-0002 | 2/2006 | |
| EM | 000482195-0006 | 2/2006 | |
| EP | 0 277 797 | 8/1988 | A61M 16/04 |
| EP | 0 387 272 | 9/1990 | A61M 16/04 |
| EP | 0 448 878 | 10/1991 | A61M 16/04 |
| EP | 0 586 717 | 3/1994 | A61M 16/04 |
| EP | 0 794 807 | 9/1997 | A61M 16/00 |
| EP | 0 834 331 | 8/1998 | A61M 16/04 |
| EP | 0 857 492 | 8/1998 | A61M 16/04 |
| EP | 0 875 260 | 11/1998 | A61M 16/04 |
| EP | 0 884 061 | 12/1998 | A61M 16/04 |
| EP | 0 911 049 | 4/1999 | A61M 16/04 |
| EP | 0 935 971 | 8/1999 | A61M 16/04 |
| EP | 1 125 595 | 8/2001 | A61M 16/04 |
| EP | 1504870 | 2/2005 | |
| EP | 1 579 885 | 9/2005 | A61M 16/04 |
| EP | 1 875 937 | 1/2008 | A61M 16/04 |
| ES | 1 046 206 | 1/2000 | A61M 25/00 |
| FR | 2 094 264 | 1/1972 | C07C 31/00 |
| FR | 2 690 018 | 10/1993 | H02N 2/00 |
| FR | 2 760 186 | 9/1998 | A61F 2/30 |
| FR | 2 807 307 | 10/2001 | A47J 37/06 |
| FR | 2 827 482 | 1/2003 | A24B 1/10 |
| FR | 2 851 107 | 8/2004 | H04M 11/06 |
| GB | 1 402 255 | 8/1975 | A61M 25/00 |
| GB | 2 113 348 | 8/1983 | B06B 1/16 |
| GB | 2 128 561 | 5/1984 | B60R 19/54 |
| GB | 2 168 256 | 6/1986 | A61M 16/04 |
| GB | 2 249 959 | 5/1992 | A61M 16/04 |
| GB | 2 267 034 | 11/1993 | A61M 25/02 |
| GB | 2 285 765 | 7/1995 | A61M 16/04 |
| GB | 2 317 342 | 3/1998 | A61M 16/04 |
| GB | 2 319 182 | 5/1998 | A61M 16/04 |
| GB | 2323292 | 9/1998 | A61M 16/04 |
| GB | 2 326 009 | 12/1998 | A61M 16/04 |
| GB | 2 330 312 | 4/1999 | A61M 16/04 |
| GB | 2 337 020 | 11/1999 | B29D 31/00 |
| GB | 2 359 996 | 9/2001 | A61M 16/04 |
| GB | 2 364 644 | 2/2002 | A61M 16/04 |
| GB | 2 373 188 | 9/2002 | A61M 16/04 |
| GB | 2 393 399 | 3/2004 | A61M 16/04 |
| GB | 2 404 863 | 2/2005 | A61M 16/04 |
| GB | 2 413 963 | 11/2005 | A61M 16/04 |
| GB | 2465453 | 5/2010 | A61M 16/04 |
| IE | 922073 | 12/1993 | A61M 16/00 |
| IT | 1224077 | 9/1990 | |
| JP | 3-236858 | 10/1991 | A61M 16/04 |
| JP | 6-277286 | 10/1994 | A61M 16/04 |
| JP | 2706567 | 1/1998 | A61B 1/00 |
| JP | 2007-509154 | 4/2007 | A61M 16/04 |
| TW | 224047 | 11/2004 | B29C 45/76 |
| WO | WO 94/17848 | 8/1994 | A61M 16/04 |
| WO | WO 95/09665 | 4/1995 | A61M 16/04 |
| WO | WO 97/12640 | 4/1997 | A61M 16/00 |
| WO | WO 98/06276 | 2/1998 | A23L 1/30 |
| WO | WO 98/24498 | 6/1998 | A61M 16/04 |
| WO | WO 98/50096 | 11/1998 | A61M 16/00 |
| WO | WO 99/24101 | 5/1999 | A61M 16/00 |
| WO | WO 99/44665 | 9/1999 | A61M 16/04 |
| WO | WO 00/09189 | 2/2000 | A61M 16/04 |
| WO | WO 00/30706 | 6/2000 | A61M 16/04 |
| WO | WO 00/61213 | 10/2000 | A61M 16/04 |
| WO | WO 01/13980 | 3/2001 | A61M 16/04 |
| WO | WO 0197890 | 12/2001 | A61M 16/00 |
| WO | WO 02/32490 | 4/2002 | A61M 16/04 |
| WO | WO 03/020340 | 3/2003 | A61M 16/04 |
| WO | WO 03018094 | 3/2003 | A61M 16/04 |
| WO | WO 2004/016308 | 2/2004 | A61M 16/04 |
| WO | WO2004/089453 | 10/2004 | |
| WO | WO 2005/016427 | 2/2005 | A61M 16/04 |
| WO | WO 2005/041864 | 5/2005 | |
| WO | WO 2010058219 A2 * | 5/2010 | |
| WO | WO2011161473 | 12/2011 | A61M 16/04 |

OTHER PUBLICATIONS

Office Action issued in related U.S. Appl. No. 12/627,844, dated Oct. 23, 2014 (38 pgs).
Office Action issued in related U.S. Appl. No. 29/475,489, dated Dec. 4, 2014 (13 pgs).
UK Search and Examination Report issued in corresponding application No. GB1110775.2, dated. Oct. 18, 2011 (8 pgs).
International Search Report and Written Opinion issued in corresponding application No. PCT/GB2011/051203, dated Jul. 12, 2011 (14 pgs).
US Official Action dated Feb. 14, 2013, issued in U.S. Appl. No. 29/407,461 (21 pgs).
International Search Report and Written Opinion issued in corresponding application No. PCT/GB2011/051203, dated Dec. 7, 2011 (15 pgs).
Combined Search and Examination Report issued in corresponding application No. GB1110775.2, dated Oct. 18, 2011 (8 pgs).
Combined Search and Examination Report issued in corresponding application No. GB0718849.3, dated Oct. 29, 2007 (4 pgs).
Combined Search and Examination Report issued in corresponding application No. GB0502519.2, dated Sep. 13, 2005 (6 pgs).
Extended European Search Report and Written Opinion issued in corresponding EPO application No. 07019251.3, dated Feb. 1, 2008 (8 pgs).
First Office Action issued in corresponding Chinese application No. 200480023382.4, dated Aug. 22, 2008 (15 pgs).
International Search Report and Written Opinion issued in corresponding PCT application No. PCT /GB2009/051574, dated Jun. 7, 2010 (28 pgs).
Combined Search and Examination Report issued in corresponding application No. GB1019839.8, dated Dec. 1, 2010 (2 pgs).
Combined Search and Examination Report issued in corresponding application No. GB 0418050.1, dated Nov. 29, 2004 (7 pgs).
Examination Report issued in corresponding application No. 09 756 353.0-1257, dated Aug. 17, 2012 (5 pgs).
Further examination as result of telephone conversation with examiner issued in corresponding EPO application No. 03 787 902.0 (1 pg).
Letter from IP Australia regarding third party application for re-examination dated Sep. 21, 2011 involving corresponding application No. 2008207412 (2 pgs).
Invitation to Pay Additional Fees with International Search Report issued in corresponding application No. PCT/GB2004/003481, dated Nov. 12, 2004 (8 pgs).
Notice for Reasons for Rejection issued in corresponding Japanese application No. 2006/523053, dated Nov. 8, 2010, with English translation (4 pgs).
International Search Authority issued in corresponding PCT application PCT/GB03/03577 dated, Dec. 9, 2003 (5 pgs).
International Search Report issued in corresponding PCT application PCT/GB03/03577 dated Aug. 14, 2003 (9 pgs).
Office Action issued in related U.S. Appl. No. 12/627,844, dated Feb. 28, 2014 (22 pgs).
Notice of Allowance issued in related U.S. Appl. No. 13/403,806, dated Mar. 12, 2014 (16 pgs).
Notice of Allowance issued in related U.S. Appl. No. 29/416,561, dated May 9, 2014 (7 pgs).
Japanese Office Action (no translation) issued in releated application No. 2012-38633, dated Apr. 23, 2013 (2 pgs).
Office Action issued in related U.S. Appl. No. 13/403,806, dated Apr. 25, 2013 (6 pgs).
Notice of Allowance issued in related U.S. Appl. No. 29/407,461, dated Jun. 12, 2013 (26 pgs).

(56) References Cited

OTHER PUBLICATIONS

Office Action issued in related U.S. Appl. No. 13/130,555, dated Jun. 20, 2014 (36 pgs).
Office Action issued in related U.S. Appl. No. 29/475,489, dated Jun. 20, 2014 (25 pgs).
International Search Report and Written Opinion issued in related application No. PCT/GB2013/050180, dated May 7, 2013 (13 pgs).
Combined Search and Examination Report issued in related application No. GB1301478.2, dated May 23, 2013 (5 pgs).
Notice of Allowance issued in related U.S. Appl. No. 29/449,900, dated Jul. 24, 2013 (11 pgs).
Office Action issued in related U.S. Appl. No. 13/403,806, dated Aug. 15, 2013 (45 pgs).
"The Development of the Laryngeal Mask-a Brief History of the Invention, Early Clinical Studies and Experimental Work from Which the Laryngeal Mask Evolved" A.I.J. Brain, European Journal of Anesthesiology, 1991, Supplement 4, pp. 5-17.
PCT International Search Report, dated Jan. 14, 2009 (20 pgs).
Office Action issued in U.S. Appl. No. 29/353,658 dated Aug. 19, 2011 (10 pgs).
International Search Report and Written Opinion issued in Applicant's corresponding UK Patent Application Serial No. GB0817776.8.
UK Search Report issued in corresponding application No. GB1110775.2, dated Oct. 18, 2011 (8 pgs).
Office Action issued in U.S. Appl. No. 12/627,844, dated Sep. 17, 2015 (26 pgs).
Office Action issued in U.S. Appl. No. 29/428,284, dated Mar. 19, 2015 (6 pgs).
Notice of Allowance issued in U.S. Appl. No. 14/315,141, dated Nov. 13, 2015 (36 pgs).
Office Action issued in U.S. Appl. No. 29/428,284, dated Nov. 10, 2015 (5 pgs).
Office Action issued in U.S. Appl. No. 29/512,931, dated Nov. 23, 2015 (20 pgs).
Office Action issued in U.S. Appl. No. 29/512,932, dated Nov. 19, 2015 (19 pgs).

* cited by examiner

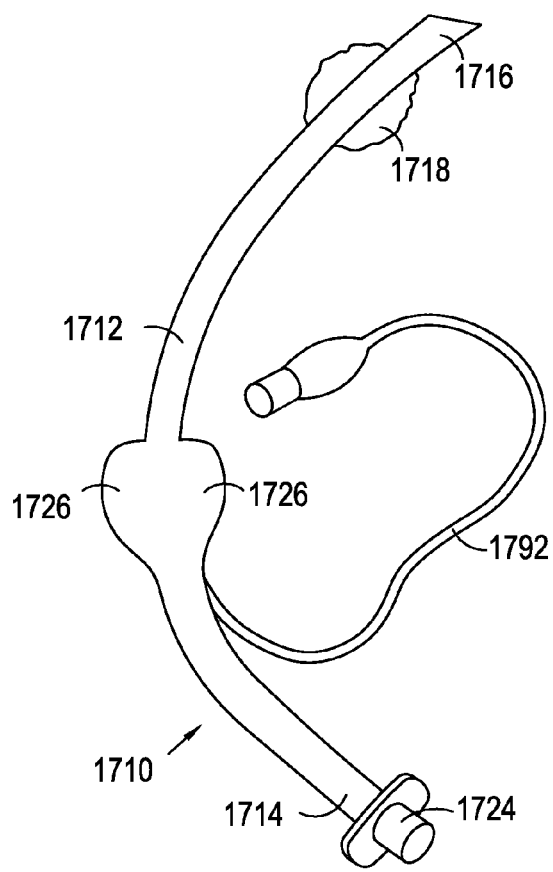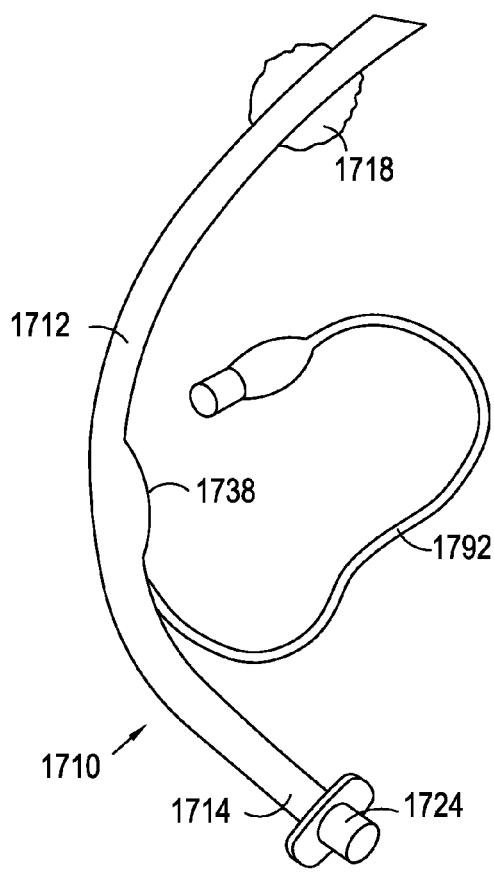
Figure 41  Figure 42
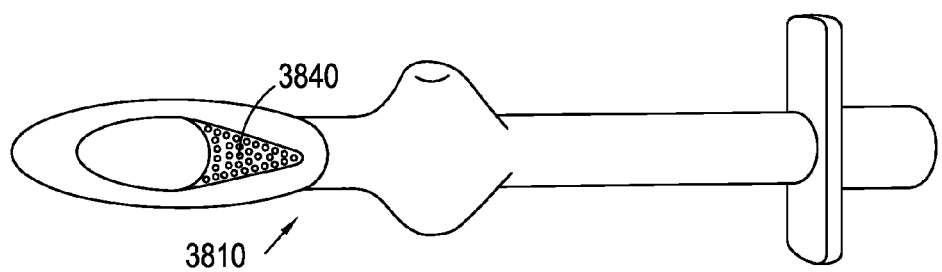
Figure 43
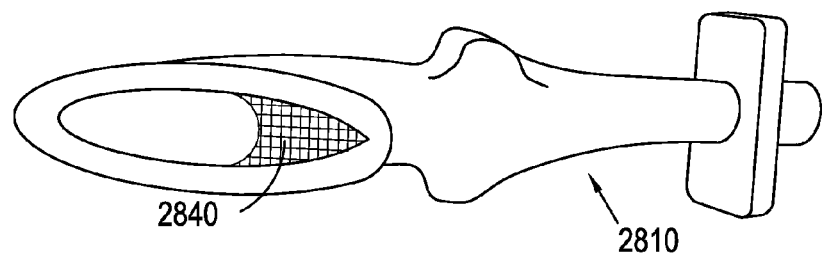
Figure 44

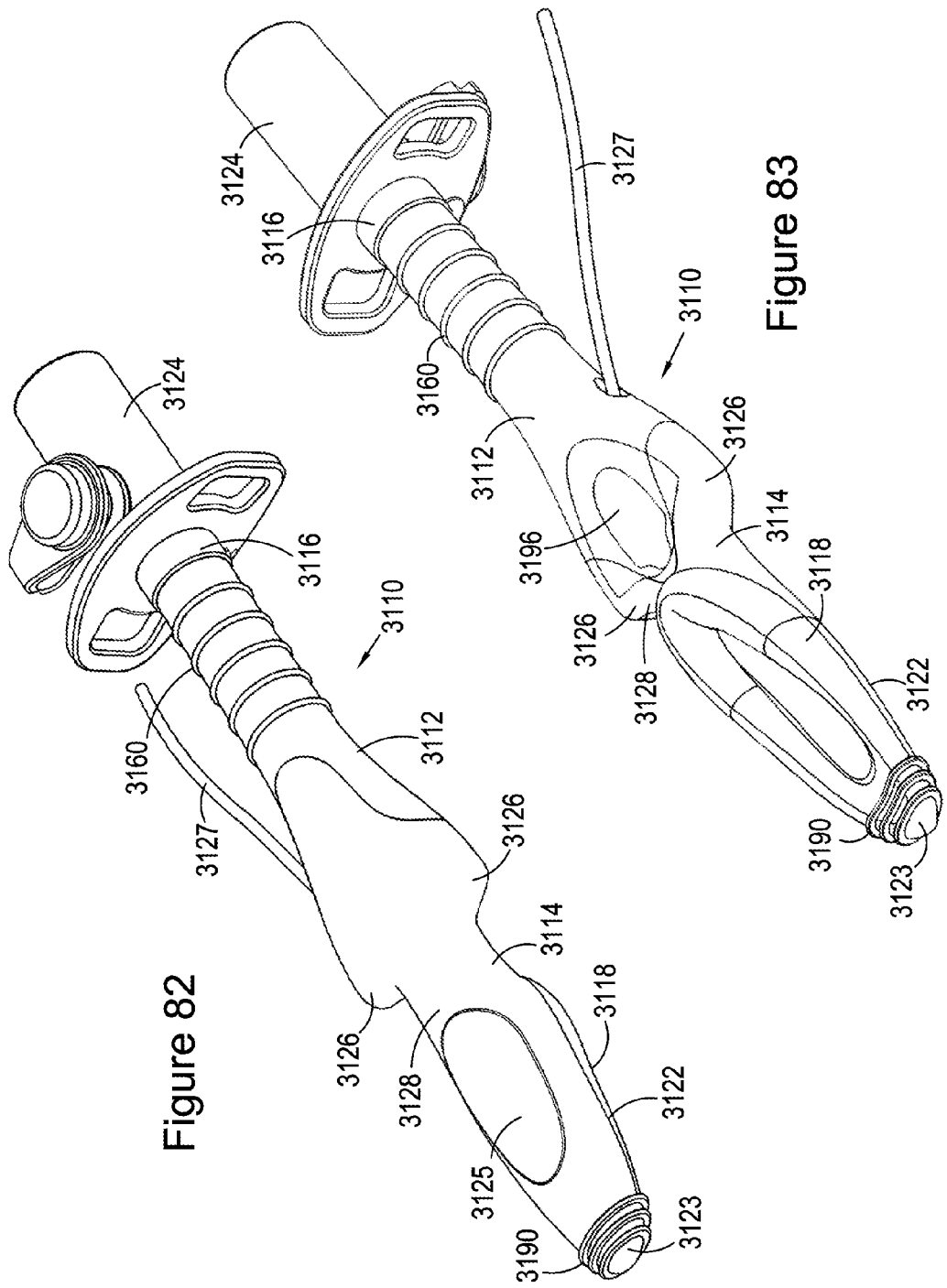

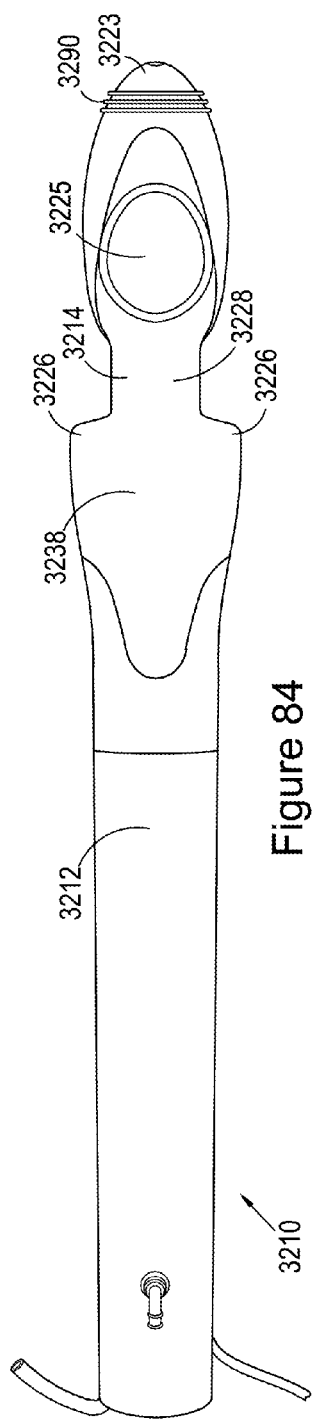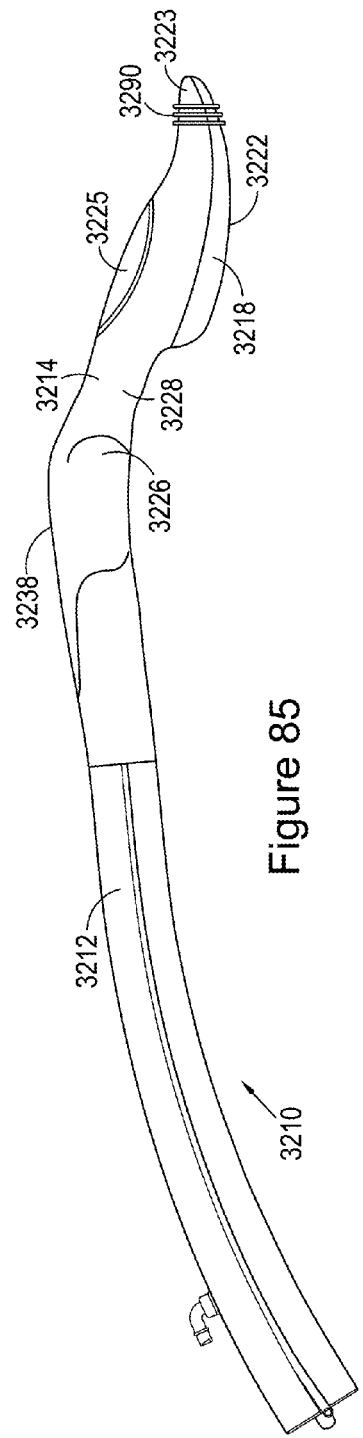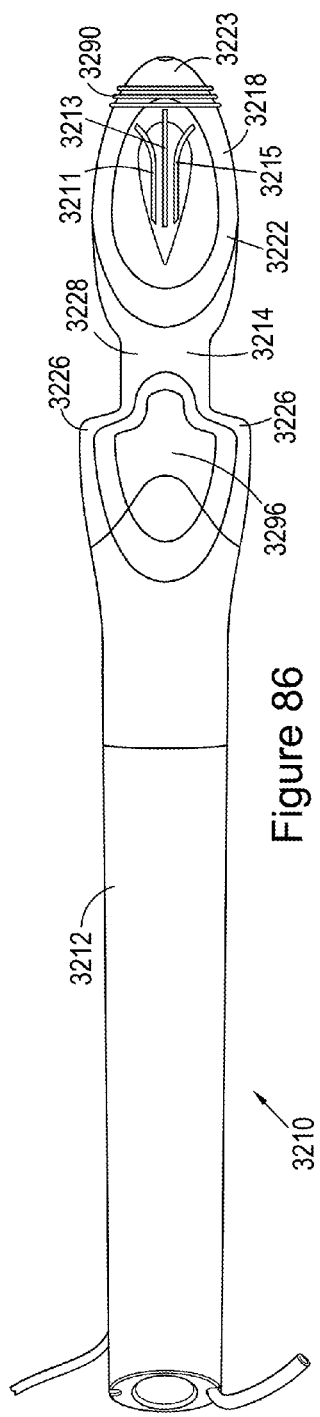

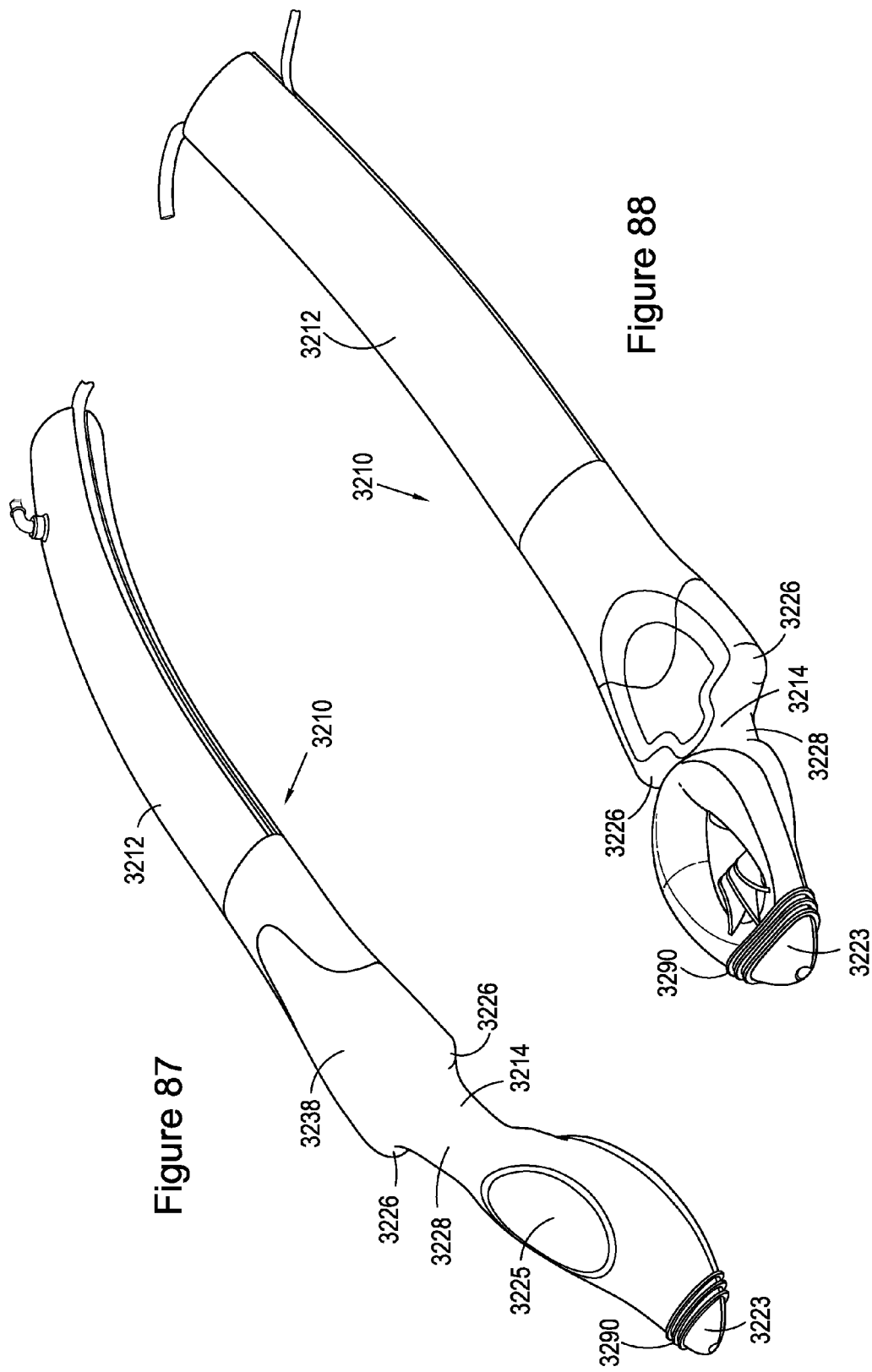

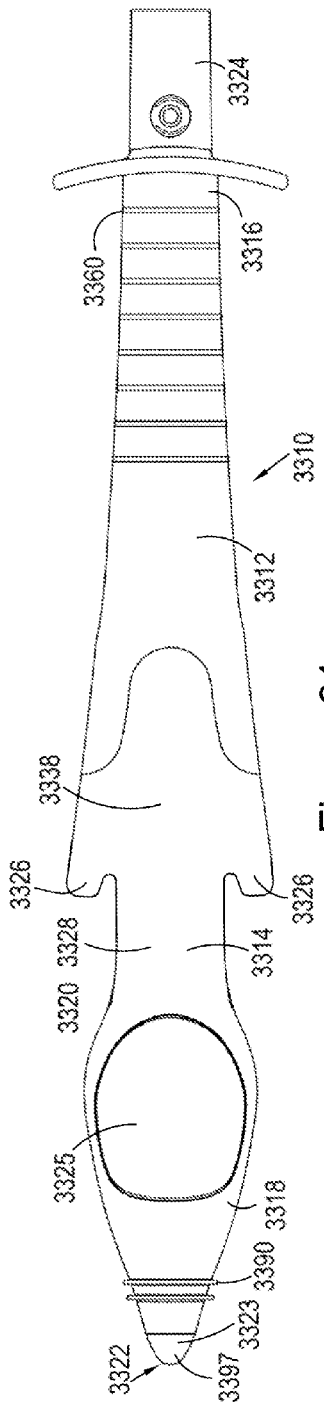
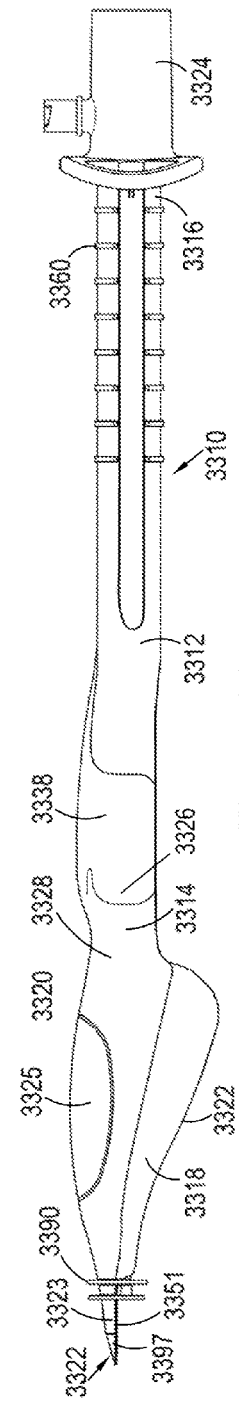
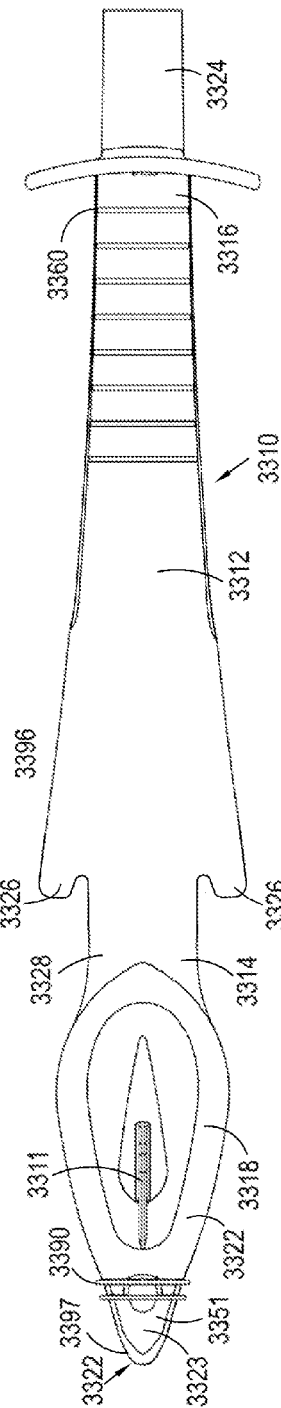
Figure 91
Figure 92
Figure 93

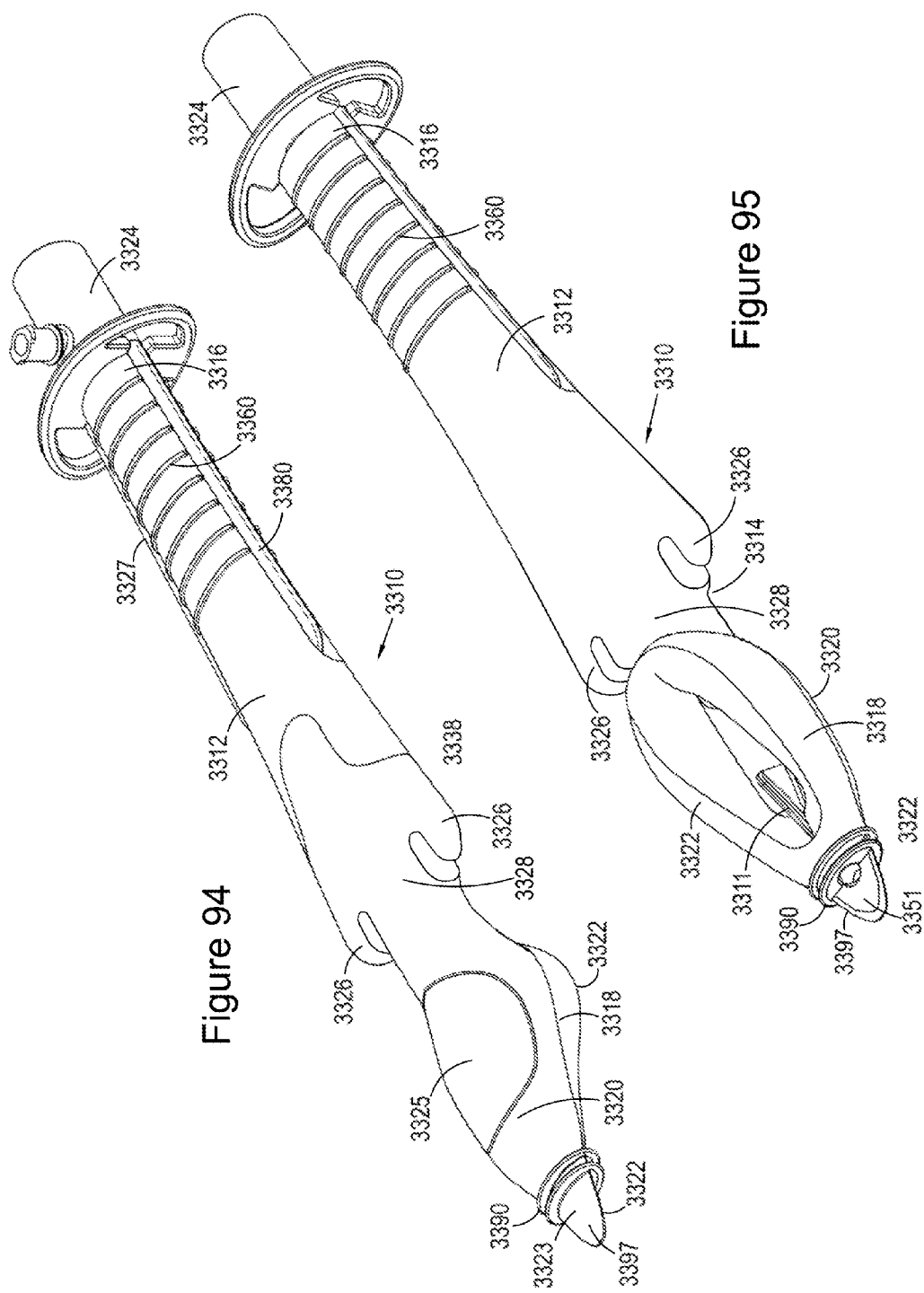

STOPPER DEVICE

FIELD OF THE INVENTION

The present invention relates to medical devices, namely safety airway devices. It is applicable to supraglottic devices including pharyngeal, laryngeal, and tracheal and endobroncheal airway devices and to their methods of manufacture. The present invention is also applicable to other type of devices which also involve the administration of oxygen and/or anaesthetic gases to a human or animal patient through spontaneous breathing, assisted ventilation or Intermittent Positive Pressure Ventilation (IPPV) during a surgical procedure or resuscitation.

BACKGROUND TO THE INVENTION

Various airway devices are known and are currently used in spontaneous breathing or IPPV to anaesthetise patients, or for resuscitation applications. The main focus of developments in such devices has heavily leaned towards ensuring the best shape and material combination to make such devices easy to insert and to improve sealing pressures once the device is in situ within the patient. This has been the case for both supraglottic devices which seal within the larynx and endotracheal tubes which seal within the trachea.

In particular in the case of supraglottic devices, the requirement for clinical knowledge and experience is invaluable in the decision-making process of choosing the correctly sized device for a given set of patient parameters. However, such decisions can still be very subjective and are arbitrarily related to the weight of the given patient, and will therefore be variable depending on the particular experience or preferences of individual clinicians. This increases the chance of selecting and using a device of the incorrect size for the given patient. Selecting an incorrectly sized device will lead to undesirable consequences, for example if a device that is too small for the patient is chosen this is likely to result in an over-insertion of the device beyond the larynx and deep into the trachea in the case of laryngeal airway devices, which can potentially result in traumatising and/or damaging the trachea, esophagus, vocal chords and upper esophagus in both human and animal patients.

The issues and consequences of incorrect device selection are particularly relevant in paediatric use. In pediatrics the stage of anatomical development is in a state of constant flux, with various rates of change from individual to individual, until adulthood is reached. When adulthood is reached the shapes of the internal anatomical structures become more stable and thus provide a more reliable environment for correct device size selection and use. Therefore, in pediatrics the risk of incorrect device size selection, which may result in over insertion or lack of optimal sealing forces of a device in the patient is much greater in pediatrics than in adults. This matter is highly exacerbated within veterinary anaesthesia situations as the anatomical parameters can vary significantly not only between species but also within a species type, such as in the case of dogs.

In addition to the problem of over-insertion of such supraglottic devices, another problem which can arise is accidental rotation of the device after insertion. This type of incident could result in the device being displaced from the correct sealing position within the human or animal patient. Some attempts have been made in the prior art to produce devices which do not readily succumb to rotation after insertion. This has been done by either widening the surface area of the device that is in contact with the top of the tongue or through the use of external fixation systems. However, such attempts have not been wholly successful in solving the rotation problem. In the case of external fixation this requires an additional effort on behalf of the clinician to secure the device and therefore unfortunately this is not always undertaken.

Yet another problem which still exists in present supraglottic devices, and in particular in airway type devices, is the possibility of the epiglottis of the human or animal patient down folding and occluding the airway within the device, thus blocking off the gas flow to and from the patient. The problem associated with down folding epiglottis is most applicable to paediatric and animal patients who have a large range in both the flexibility and size of the epiglottis.

SUMMARY OF THE INVENTION

According to a first aspect of the present invention there is provided an airway device for human or animal use, the device includes an airway tube having a first end and a second end, wherein the device further includes a shoulder, the shoulder extends laterally from the airway tube, the shoulder is adapted to contact the faucial pillars of the human or animal patient to prevent over-insertion of the device in use. This is particularly advantageous as an airway device is provided which has a positive stop mechanism in the form of the shoulder which is either formed integrally with or separate from the device and which assists in preventing over insertion of the airway device beyond the desired location.

In one alternative the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal with the laryngeal inlet of the patient. In this alternative an airway device is provided which has a stop mechanism in the form of the shoulder which is either formed integrally with or separate from the device and which assists in preventing over insertion of the airway device beyond the laryngeal inlet of the patient. Insertion of the airway device beyond the laryngeal inlet of the patient could result in serious trauma to both the trachea and to the vocal chords. Preferably the shoulder is larger in width than the width of the laryngeal cuff.

In a second alternative there is provided an airway device for insertion into the trachea or bronchi of a human or animal patient including an airway tube having a first end and a second end, a cuff located at or near the first end of the airway tube, the cuff is adapted to engage the wall of the trachea or bronchi in use. For devices such as endotracheal tubes the shoulders could be used to aid the identification of when the device has reached a maximum insertion length. Preferably the shoulder is larger in width than the width of the cuff.

According to either alternative, as well as preventing over insertion of the device the shoulder stop mechanism rests directly in contact with or in very close proximity to the faucial pillars which also assists in both minimizing rotational movement of the device and the amount of horizontal and vertical movement of the device when in situ. It is the location and extent of the lateral width of the shoulder relative to the amount of anatomical space there is around the faucial pillars of a patient that combines to significantly restrict the ability to move the device once in situ and prevents accidental displacement of the device within the patient which may compromise the seal. The shoulder is configured to make contact with the faucial pillars of a human or animal patient to prevent over-insertion of the device in use. In creating contact with the faucial pillars a positive stopping feature is created which the shoulder cannot move beyond to provide a device which in reasonable terms stops any over insertion as the device simply will not move beyond the desired location in the patient.

The shoulder may be integral with the airway tube or in the alternative it may be detachably attached to the airway tube. In the case of an integral shoulder this will be more appropriate in the creation of new devices whereas the detachable shoulder may be more appropriate to retro-fit to existing devices or simply added onto existing devices in problem patient situations, but also removable in the event that the patient has very different internal sizing to that which would be expected. The present invention therefore not only includes airway devices which have been provided with a shoulder, but also shoulders which are retrofittable to existing airway devices.

In one alternative the shoulder is formed from a material with a Shore hardness of 80 or less on the A scale, more preferably 40 or less on the A scale, even more preferably 20 or less of the A scale, yet more preferably 10 or less on the A scale, most preferably 0 or less on the A scale. The shoulder may have a Shore hardness between and including 80 to 000 on the A scale, more preferably between and including 40 to 000 on the A scale, still more preferably between and including 20 to 000 on the A scale, yet more preferably 10 to 000 on the A scale. It is important to provide devices with a harder shoulder for use in horses, for example, which are much larger and stronger animals than dogs, cats and rabbits. If a soft material is used in a device for a horse then the airway tube is more likely to kink along with other elements of the airway device which will result in the airway being occluded. A harder material is also important to use in larger animals, such as horses, because the length of the device is very large versus other species. This is because the distance between the mouth opening and the laryngeal and oesophageal inlets is much greater than that in many other species, in part because the animal is much larger. The problem is that when the airway device is scaled up to a size which would be appropriate for use in a horse, for example, the device is more prone to flex and kink, which might result in occlusion of the airway tube, if it were made out of the same soft material used for smaller species. Therefore harder materials need to be used for both the shoulder and the airway tube to give stronger resistance to kinking of the device to reduce the chance that the airway will become blocked and cut off the airflow.

In an alternative the shoulder may include a hard core with a softer external covering or skin. In this alternative the hard core may be of a Shore hardness between 40 and 90 on the A scale and the softer external covering may be of a Shore hardness between 000 and 40 on the A scale.

The shoulder may be formed from a solid material which has a uniform density throughout the shoulder. In an alternative the shoulder may be hollow, in this alternative the shoulder may have either a flexible or rigid shell, wherein the shoulder has a flexible shell the shoulder may be pre-filled with air or any other suitable fluid. In a further alternative the shell of the shoulder may be pre-filled with a gel or a foam.

In an alternative the shoulder includes an inflatable region. The inflatable region may just be a part of the shoulder or in the alternative may be the full extent of the shoulder.

In a further alternative the shoulder includes a rib or fin. In yet another alternative the shoulder includes a plurality of ribs or fins. In this alternative the shoulder is preferably formed from a material with a Shore hardness of 80 or less on the A scale, preferably 40 or less on the A scale, more preferably 20 or less on the A scale, even more preferably 10 or less of the A scale, most preferably 0 or less on the A scale. The shoulder may have a Shore hardness between and including 80 to 000 on the A scale preferably 40 to 000 on the A scale, more preferably between and including 20 to 000 on the A scale, still more preferably between and including 10 to 000 on the A scale.

Whether the shoulder is formed from a soft material, a hard core with a covering of a soft material, an inflatable region, a rib or fin or a plurality of ribs or fins the shoulder should be soft so as to minimize any trauma to surrounding tissues upon insertion of the device, in particular to the faucial pillars and surrounding tissues. The width of shoulder has to be greater than the width of the faucial pillars but less than the internal width of the back of the mouth to create a definite stop feature, permit the device to be inserted into correct position, and not rub against the inside of the mouth which may cause irritation during use. In addition this shoulder should be shaped ideally as close to being perpendicular to the direction of the airway tube so as to maximize the resistance for the shoulder to bypass the elasticity of the faucial pillar tissues. The angle of the leading face of the shoulder is preferably ±15° to perpendicular to the airway tube. The formation of the shoulder from a soft or inflatable material is designed to reduce any possible trauma that could be caused when the shoulder of the airway device comes into sudden contact with the faucial pillars to provide the feature of the positive stop.

Upon insertion of the airway device the shoulder will eventually impact against the faucial pillars and will naturally bounce back and will rest away from being in direct contact with the faucial pillar structures thus not causing any trauma. A slight vertical angling of the leading edge of the shoulder in some embodiments will ensure to minimize possible surface contact area and avoid traumatisation of the faucial pillar structures.

The shoulder is adapted to create a positive stop at the faucial pillars of the human or animal patient by being sized significantly larger than the distance between the faucial pillars. Some of the prior art devices have a buccal cavity stabilizer, this feature, however, does not create a positive stop as the buccal cavity stabilizer is only slightly larger than the faucial pillars. Furthermore, the gradual smooth contouring of the buccal cavity stabilizer in the prior art devices actually acts to stretch out the distance between the elastic tissues of the faucial pillars. This stretching of the faucial pillars results in over insertion of the device and can lead to the trauma described above. Thus the shoulder is preferably not only wider than the faucial pillar but also that the leading face or edge of the shoulder is substantially perpendicular to the airway tube and thus substantially parallel with the contact surface of the faucial pillar to create a positive stop.

In addition for certain species the shoulder may be provided with forward facing protrusions. The forward facing protrusions would be located on the leading face of the shoulder. The forward facing protrusions would be configured to locate into anatomical cavities which are present in dogs, for example, after the pharyngeal arches. In general most breeds of dogs have a very wide pharyngeal arch as the dogs are designed to consume large volumes of food very rapidly. The fact that the pharyngeal arch is much wider in dogs than that of other species may result in the airway device not fitting as tightly with the pharyngeal arch as might be desired in practice and thus to minimize any risk of the shoulder passing beyond the desired located the shoulder may be provided with the described forward facing protrusions. The forward facing protrusions being adapted to fit into the anatomical cavity region to make the whole airway device fit more securely and not easily by-pass the pharyngeal arches. It is worth bearing in mind that the pharyngeal arches are particularly elastic in dogs. The forward facing protrusions furthermore preferably result in the formation of a forward facing indentations or cavities. The cavities are preferably U or V shaped and are adapted to fit the thin protruding pharyngeal arches of a dog for example. Most preferably the U or V shaped cavities interengage with the pharyngeal arches to retain the device in position.

The shoulder ensures that small cuffs on airway devices will stay in position correctly within the larynx of the patient and not go beyond the desired position which otherwise would cause damage to the patient. The shoulder acts much more positively to locate the correct in situ position of the device than only using the tip of the laryngeal mask cuff to judge the amount of insertion and to stop over insertion, as in some species the esophagus structures can be more elastic in nature than others and can therefore continue to yield. This yielding allows the device to keep progressing forward and beyond the ideal sealing position for effective use of the airway device.

Another advantage of the shoulder is that it acts to resist rotation of the airway device as it sits more positively on the tongue region located at the back of the mouth. This gives more resistance to rotation as the volume within the back of the mouth becomes constrained. The use of an optional flared region from the shoulder back towards the tubular section of the airway tube to create a shield type form could be also used to increase surface contact with the face of the tongue to slightly increase resistance against airway device rotation. The flaring is not a requisite to the dead stop feature of the shoulder working but offers a more effective resistance to movement using a different portion of the mouth of the patient.

It is worth noting that for the shoulder to be effective this feature need not be made from a "soft" material i.e. Shore hardness of 80 or less on the A scale. The shoulder may in the alternative be made from a very hard rigid material such as a very hard rigid plastics material. When the shoulder is made from a very hard rigid plastics material the shoulder will still prevent the airway device from being inserted too for into the human or animal patient and assist in preventing unwanted rotation of the airway device. However, if a very hard rigid plastics materials is used, some trauma may result where the hard rigid plastics material comes into contact with the patient. Thus a softer material is preferred, but that is not to say that hard materials are not effective. If a hard plastics material is used it may optionally be covered in a soft material.

Preferably the shoulder additionally includes one or more suction channels. The suction channels are provided to assist the removal of fluids which may build up at the back of the mouth. The airway device may also be provided with an oesophageal gastric channel. The suction channels may be integral with or separate from the oesophageal gastric channel if one is provided. In a further alternative the airway device may simply be provided with an oesophageal gastric channel.

Preferably there is provided a raised portion on the back dorsal portion of the airway tube. Preferably the raised portion is adapted to contact the palatoglossal arch of the human or animal patient in use. The raised portion is preferably a soft region on the airway tube distal to the cuff, above the shoulder, adapted to face towards and to be located within the cavity of the upper mouth arch (palatoglossal arch) in use. This raised portion offers two major benefits; the first is that its height and front region will collide with the upper arch region of the patient if the clinician attempts to over insert the device. Also if the device is twisted at the connector end of the device for example, the sides of raised portion will collide with the sides of the upper arch cavity on the patient such that it very rapidly reaches a point which restricts any further rotational movement and therefore will keep the device secure from rotation and will not result in the airway device becoming dislodged from the optimal sealing position on the patient airway. The raised portion also significantly restricts any upward and downward leveraging movement and sideways or lateral movement of the airway device thus it significantly constrains the device so that it stays in the correct position once correctly inserted and for the duration of clinical use.

The raised portion can be narrowed to ensure in some species it bypasses any contact which might occur with the teeth of the patient.

When the raised portion includes a bulge it is preferably formed from a material with a Shore hardness of 80 or less on the A scale, more preferably formed from a material with a Shore hardness of 40 or less on the A scale, even more preferably 20 or less on the A scale, yet more preferably 10 or less of the A scale, most preferably 0 or less on the A scale. The raised portion may have a Shore hardness between and including 80 to 000 on the A scale, more preferably between and including 40 to 000 on the A scale, still more preferably between and including 20 to 000 on the A scale, yet more preferably 10 to 000 on the A scale. It is important to provide devices with a harder raised portion for use in horses, for example, which are much larger and stronger animals than dogs, cats and rabbits. If a soft material is used in a device for a horse then it is more likely to kink which will result in the airway being occluded. A harder material is also important to use in larger horses, because the length of the device is very large versus other species. This is because the distance between the mouth opening and the laryngeal and oesophageal inlets is much greater than that in many other species, in part because the animal is much larger. The problem is that when the airway device is scaled up to a size which would be appropriate for use in a horse, for example, the device is more prone to flex and kink, which might result in occlusion of the airway tube, if it were made out of the same soft material used for smaller species. Therefore harder materials need to be used for both the raised portion and the airway tube to give stronger resistance to kinking of the device to reduce the chance that the airway will become blocked and cut-off the airflow.

In an alternative the raised portion may include a hard core with a softer external covering or skin. In this alternative the hard core may be of a Shore hardness between 40 and 90 on the A scale and the softer external covering may be of a Shore hardness between 000 and 40 on the A scale.

In addition or in the alternative when the raised portion includes a plurality of ribs or fins they are preferably formed from a material with a Shore hardness of 80 or less on the A scale, preferably 40 or less on the A scale, more preferably 20 or less on the A scale, even more preferably 10 or less of the A scale, most preferably 0 or less on the A scale. The raised portion may have a Shore hardness between and including 80 to 000 on the A scale preferably 40 to 000 on the A scale, more preferably between and including 20 to 000 on the A scale, still more preferably between and including 10 to 000 on the A scale.

The raised portion can be constructed from a number of configurations: for example and not restricted to, solid soft material ranging from Shore hardness 000 to 80 on the A scale or from the use of a series of webs or rib type configuration following the same form of similar hardness or up to Shore hardness 80 on the A scale or from the provision of an inner core made from a harder material with a Shore hardness of 80 to 000 on the A scale and an outer covering or skin made from a softer material with a Shore hardness of 40 to 000 on the A scale. This raised portion both alone and in conjunction with the shoulder significantly limits rotational, sideways, lateral and leverage movement of the device and significantly secures the airway device from being over inserted, and rotated or leveraged out of optimal sealing locations. Further in addition or in the alternative the raised portion may include an inflatable region. The inflatable region may just be a part of the raised portion or in the alternative may be the full extend of the raised portion.

The raised portion may be formed from a solid material which has a uniform density throughout the raised portion. In an alternative the raised portion may be hollow, in this alternative the raised portion may have either a flexible or rigid shell, when the raised portion has a flexible shell the raised portion may be pre-filled with air or any other suitable fluid. In a further alternative the shell of the raised portion may be pre-filled with a gel or a foam.

These improvements increase the safety of use for both experienced and novice users of airway devices by significantly reducing the potential hazards associated with inserting blindly various forms of airway devices into patients. These improvements provide for a device which is tailored to fit into the anatomical architecture and that the device will be correctly inserted and will not twist or flick out of position once inserted.

It should be made clear that the features of the shoulder portion and the raised portion are generally shown as both being present in all of the drawings it is not essential to the invention that that airway device should have the raised portion, and the airway device may just have the feature of the shoulder. The raised portion is not essential to the working of the shoulder and simply provides additional security.

It should be noted that the airway device, including the cuff, shoulder and raised portion (where present) are preferably formed from a polymeric or other plastics material. Such polymeric materials are intended to cover thermo-set rubbers, such as silicone, natural rubbers, neoprene and polyurethanes.

In the alternative described above wherein the first end of the airway tube is surrounded by a laryngeal cuff, in one alternative the laryngeal cuff has a tip, the tip being angled towards the back dorsal portion of the laryngeal cuff. Preferably the tip is angled between and including 5° to 80° from the horizontal plane of the laryngeal cuff. This angling has the effect of increasing the surface area of the tip as more of it engages with the esophagus thus this creates a rapid rate of engagement and seal with the esophagus and therefore another form of resisting over insertion of the airway device as would be the case if the tip were narrow and straighter. The tip may have a back dorsal portion and a front face portion, the back dorsal portion being predominately formed from a harder material than the front face portion so as to give the tip strength against folding on itself and the very soft underside significantly reduces the possibility of damage to the esophagus.

In a further alternative wherein the first end of the airway tube is surrounded by a laryngeal cuff, in one alternative the laryngeal cuff has a tip, wherein the tip includes an annular flange sealing portion which may include a plurality of annular flange sealing portions, wherein the annular flange sealing portion is adapted to wedge into upper esophagus region of the human or animal patient. The annular flange sealing portions are provided for improved sealing of the tip of the laryngeal cuff in the upper esophagus region of the human or animal patient. The annular flange sealing portions are preferably formed from a soft polymeric or other plastics material with a Shore hardness of between 40 and 000 on the A scale. The annular flange sealing portions allow for better sealing with a more variable range of upper oesophageal anatomical features.

In yet a further alternative wherein the first end of the airway tube is surrounded by a laryngeal cuff, in one alternative the laryngeal cuff has a tip, wherein the tip portion is blade shaped for manipulation of the epiglottis of the patient. The tip portion may have a contoured surface on the back dorsal portion of the cuff and a substantially flat surface on the front face portion of the cuff. This particular shape arrangement allows for the clinician to peel back the epiglottis of the human or animal patient at the same time as the airway device is being inserted in a single action. It is necessary to move the epiglottis in animals such a dogs prior to or as the airway device is being inserted, which have very large and floppy epiglottis compared to some other species, to assist in preventing downfolding which would result in occlusion of the airway and thus the air flow to the patient. The tip portion in one alternative may be contoured in the same way as the dorsal portion of the cuff, or in the alternative may be further contoured so that the depth of the tip is reduced substantially so that it feathers out to the blade like tip.

In a further alternative the airway tube is provided with a concave portion. Preferably the concave portion is in use adapted to contact the convex portion of the back of the tongue of the human or animal patient. When pressure is applied to the tongue it can result in constriction of the blood vessels in the tongue, which results in a condition know as blue tongue. In order to relieve any pressure which might otherwise be placed on the back of the tongue a concave portion may be provided so that pressure is not applied in that region. The concave portion in one alternative may be a single concave region, or in the alternative may be a plurality of concave regions which may result from a series of depressions or dimples or in the alternative from a series of bumps or protrusions. Further in the alternative the concave portion may be a plurality of concave regions formed from a series of corrugations or grooves running horizontally or vertically along the underside of the device, or further in the alternative be formed from a series of concentric rings. The concave portion not only acts to relieve pressure, but also lends stability to the location of the device when in situ in the human or animal patient.

In a further alternative the first end of the airway tube includes a perforated plate or mesh which is adapted to prevent the epiglottis of a human or animal patient down folding into the airway tube in use. There is still the concern of epiglottis down folding into the airway tube which would result in a blocking of the flow of gases to and from the patient. One way to increase safety is to apply a mesh or a perforated plate between the upper and lower regions of the laryngeal cuff so that the mesh or perforated plate sits below the surface used for sealing but high enough to inhibit occlusion of airflow by the epiglottis down folding into the airway tube.

In a further alternative to prevent downfolding of the epiglottis and occlusion of the airway a bracket, or plurality of brackets may be provided which extend part or full way across the opening of the cuff either from the distal and opening, the proximal and opening or both. The bracket(s) not only prevent occlusion of the airway but also provide strength to the cuff. The bracket(s) may in one alternative extend from the proximal end opening, in another alternative from the distal end opening, in another alternative the bracket(s) may extend across the full length of the opening. The bracket(s) may simply extend across the opening, or in the alternative may be the full height of the opening and contact the back of the opening. The bracket(s) may further be provided with notches or cut outs in their front face surface such that in the event that the epiglottis comes to rest on the bracket(s) the flow of air between the bracket(s) is not effected such that there are no turbulent effects. Preferably the bracket(s) are formed from a substantially rigid material so that they support the weight of the epiglottis rather than flexing which might result in the occlusion of the airway if the bracket(s) flex under the weight of the epiglottis.

In a further alternative a portion of hard plastics material may be provided at the distal opening of the cuff to strengthen the tip of the cuff and to act as a flow director.

In a further alternative the airway device may be provided with an inflatable back cuff, preferably the inflatable back cuff is located on the back dorsal portion of the cuff and when deflated is flush with the surface of the back dorsal portion of the cuff. This arrangement means that the upper surface of the inflatable cuff remains as rigid as the dorsal portion of the laryngeal cuff. The inflatable back cuff acts as a gap filler to ensure a seal between the front face of the cuff and the laryngeal inlet to counteract for any inter species variables such that the device is inhibited from any possible rotation when in situ in the patient. Preferably the inflatable back cuff has a defined perimeter so that it is adapted to inflate in substantially a single direction so there is no substantial change in the shape of the front face of the laryngeal cuff which forms the seal on and around the laryngeal inlet of the patient. Any inflation line provided is arranged such that it does not impede the gas flow to the patient. Preferably the inflatable back cuff is formed from a material with a Shore hardness of less than 20 on the A scale, more preferably less than 10 on the A scale.

In another alternative the airway device may be designed to split into two portions about the airway tube. It is important for the device to fit into standard autoclaves for sterilization and those devices for larger animals such as horses are too large to fit if they cannot be broken down into smaller components.

If an inflatable portion is provided in the device, i.e. shoulder, raised portion or back cuff, the inflation line may be located in a notch or groove located along the side of the airway tube, so that it does not impede the gas flow to the patient.

If an oesophageal gastric tube or suction tube is provided, the tube may be located in a notch or groove located along the side of the airway tube, so that it does not impede gas flow to the patient.

According to a second aspect of the present invention there is provided an airway device for human or animal use, the device includes an airway tube having a first end and a second end, the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal with the laryngeal inlet of the patient, wherein the laryngeal cuff has a tip, the tip being angled towards the back dorsal portion of the laryngeal cuff.

Preferably the tip is angled between and including 5° to 80° from the horizontal plane of the laryngeal cuff. Preferably the tip has a back dorsal portion and a front face portion, the back dorsal portion being formed from a harder material than the front face portion. The tip is preferably adapted to wedge into upper esophagus region of the human or animal patient.

Preferably the tip includes an annular flange sealing portion which may include a plurality of annular flange sealing portions, wherein the annular flange sealing portion is adapted to wedge into upper esophagus region of the human or animal patient. The annular flange sealing portions are provided for improved sealing of the tip of the laryngeal cuff in the upper oesophageal region of the human or animal patient. The annular flange sealing portions are preferably formed from a soft polymeric or other plastics material with a Shore hardness of between 40 and 000 on the A scale. The annular flange sealing portions allow for better sealing with a more variable range of upper oesophageal anatomical features.

According to a third aspect of the present invention there is provided an airway device for human or animal use, the device includes an airway tube having a first end and a second end, the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal with the laryngeal inlet of the patient, wherein the tip portion includes an annular flange sealing portion. Preferably the tip includes a plurality of annular flange sealing portions, wherein the annular flange sealing portion is adapted to wedge into upper esophagus region of the human or animal patient. The annular flange sealing portions are provided for improved sealing of the tip of the laryngeal cuff in the upper oesophageal region of the human or animal patient. The annular flange sealing portions are preferably formed from a soft polymeric or other plastics material with a Shore hardness of between 40 and 000 on the A scale. The annular flange sealing portions allow for better sealing with a more variable range of upper oesophageal anatomical features.

According to a fourth aspect of the present invention there is provided an airway device for human or animal use, the device includes an airway tube having a first end and a second end, the first and of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal against the laryngeal inlet of the patient, wherein the airway tube is provided with a concave portion.

Preferably the concave portion is in use adapted to contact the convex portion of the back of the tongue of the human or animal patient. When pressure is applied to the tongue it can result in constriction of the blood vessels in the tongue, which results in a condition known as blue tongue. In order to relieve any pressure which might otherwise be placed on the back of the tongue a concave portion may be provided so that pressure is not applied in that region. The concave portion in one alternative may be a single concave region, or in the alternative may be a plurality of concave regions which may result from a series of depressions or dimples or in the alternative from a series of bumps or protrusions. Further in the alternative the concave portion may be a plurality of concave regions formed from a series of corrugations or grooves running horizontally or vertically along the underside of the device, or further in the alternative be formed from a series of concentric rings. The concave portion not only acts to relieve pressure, but also lends stability to the location of the device when in situ in the human or animal patient.

According to a fifth aspect of the present invention there is provided an airway device for human or animal use, the device includes an airway tube having a first end and a second end, the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal against the laryngeal inlet of the patient, wherein the laryngeal cuff has a tip portion, the tip portion being blade shaped for manipulation of the epiglottis of the patient. The tip portion may have a contoured surface on the back dorsal portion of the cuff and a substantially flat surface on the front face portion of the cuff. This particular shape arrangement allows for the clinician to peel back the epiglottis of the human or animal patient at the same time as the airway device is being inserted in a single action. It is necessary to move the epiglottis in animals such a dogs prior to or as the airway is being inserted, which have very large and floppy epiglottis compared to some other species, to assist in preventing downfolding which would result in occlusion of the airway and thus the air flow to the patient. The tip portion in one alternative may be contoured in the same way as the dorsal portion of the cuff, or in the alternative may be further contoured so that the depth of the tip is reduced substantially so that it feathers out to the blade like tip.

According to a sixth aspect of the present invention there is provided an airway device for human or animal use, the device includes an airway tube having a first end and a second end, the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal against the laryngeal inlet of the patient, where a bracket, or plurality of brackets may be provided which extend part or full way across the opening of the cuff either from the distal end opening, the proximal end opening or both to prevent downfolding of the epiglottis and occlusion of the airway. The bracket(s) not only prevent occlusion of the airway but also provide strength to the cuff. The bracket(s) may in one alternative extend from the proximal end opening, in another alternative from the distal end opening, in another alternative the bracket(s) may extend across the full length of the opening. The bracket(s) may simply extend across the opening, or in the alternative may be the full height of the opening and contact the back of the opening. The bracket(s) may further be provided with notches or cut outs in their front face surface such that in the event that the epiglottis comes to rest on the bracket(s) the flow of air between the bracket is not effected such that there are no turbulent effects. Preferably the bracket (s) are formed from a substantially rigid material so that they support the weight of the epiglottis rather than flexing which might result in the occlusion of the airway if the bracket(s) flex under the weight of the epiglottis.

In a further alternative a portion of hard plastics material may be provided at the distal opening of the cuff to strengthen the tip of the cuff and to act as a flow director.

According to a seventh aspect of the present invention there is provided an airway device for human or animal use, the device includes an airway tube having a first end and a second end, the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal against the laryngeal inlet of the patient further comprising an inflatable back cuff, preferably the inflatable back cuff is located on the back dorsal portion of the cuff and when deflated is flush with the surface of the back dorsal portion of the cuff. This arrangement means that the upper surface of the inflatable cuff remains as rigid as the dorsal portion of the laryngeal cuff. The inflatable back cuff acts as a gap filler to ensure a seal between the front face of the cuff and the laryngeal inlet to counteract for any inter species variables such that the device is inhibited from any possible rotation when in situ in the patient. Preferably the inflatable back cuff has a defined perimeter so that it is adapted to inflate in substantially a single direction so there is no substantial change in the shape of the front face of the laryngeal cuff which forms the seal on and around the laryngeal inlet of the patient. Any inflation line provided is arranged such that it does not impede the gas flow to the patient. Preferably the inflatable back cuff is formed from a material with a Shore hardness of less than 20 on the A scale, more preferably less than 10 on the A scale.

Again it should be made clear that the features which are described above which include but are not limited to the shoulder, the raised portion, the angled tip of the laryngeal cuff, the annular flanges around the tip of the laryngeal cuff, the ribs on the airway tube, the mesh, the perforated plate, the skeleton formation, the brackets, the inflatable back cuff, the portion of hard plastics material, the blade like tip and the scallop or concave portion can all be used individually from each other in separate embodiments of the invention and that some features are shown and described in combination with other features is not intended to be limiting and it is intended that each feature can be used independently from any of the other features and also in combination with any or all of the other features described herein including but not limited to those listed above.

Features of the various aspects and embodiments described are intended to be interchangeable and not intended to be limited to the specific examples only in isolation.

BRIEF DESCRIPTION OF THE DRAWINGS

The invention will now be described, by way of example only, with reference to the accompanying drawings in which:

FIG. 41 is a top view of an airway device according to a fourteenth embodiment of the present invention;

FIG. 42 is a side view of an airway device according to a fourteenth embodiment of the present invention;

FIG. 43 is a bottom view of an airway device according to a fifteenth embodiment of the present invention;

FIG. 44 is a bottom view of an airway device according to a sixteenth embodiment of the present invention;

FIG. 82 is a top perspective view of an airway device according to a twenty-eighth embodiment of the present invention;

FIG. 83 is a bottom perspective view of an airway device according to a twenty-eighth embodiment of the present invention;

FIG. 84 is a top view of an airway device according to a twenty-ninth embodiment of the present invention.

FIG. 85 is a side view of an airway device according to a twenty-ninth embodiment of the present invention.

FIG. 86 is a bottom view of an airway device according to a twenty-ninth embodiment of the present invention.

FIG. 87 is a top perspective view of an airway device according to a twenty-ninth embodiment of the present invention.

FIG. 88 is a bottom perspective view of an airway device according to a twenty-ninth embodiment of the present invention.

FIG. 91 is a top view of an airway device according to a thirtieth embodiment of the present invention.

FIG. 92 is a side view of an airway device according to a thirtieth embodiment of the present invention.

FIG. 93 is a bottom view of an airway device according to a thirtieth embodiment of the present invention.

FIG. 94 is a top perspective view of an airway device according to a thirtieth embodiment of the present invention.

FIG. 95 is a bottom perspective view of an airway device according to a thirtieth embodiment of the present invention.

DESCRIPTION OF PREFERRED EMBODIMENT

Figure 1:
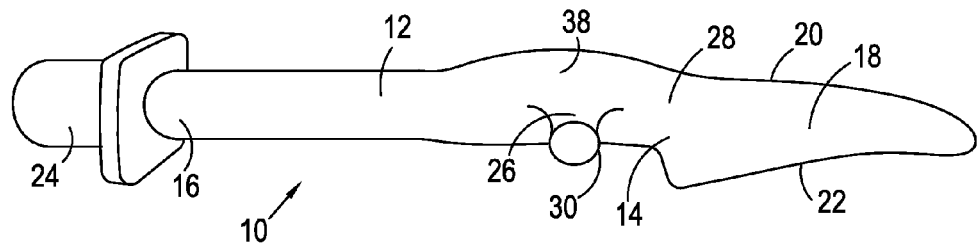
FIG. 1 is a side view of an airway device according to a first embodiment of the present invention.
Figure 2:
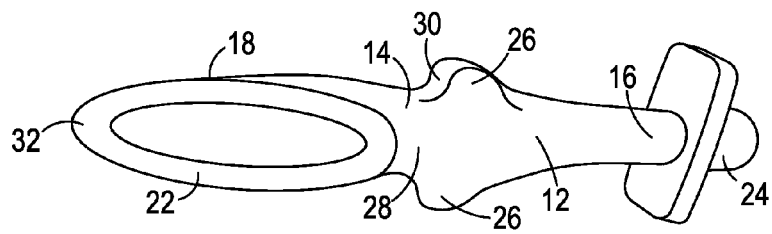
FIG. 2 is a bottom perspective view of an airway device according to a first embodiment of the present invention.
Figure 3:
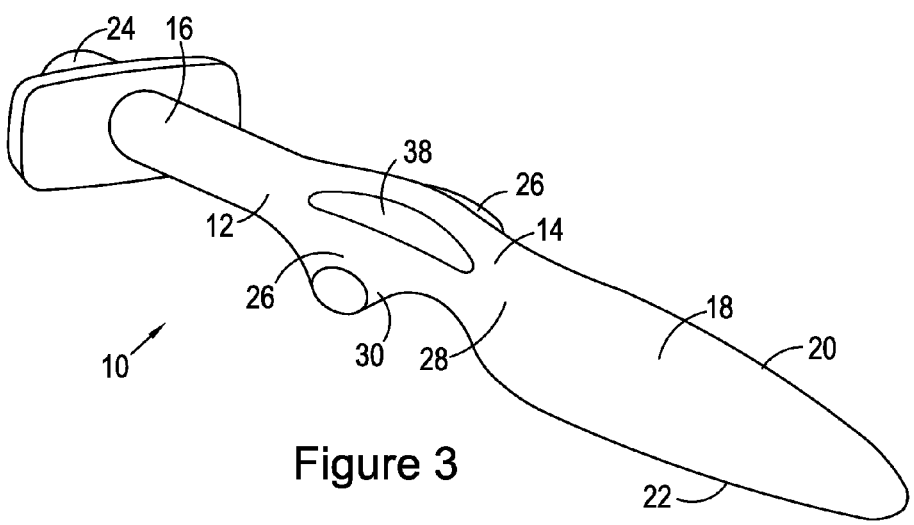
FIG. 3 is a top perspective view of an airway device according to a first embodiment of the present invention.

FIGS. 1 to 3 illustrate a first embodiment of an airway device according to the present invention. The airway device 10 has an airway tube 12 with a first end 14 and a second end 16. The first end 14 of the airway tube 12 is surrounded by a laryngeal cuff 18. The laryngeal cuff 18 has a back dorsal portion 20 and a front face portion 22. The front face portion 22 is shaped to form an anatomical fit over the laryngeal inlet of a human or animal patient, and to form a seal with the laryngeal inlet of the patient. The second end 16 of the airway tube is fitted with a connector 24 such that the second end 16 of the airway tube 12 can be connected to the relevant gas supply. The airway device 10 also has a shoulder 26. The shoulder 26 is used to prevent over-insertion of the airway device 10. The shoulder 26 is located laterally or perpendicular to the direction of the airflow, and thus the airway tube 12. The shoulder 26 is located just above the neck 28 of the airway device 10 where the laryngeal cuff 18 appears to join the airway tube 12 at the second end 14. The shoulder 26 is used to create a point of contact between the airway device 10 and the faucial pillars located at the back of the mouth of a human or animal patient. This thus creates a positive stopping feature that in use prevents the shoulder 26 going forward beyond the faucial pillars of the patient to prevent over-insertion of the airway device 10.

In order to create a positive stopping feature, the width of the shoulder 26 needs to be substantially larger than the width of the faucial pillars, but less than the internal width of the back of the mouth. This will result in a definite and positive stopping feature to permit the device to be inserted into the correct position, and not rub against the inside of the mouth, such that there is no irritation to the mouth of the patient during use. The shoulder 26 is shaped such that it is substantially perpendicular to the direction of airflow and thus the airway tube 12. This maximizes the resistance of the shoulder 26, to bypass the elasticity of the faucial pillar tissues. In use, when the airway device 10 is inserted into the patient, the shoulder 26 will eventually impact against the faucial pillars of the patient. After impacting the faucial pillars, the shoulder 26 will naturally bounce back a little way and will rest away from being in direct contact with the faucial pillar tissues, thus not causing any trauma. In order to further minimize contact, and thus reduce trauma around the faucial pillar tissues, the leading edge 30 of the shoulder 26 may be vertically angled.

In the embodiment illustrated in FIGS. 1 to 3 the shoulder 26 is formed integrally with the airway device 10. In the alternative, the shoulder 26 can be separately attached through using combined materials welding process techniques or by using various bonding or mechanical attachment methods to the airway tube 12. The shoulder 26 is free from sharp edges and made of a material, such as a polymeric or other plastics material, with a Shore hardness between 80 and 000 on the A scale. Making the shoulder 26 from a soft material will also act to minimize any possible trauma that could result from the shoulder of the airway device 10 coming into sudden contact with the faucial pillar to provide the positive stop feature. Further in the alternative the shoulder may include an inflatable region. Yet further in the alternative the shoulder may have a hard core covered in a softer skin to minimize trauma yet provide a rigid structure, particularly in the case of stronger animals such a horses.

The shoulder 26 acts as a stop mechanism, ensuring that small laryngeal cuffs on airway devices will be correctly positioned within the larynx of the patient and not go beyond to cause any potential damage to the patient in the trachea of with the vocal chords.

In addition the neck 28 of the airway device should ideally be in a close fitting relationship with the sides of the faucial pillars in order to provide increased resistance to the device being rotated in use.

The airway device 10 is further provided with a raised portion 38, which is formed from a material, such as a polymeric or other plastics material with a Shore hardness between 80 and 000 on the A scale. The raised portion 38 is located on the airway tube 12 above and extending just behind the shoulder 26 towards the second end 16 of the airway tube. When in situ in a patient, the raised portion 38 corresponds to location of the cavity of the upper mouth arch of the patient called the palatoglossal arch. The raised portion 38 aids in preventing over-insertion of the airway device 10 by being adapted to locate in the cavity of the palatoglossal arch due to the contouring of the raised portion and provides resistance from being moved beyond this position. The raised portion 38 is not meant to be in constant contact with the palatoglossal arch but simply to locate into this cavity to prevent over-insertion and resist movement of the device when in situ. The raised portion 38 also prevents unwanted rotation and any movement generally of the airway device 10. In alternative embodiments of the airway device for particular animal species it may be necessary to provide a narrowed and alternatively shaped raised portion to avoid contact with the teeth of the animal patient. In the embodiment shown in FIGS. 1 to 3 the raised portion 38 is a bulge, however in alternative embodiments the raised portion 38 may be a plurality of ribs or fins. In the case of ribs or fins the Shore hardness of the material should be between 80 and 000 on the A scale. In the case of a bulge the Shore hardness of the material should also be between 40 and 000 on the A scale. Further in the alternative the raised portion may include an inflatable region. Yet further in the alternative the raised portion may have a hard core covered in a softer skin to minimize trauma yet provide a rigid structure, particularly in the case of stronger animals such a horses.

Figure 4:
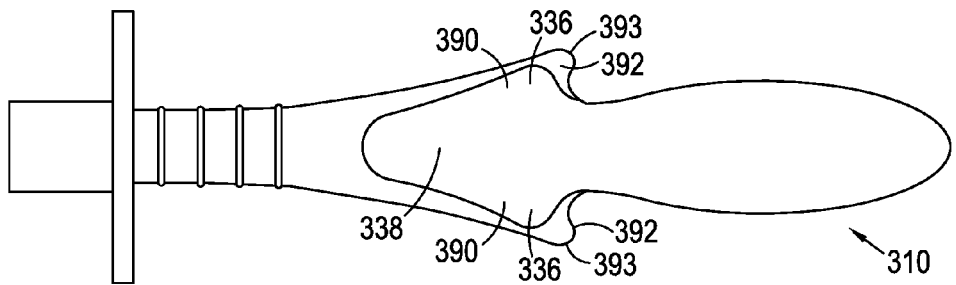
FIG. 4 is a top view of an airway device according to a second embodiment of the present invention.
Figure 5:
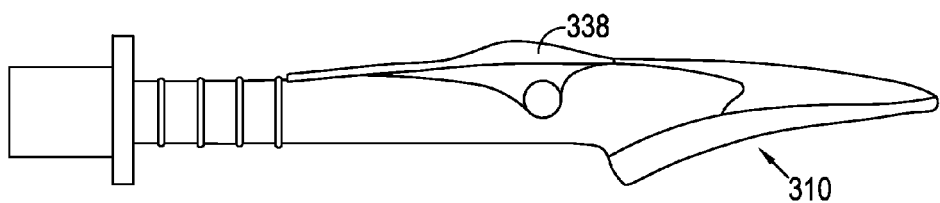
FIG. 5 is a side view of an airway device according to a second embodiment of the present invention.
Figure 6:
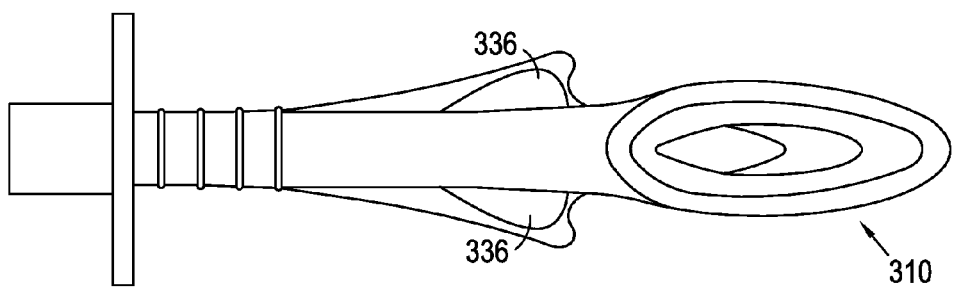
FIG. 6 is a bottom view of an airway device according to a second embodiment of the present invention.
Figure 7:
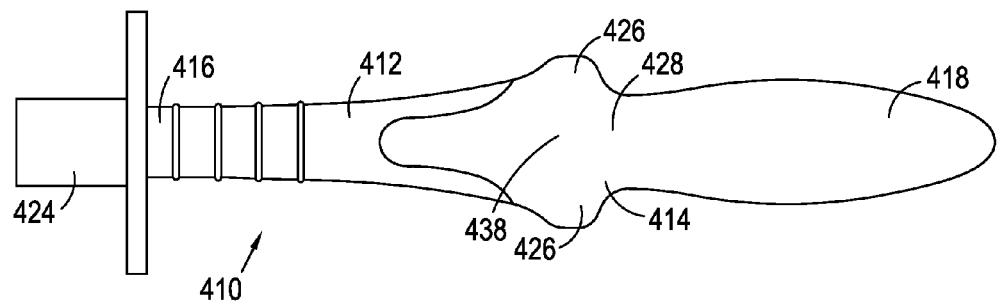
FIG. 7 is a top view of an airway device according to a third embodiment of the present invention.
Figure 8:
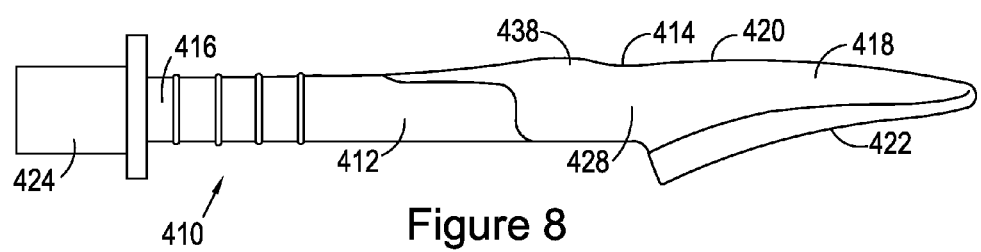
FIG. 8 is a side view of airway device according to a third embodiment of the present invention.
Figure 9:
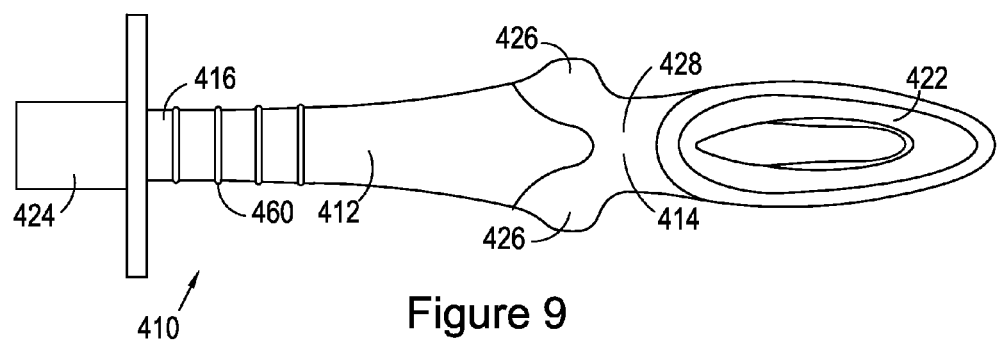
FIG. 9 is a bottom view of an airway device according to a third embodiment of the present invention.
Figure 10:
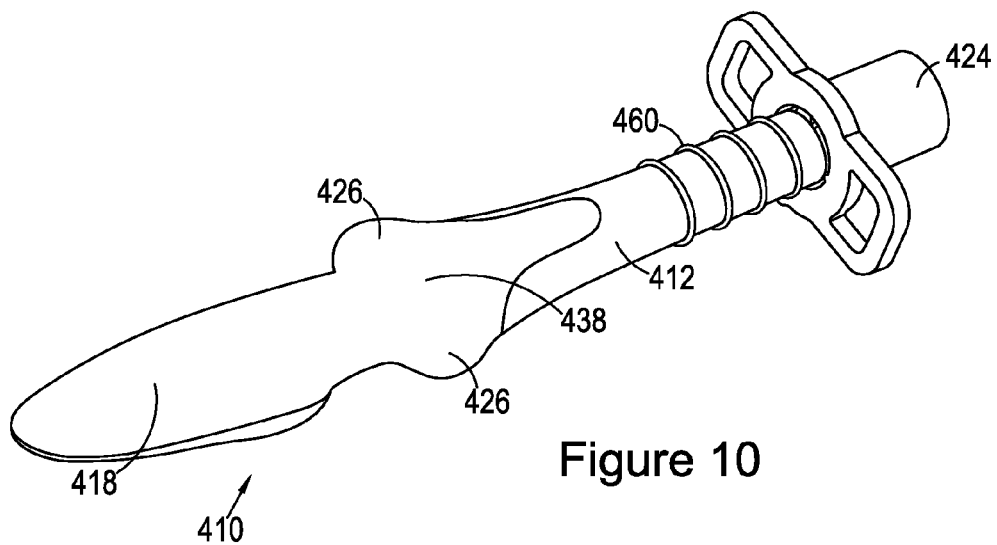
FIG. 10 is a top perspective view of an airway device according to a third embodiment of the present invention.
Figure 11:
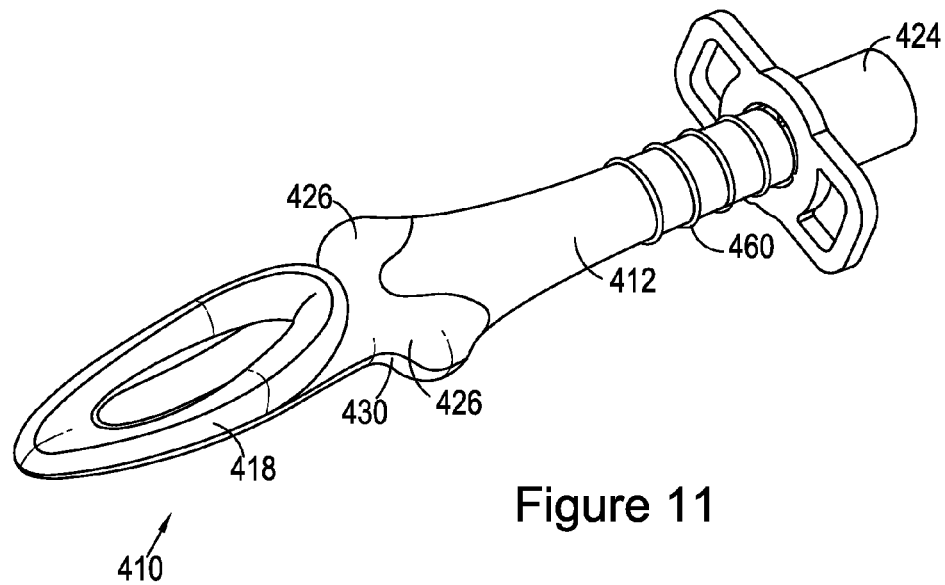
FIG. 11 is a bottom perspective view of an airway device according to a third embodiment of the present invention.

FIGS. 4 to 6 illustrate a further embodiment of an airway device 310. In the embodiment shown the shoulders 336 are formed with a hard 390 and a soft covering 392. The Shore hardness of the material of the hard core 390 should be between 80 and 000 on the A scale and the Shore hardness of the material of the very soft covering should be between 40 and 000 on the A scale. In an alternative embodiment the shoulders 336 are inflatable and the raised portion 338 is also inflatable. In addition for certain species the shoulders are provided with forward facing protrusions 393. The forward facing protrusions 393 are located on the leading face of the shoulder 336. The forward facing protrusions 393 are adapted to locate into anatomical cavities which are present in dogs, for example, after the pharyngeal arches. In general dogs have a very wide pharyngeal arch as they are designed to consume large volumes of food very rapidly. The forward facing shoulder protrusions 393 being adapted to fit into the anatomical cavity region to make the whole airway device 310 fit more securely and not easily by-pass the pharyngeal arches. It is worth bearing in mind that the pharyngeal arches are particularly elastic in dogs.

FIGS. 7 to 11 illustrate another embodiment of an airway device 410. The airway device 410 has an airway tube 412 with a first end 414 and a second end 416. The first end 414 of the airway tube 412 is surrounded by a laryngeal cuff 418. The laryngeal cuff 418 has a back dorsal portion 420 and a front face portion 422. The front face portion 422 is shaped to form an anatomical fit over the laryngeal inlet of a human or animal patient, and to form a seal with the laryngeal inlet of the patient. The second end 416 of the airway tube is fitted with a connector 424 such that the second end 416 of the airway tube 412 can be connected to the relevant gas supply. The airway device 410 also has a shoulder 426. The shoulder 426 is used to prevent over-insertion of the airway device 410. The shoulder 426 is located laterally to the direction of the airflow, and thus the airway tube 412. The shoulder 426 is located just above the neck 428 of the airway device 410 where the laryngeal cuff 418 appears to join the airway tube 412 at the second end 414 thereof. The shoulder 426 is used to create a point of contact between the airway device 410 and the faucial pillars located at the back of the mouth of a human or animal patient. This thus creates a positive stopping feature that in use prevents the shoulder 426 going forward beyond the faucial pillars of the patient to prevent over-insertion of the airway device 410. In order to further minimize contact and thus trauma around the faucial pillar tissues, the leading edge 430 of the shoulder 426 may be vertically angled.

In the embodiment illustrated in FIGS. 7 to 11 the shoulder 426 is formed integrally with the airway device 410. In the alternative, the shoulder 426 can be separately attached through using combined materials welding process techniques or by using various bonding or mechanical attachment methods to the airway tube 412. Further in the alternative the shoulder may include an inflatable region. Yet further in the alternative the shoulder may have a hard inner core covered in a softer skin to minimize trauma yet provide a rigid structure, particularly in the case of stronger animals such a horses.

The airway device 410 is further provided with a raised portion 438, which is located on the airway tube 412 above and extending just behind the shoulder 426 towards the second end 416 of the airway tube. When in situ in a patient, the raised portion 438 corresponds to location of the cavity of the upper mouth arch of the patient called the palatoglossal arch. In the embodiment shown in FIGS. 7 to 11 the raised portion 438 is a bulge, however in alternative embodiments the raised portion 438 may be a plurality of ribs or fins. Further in the alternative the raised portion may include an inflatable region. Yet further in the alternative the raised portion may have a hard core covered in a softer skin to minimize trauma yet provide a rigid structure, particularly in the case of stronger animals such as horses.

The airway device 410 is also further provided with a plurality of ribs 460 near the second end 416 of the airway tube 412 near to the connector 424. The ribs 460 provide a friction point for tying the device around an animal's head as it is generally not possible to use tape as in humans due to the animal's fur.

Figure 12:
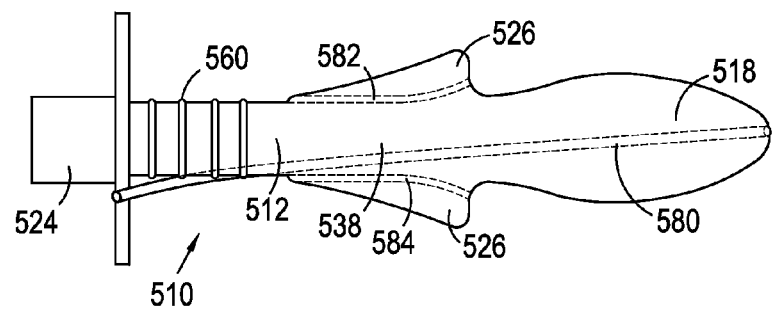
FIG. 12 is a top view of an airway device according to a fourth embodiment of the present invention.

FIG. 12 illustrates another embodiment of an airway device 510. In addition to the standard features of an airway tube 512, laryngeal cuff 518 and connector portion 524, the airway device 510 is provided with a shoulder 526 and a raised portion 538 and a plurality of ribs 560 as discussed above in relation to other embodiments of the present invention. The main additional features associated with the embodiment of the airway device illustrated in FIG. 12 is the presence of an oesophageal gastric channel 580 and two suction channels 582, 584. The suction channels 582, 584 operate are provided to assist the removal of fluids which may build up at the back of the mouth. The suction channels 582, 584 may be integral with or separate from the oesophageal gastric channel 580 if one is provided. In the alternative an oesophageal gastric channel may simply be provided without any additional suction channels.

Figure 13:
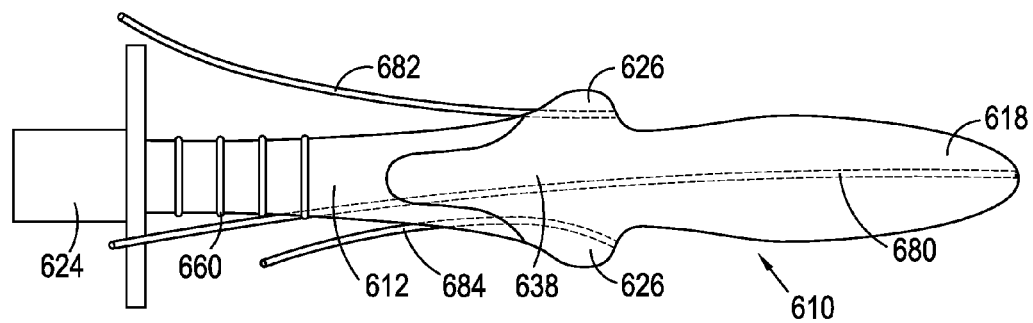
FIG. 13 is a top view of an airway device according to a fifth embodiment of the present invention.

FIG. 13 illustrates another embodiment of an airway device 610. In addition to the standard features of an airway tube 612, laryngeal cuff 618 and connector portion 624, the airway device 610 is provided with a shoulder 626 and a raised portion 638 and a plurality of ribs 660 as discussed above in relation to other embodiments of the present invention. The main additional features associated with the embodiment of the airway device illustrated in FIG. 13 is the presence of an oesophageal gastric channel 680 and two suction channels 682, 684. The suction channels 682, 684 operate are provided to assist the removal of fluids which may build up at the back of the mouth. The suction channels 682, 684 may be integral with or separate from the oesophageal gastric channel 680 if one is provided. The suction channels 682, 684 in FIG. 13 extend beyond the shoulder portion towards the connector end of the airway device 610. Again in the alternative an oesophageal gastric channel may simply be provided without any additional suction channels.

Figure 14:
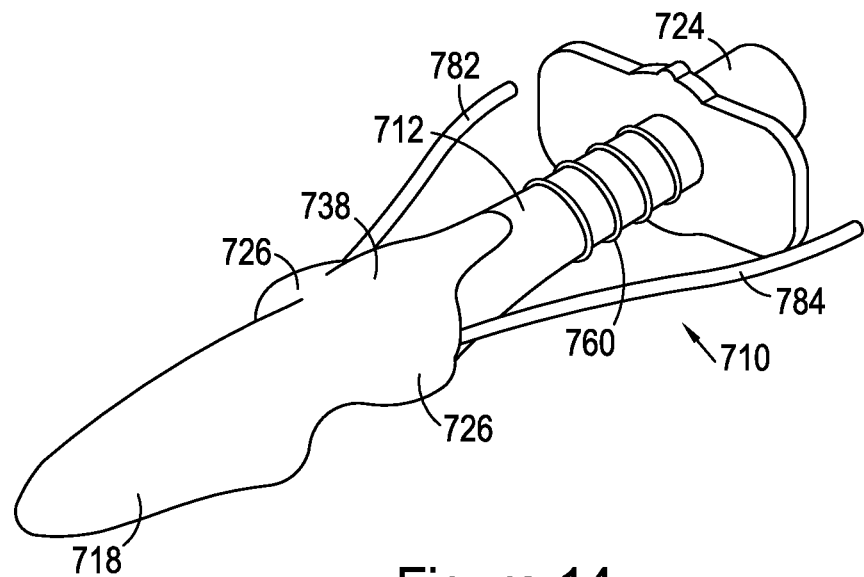
FIG. 14 is a top perspective view of an airway device according to a sixth embodiment of the present invention.
Figure 15:
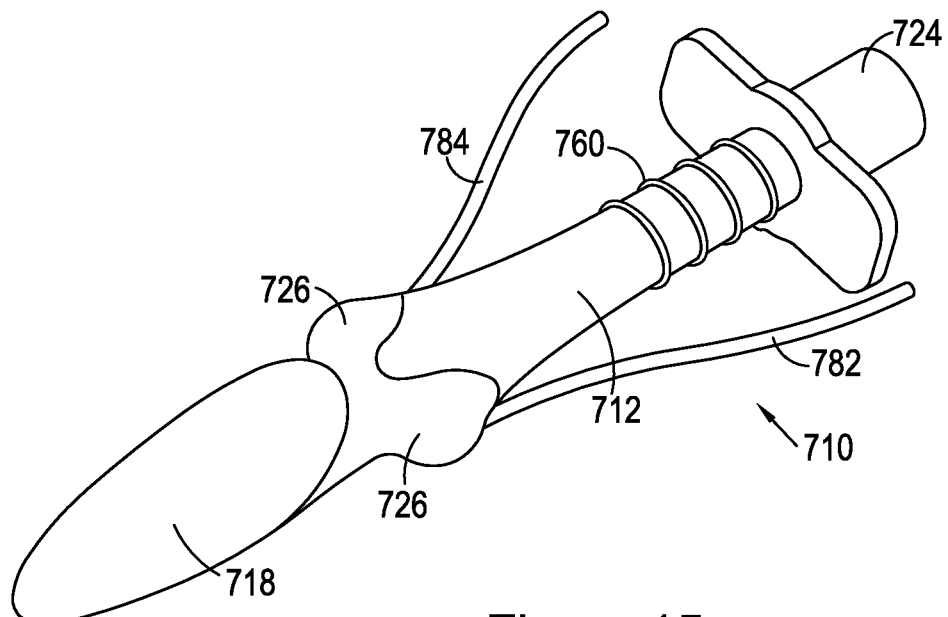
FIG. 15 is a bottom perspective view of an airway device according to a sixth embodiment of the present invention.
Figure 19:
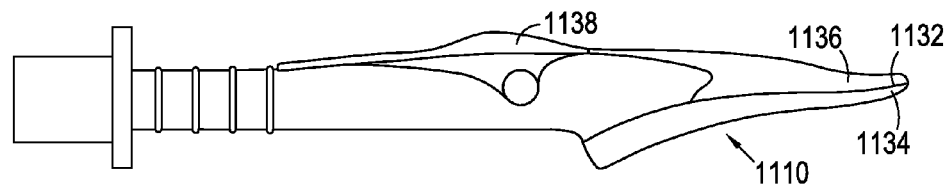
FIG. 19 is a side view of an airway device according to an eighth embodiment of the present invention.
Figure 20:
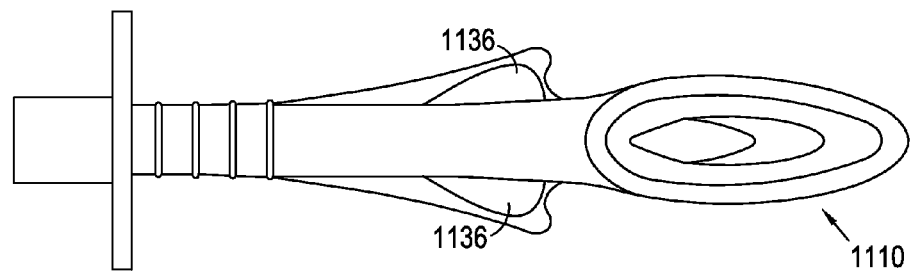
FIG. 20 is a bottom view of an airway device according to an eighth embodiment of the present invention.
Figure 21:
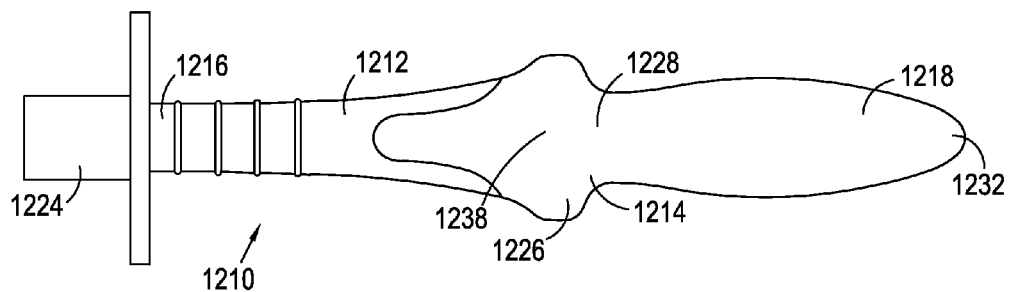
FIG. 21 is a top view of an airway device according to a ninth embodiment of the present invention.
Figure 22:
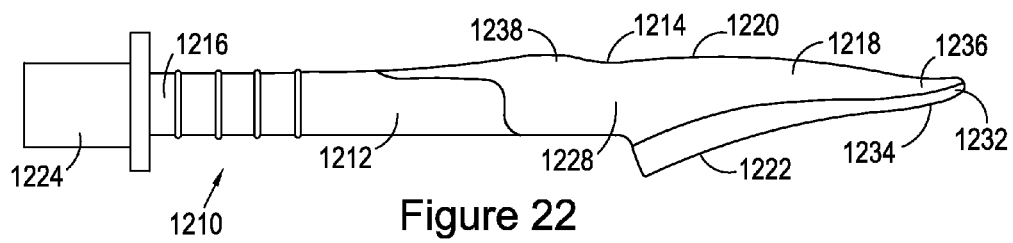
FIG. 22 is a side view of an airway device according to a ninth embodiment of the present invention.
Figure 23:
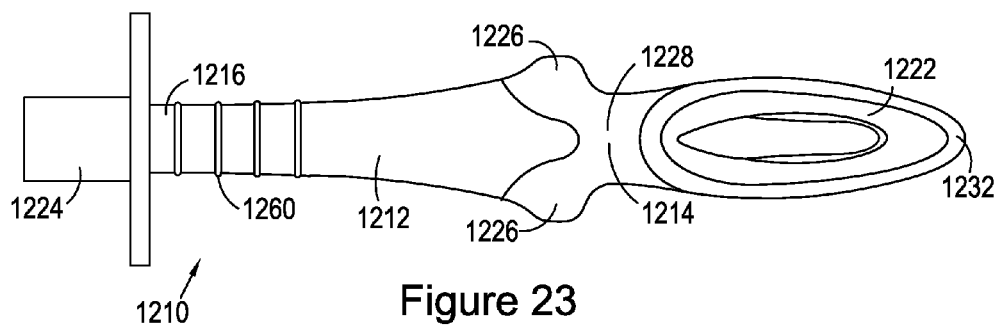
FIG. 23 is a bottom view of an airway device according to a ninth embodiment of the present invention.
Figure 24:
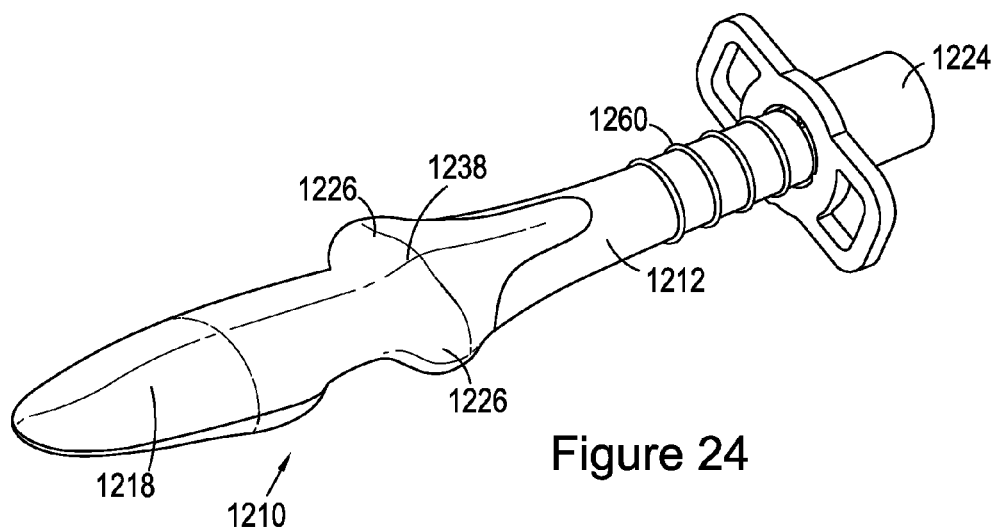
FIG. 24 is a top perspective view of an airway device according to a ninth embodiment of the present invention.
Figure 25:
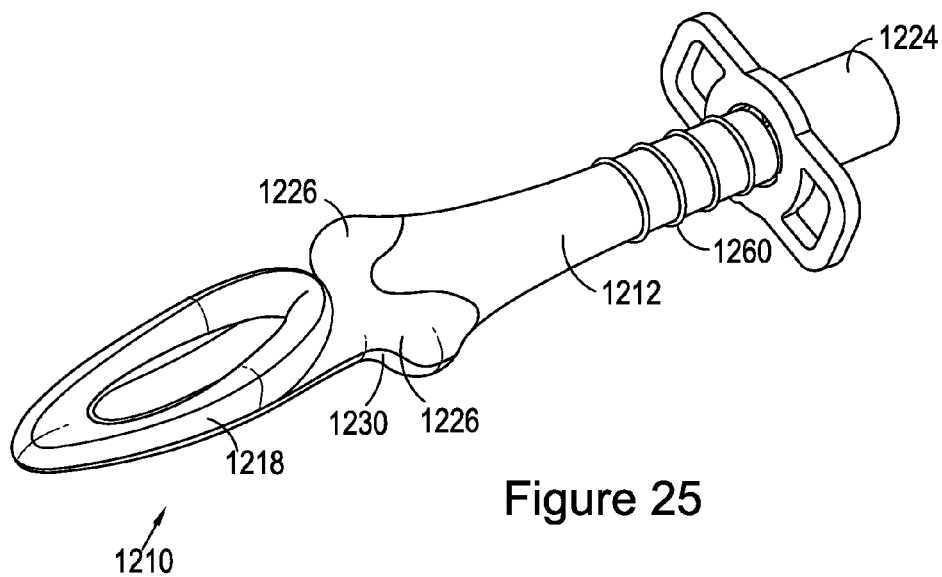
FIG. 25 is a bottom perspective view of an airway device according to a ninth embodiment of the present invention.

FIGS. 14 and 15 illustrate another embodiment of an airway device 710. In addition to the standard features of an airway tube 712, laryngeal cuff 718 and connector portion 724, the airway device 710 is provided with a shoulder 726 and a raised portion 738 and a plurality of ribs 760 as discussed above in relation to other embodiments of the present invention. The main additional features associated with the embodiment of the airway device illustrated in FIGS. 19 and 20 are the presence of two suction channels 782, 784. The suction channels 782, 784 operate are provided to assist the removal of fluids which may build up at the back of the mouth. The suction channels 782, 784 may be integral with or separate from the oesophageal gastric channel (not shown) if one is provided. The suction channels 782, 784 in FIGS. 14 and 15 extend beyond the shoulder portion towards the connector end of the airway device 710.

Figure 16:
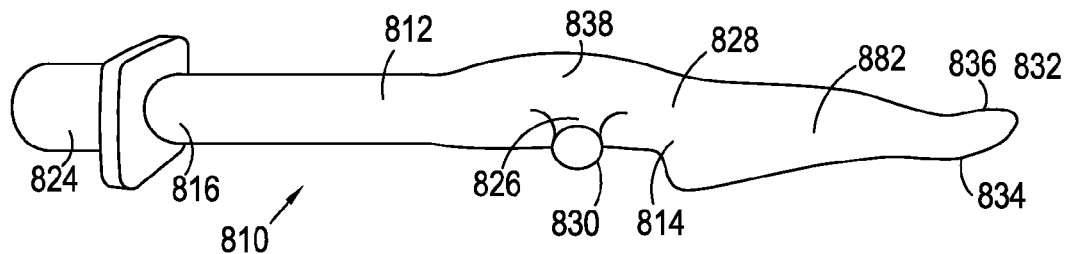
FIG. 16 is a side view of an airway device according to a seventh embodiment of the present invention.
Figure 17:
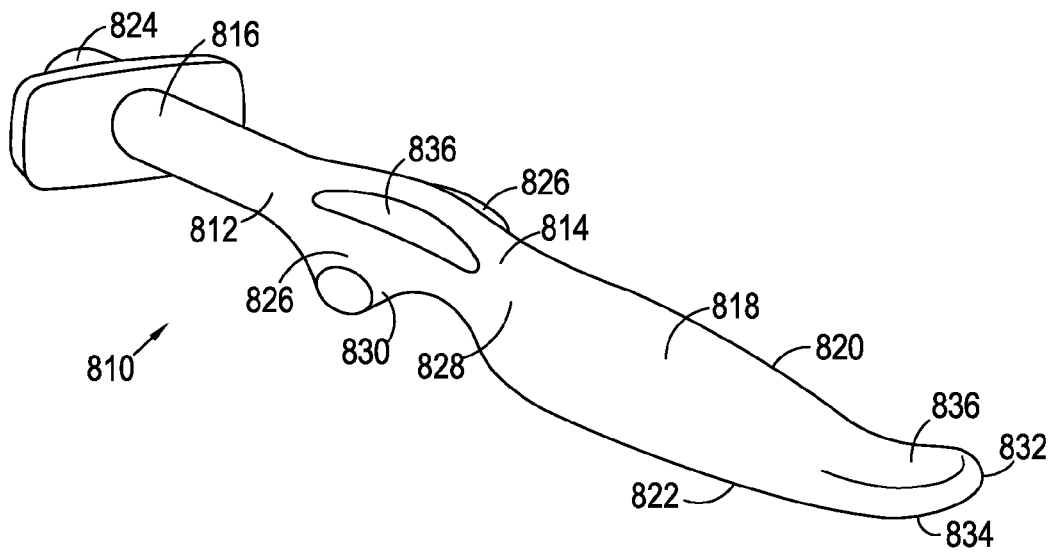
FIG. 17 is a top perspective view of an airway device according to a seventh embodiment of the present invention.

FIGS. 16 and 17 illustrate an eighth embodiment of an airway device according to the present invention. The airway device 810 has an airway tube 812 with a first end 814 and a second end 816. The first end 814 of the airway tube 812 is surrounded by a laryngeal cuff 818. The laryngeal cuff 818 has a back dorsal portion 820 and a front face portion 822. The front face portion 822 is shaped to form an anatomical fit over the laryngeal inlet of a human or animal patient, and to form a seal with the laryngeal inlet of the patient. The second end 816 of the airway tube is fitted with a connector 824 such that the second end 816 of the airway tube 812 can be connected to the relevant gas supply. The airway device 810 also has a shoulder 826. The shoulder 826 is used to prevent over-insertion of the airway device 810. The shoulder 826 is located laterally or perpendicular to the direction of the airflow, and thus the airway tube 812. The shoulder 826 is located just above the neck 828 of the airway device 810 where the laryngeal cuff 818 appears to join the airway tube 812 at the second end 814 thereof. The shoulder 826 is used to create a point of contact between the airway device 810 and the faucial pillars located at the back of the moth of a human or animal patient. This thus creates a positive stopping feature that in use prevents the shoulder 826 going forward beyond the faucial pillars of the patient to prevent over-insertion of the airway device 810. In order to further minimize contact and thus reduce trauma around the faucial pillar tissues, the leading edge 830 of the shoulder 826 may be vertically angled.

In the embodiment illustrated in FIGS. 16 and 17 the shoulder 826 is formed integrally with the airway device 810. In the alternative, the shoulder 826 can be separately attached through using combined materials welding process techniques or by using various bonding or mechanical attachment methods to the airway tube 812. Further in the alternative the shoulder may include inflatable region.

In order to further discourage over-insertion, the tip 832 of the laryngeal cuff 818 is angled upwards away from the horizontal plane of the laryngeal cuff 818. The tip 832 may be angled from 5° to 80°. The angle of the tip 832 has the effect of increasing the surface area of the tip 832. The tip 832 engages to seal with the top of the esophagus of the patient when the airway device 810 is correctly inserted. The larger tip 832 surface area creates some resistance with the top of the esophagus during insertion which would be felt by the clinician during insertion to determine that the airway 810 device has been correctly inserted. The tip is formed from materials of two different hardnesses. A soft material is used for the front face portion of the tip 834 and a harder material is used for the rear dorsal portion of the tip 836. This results in a tip which has strength to prevent the tip folding over on itself and soft to prevent damage to the esophagus upon contact.

The airway device 810 is further provided with a raised portion 838, which is located on the airway tube 812 above and extending just behind the shoulder region 826 towards the second end 816 or the airway tube. When in situ in a patient, the raised portion 838 corresponds to location of the cavity of the upper mouth arch of the patient called the palatoglossal arch. In the embodiment shown in FIGS. 16 and 17 the raised portion 838 is a bulge, however in alternative embodiments the raised portion 838 may be a plurality of ribs or fins. Further in the alternative the raised portion may include an inflatable region.

Figure 18:
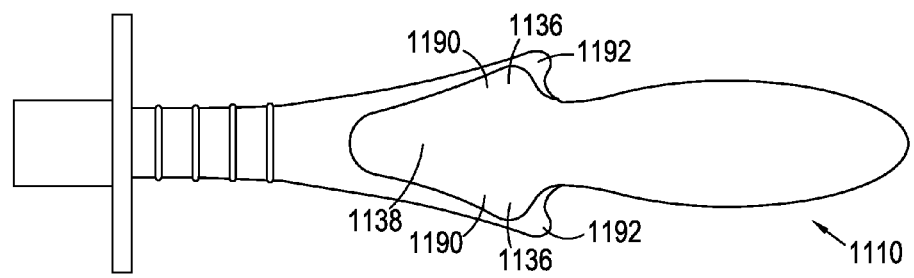
FIG. 18 is a top view of an airway device according to an eighth embodiment of the present invention.

FIGS. 18 to 20 illustrate a further embodiment of an airway device 1110. In the embodiment shown the shoulders 1136 are formed with a harder core 1190 and a very soft covering 1192. The Shore hardness of the material of the harder core 1190 should be between 80 and 000 on the A scale and the Shore hardness of the material of the very soft covering should be between 40 and 000 on the A scale. In an alternative embodiment the shoulders 1136 are inflatable and the raised portion 1138 is also inflatable.

Again in order to further discourage over-insertion, the tip 1132 of the laryngeal cuff 1118 is angled upwards away from the horizontal plane of the laryngeal cuff 1118. The tip 1132 may be angled from 5° to 80°. A soft material is used for the front face portion of the tip 1234 and a harder material is used for the rear dorsal portion of the tip 1236. This results in a tip which has strength to prevent the tip folding over on itself and soft to prevent damage to the esophagus upon contact.

FIGS. 21 to 25 illustrate another embodiment of an airway device 1210. The airway device 1210 has an airway tube 1212 with a first end 1214 and a second end 1216. The first end 1214 of the airway tube 1212 is surrounded by a laryngeal cuff 1218. The laryngeal cuff 1218 has a back dorsal portion 1220 and a front face portion 1222. The front face portion 1222 is shaped to form an anatomical fit over the laryngeal inlet of a human or animal patient, and to form a seal with the laryngeal inlet of the patient. The second end 1216 of the airway tube is fitted with a connector 1224 such that the second end 1216 of the airway tube 1212 can be connected to the relevant gas supply. The airway device 1210 also has a shoulder 1226. The shoulder 1226 is used to prevent over-insertion of the airway device 1210. The shoulder 1226 is located laterally or perpendicular to the direction of the airflow, and thus the airway tube 1212. The shoulder 1226 is located just above the neck 1228 of the airway device 1210 where the laryngeal cuff 1218 appears to join the airway tube 1212 at the second end 1214. The shoulder 1226 is used to create a point of contact between the airway device 1210 and faucial pillars located at the back of the mouth of a human or animal patient. This thus creates a positive stopping feature that in use prevents the shoulder 1226 going forward beyond the faucial pillars of the patient to prevent over-insertion of the airway device 1210. In order to further minimize contact and thus trauma around the faucial pillar tissues, the leading edge 1230 of the shoulder 1226 may be vertically angled.

In the embodiment illustrated in FIGS. 21 to 25 the shoulder 1226 is formed integrally with the airway device 1210. In the alternative, the shoulder 1226 can be separately attached through using combined materials welding process techniques or by using various bonding or mechanical attachment methods to the airway tube 1212. Further in the alternative the shoulder may include an inflatable region. Yet further in the alternative the shoulder may have a hard inner core covered in a softer skin to minimize trauma yet provide a rigid structure, particularly in the case of stronger animals such as horses.

In order to further discourage over-insertion, the tip 1232 of the laryngeal cuff 1218 is angled upwards away from the horizontal plane of the laryngeal cuff 1218. The tip 1232 may be angled from 5° to 80°. The tip is formed from materials of two different harnesses. A soft material is used for the front face portion of the tip 1234 and a harder material is used for the rear dorsal portion of the tip 1236. This results in a tip which has strength to prevent the tip folding over on itself and soft to prevent damage to the esophagus upon contact.

The airway device 1210 is further provided with a raised portion 1238, which is located on the airway tube 1212 above and extending just behind the shoulder region 1226 towards the second end 1216 of the airway tube. When in situ in a patient, the raised portion 1238 corresponds to location of the cavity of the upper mouth arch of the patient called the palatoglossal arch. In the embodiment shown in FIGS. 21 to 25 the raised portion 1238 is a bulge, however in alternative embodiments the raised portion 1238 may be a plurality of ribs or fins. Further in the alternative the raised portion may include an inflatable region. Yet further in the alternative the shoulder portion may have a hard inner core covered in a softer skin to minimize trauma yet provide a rigid structure, particularly in the case of stronger animals such a horses.

The airway device 1210 is also further provided with a plurality of ribs 1260 near the second end 1216 of the airway tube 1212 near to the connector 1224. The ribs 1260 provide a friction point for tying the device around an animal's head as it is generally not possible to use tape as in humans due to the animal's fur.

Figure 26:
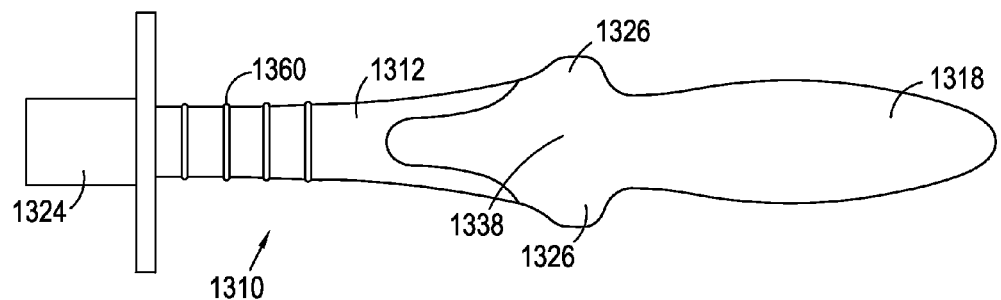
FIG. 26 is a top view of an airway device according to a tenth embodiment of the present invention.
Figure 27:
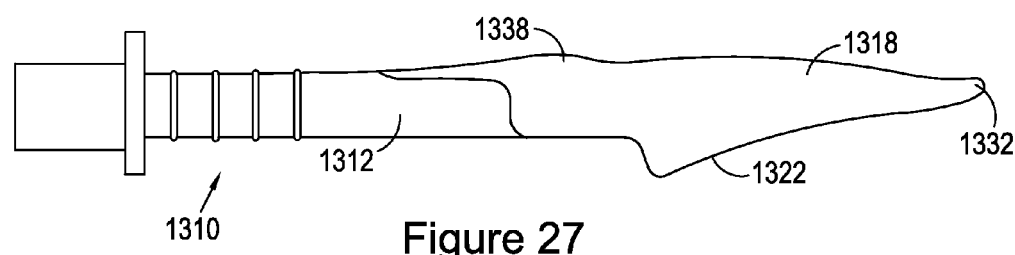
FIG. 27 is a side view of an airway device according to a tenth embodiment of the present invention.
Figure 28:
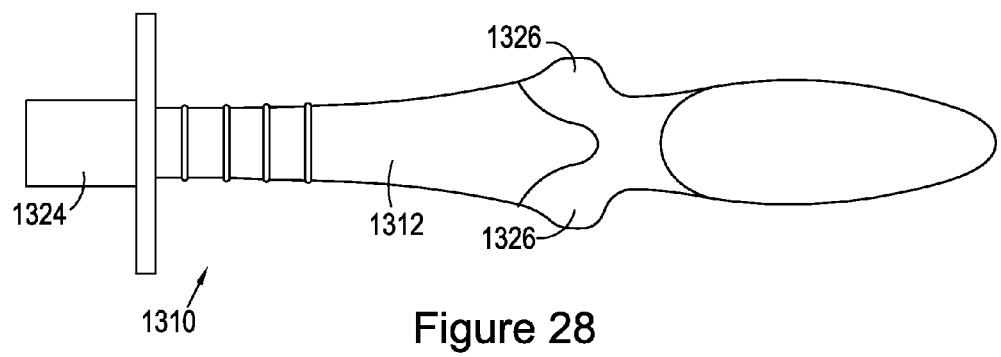
FIG. 28 is a bottom view of an airway device according to a tenth embodiment of the present invention.
Figure 29:
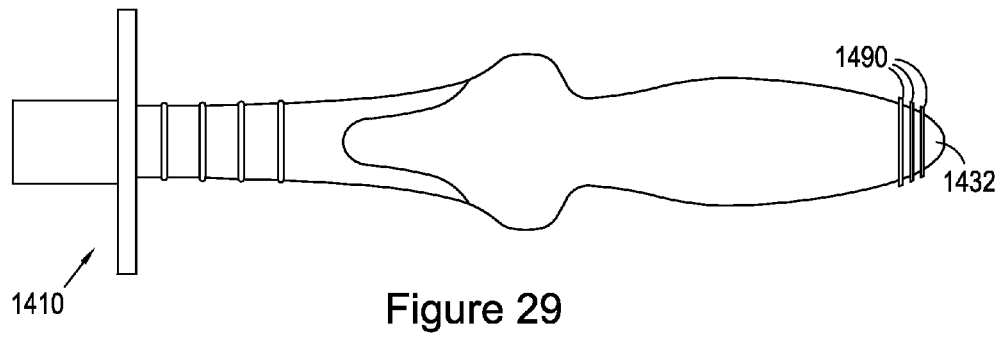
FIG. 29 is a top view of an airway device according to a eleventh embodiment of the present invention.
Figure 30:
FIG. 30 is a side view of an airway device according to a eleventh embodiment of the present invention.
Figure 31:
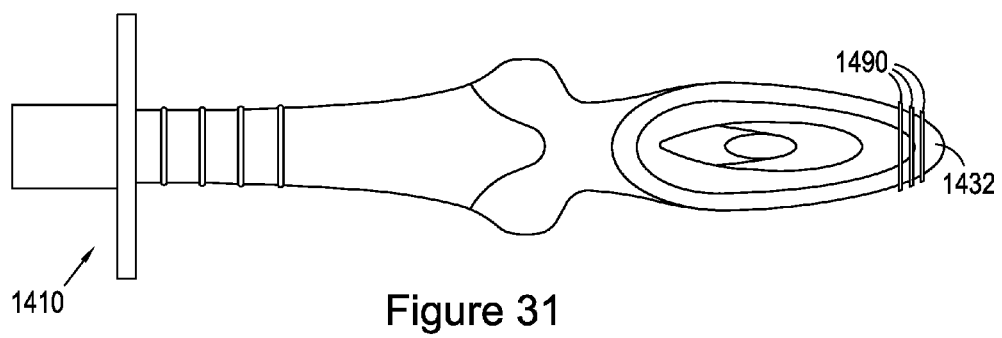
FIG. 31 is a bottom view of an airway device according to a eleventh embodiment of the present invention.
Figure 32:
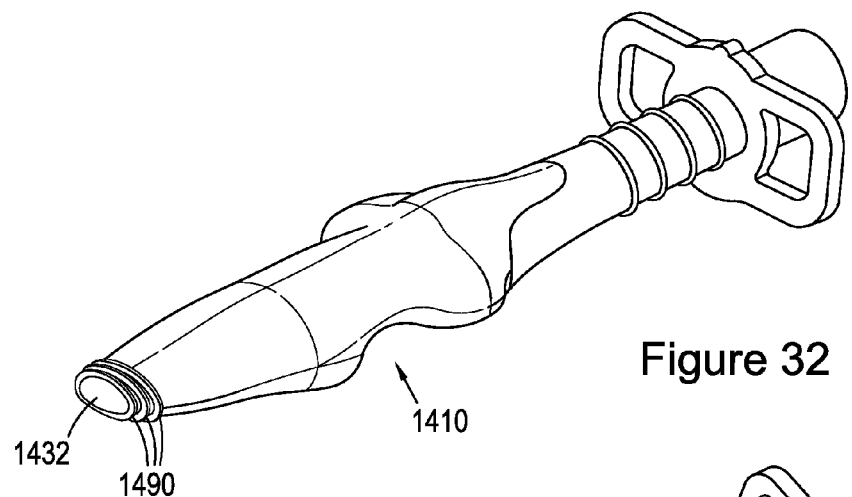
FIG. 32 is a bottom perspective view of an airway device according to a eleventh embodiment of the present invention.
Figure 33:
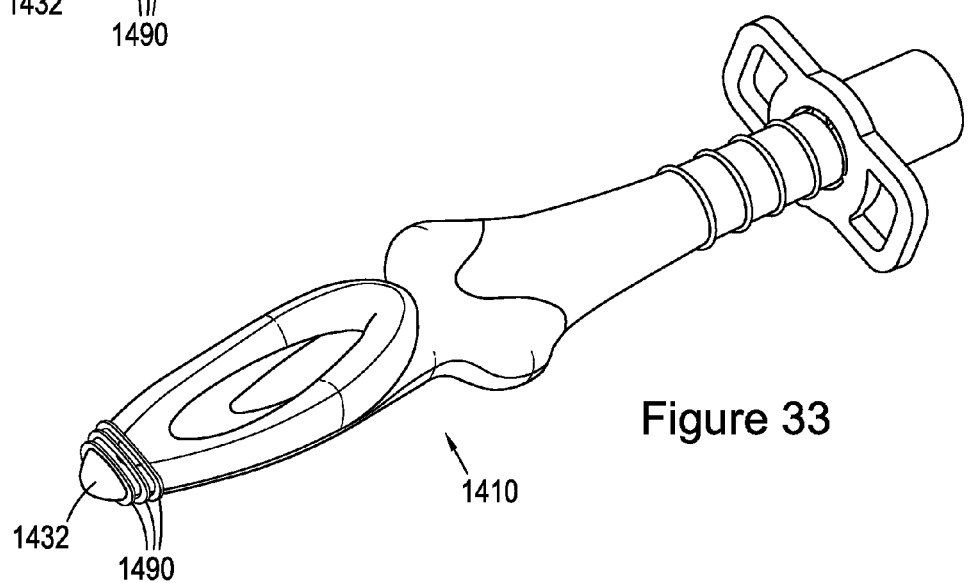
FIG. 33 is a top perspective view of an airway device according to a eleventh embodiment of the present invention.
Figure 34:
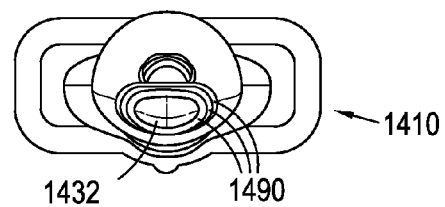
FIG. 34 is an end view of an airway device according to a eleventh embodiment of the present invention.
Figure 35:
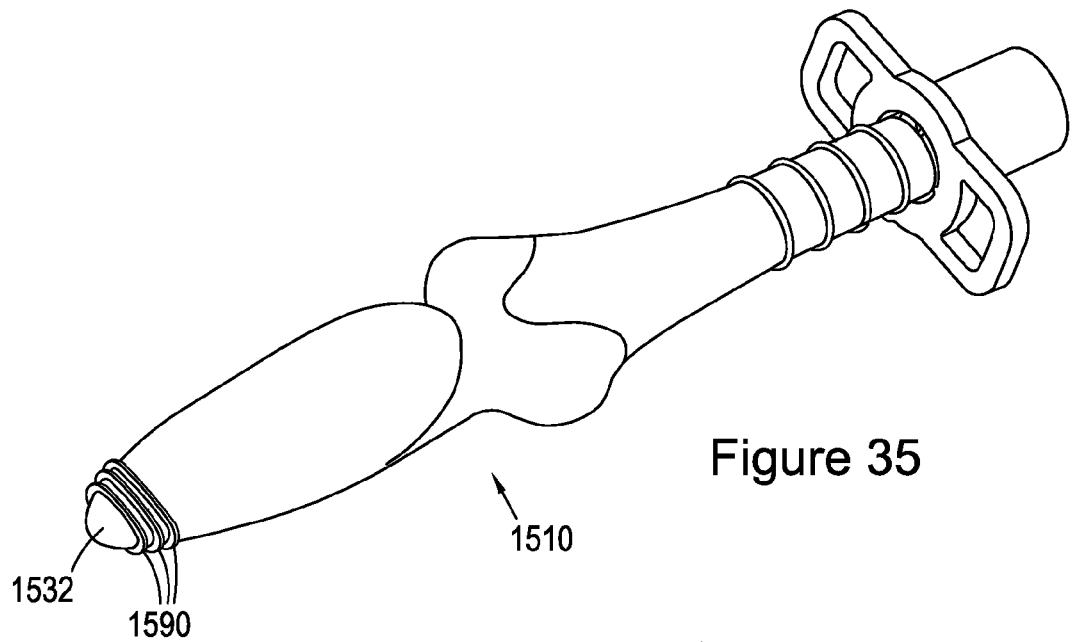
FIG. 35 is a bottom perspective view of an airway device according to a twelfth embodiment of the present invention.
Figure 36:
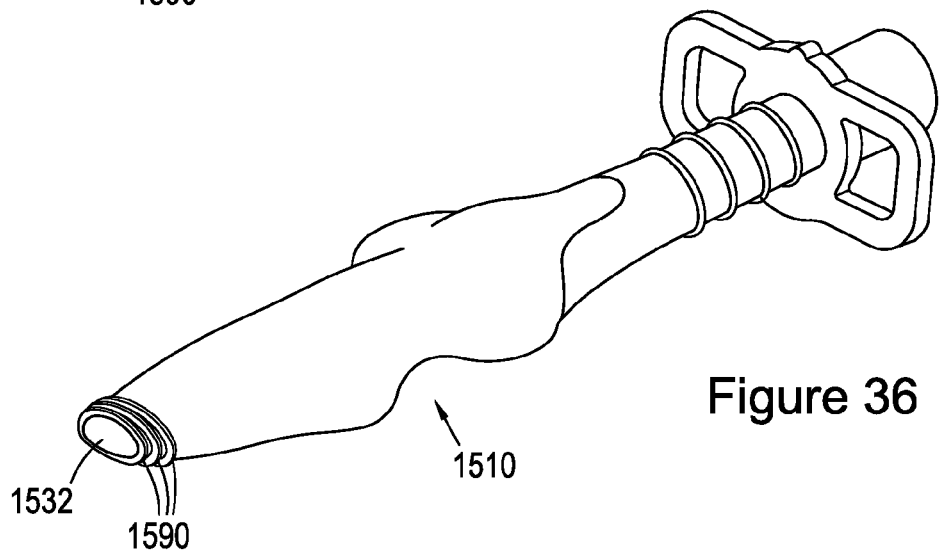
FIG. 36 is a top perspective view of an airway device according to a twelfth embodiment of the present invention.
Figure 37:
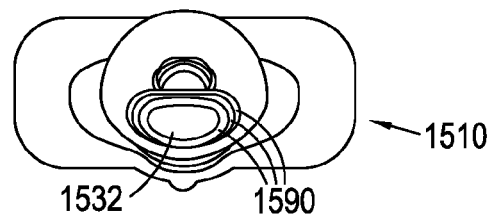
FIG. 37 is an end view of an airway device according to a twelfth embodiment of the present invention.

FIGS. 26 to 28 illustrate another embodiment of an airway device 1310. This is essentially a similar embodiment to that illustrated in FIGS. 21 to 25 with a less detailed cuff 1318.

FIGS. 29 to 34 and FIGS. 35 to 37 illustrate two further embodiments of an airway device 1410 and 1510 respectively. The tip 1432, 1532 of the laryngeal cuff in these embodiments is provided with a series of annular flange sealing portions 1490, 1590. The annular flange sealing portions 1490, 1590 are provided for improved sealing of the tip 1432, 1532 of the laryngeal cuff 1418, 1518 in the upper esophagus region of the human or animal patient. The annular flange sealing portions 1490, 1590 are formed from a soft polymeric or other plastics material with a Shore hardness of between 40 and 000 on the A scale. The annular flange sealing portions 1490, 1590 allow for better sealing with a more variable range of upper oesophageal anatomical features.

Figure 38:
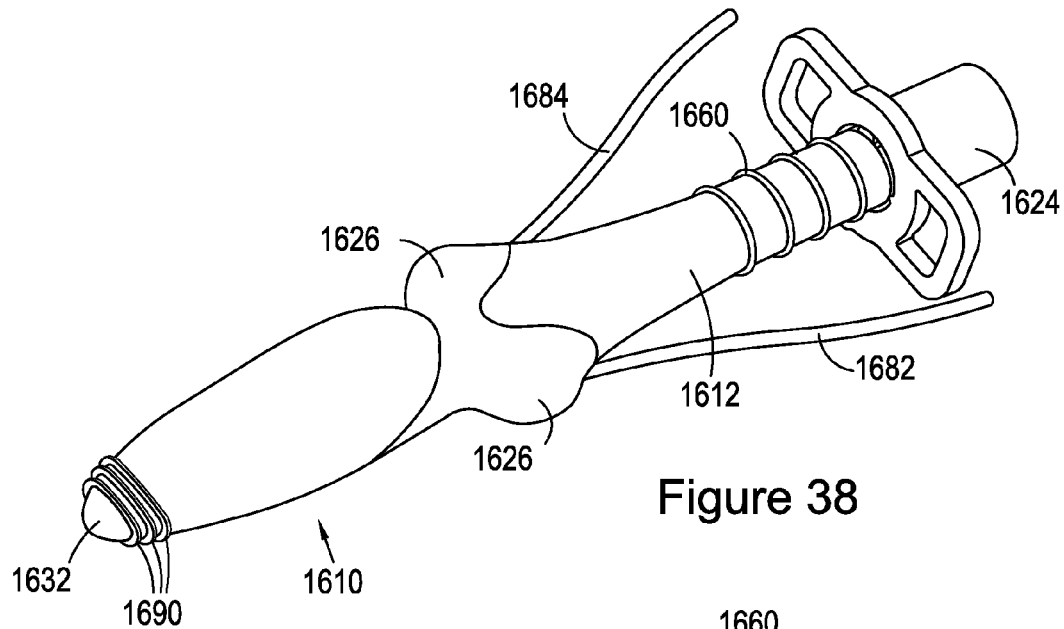
FIG. 38 is a bottom perspective view of an airway device according to a thirteenth embodiment of the present invention.
Figure 39:
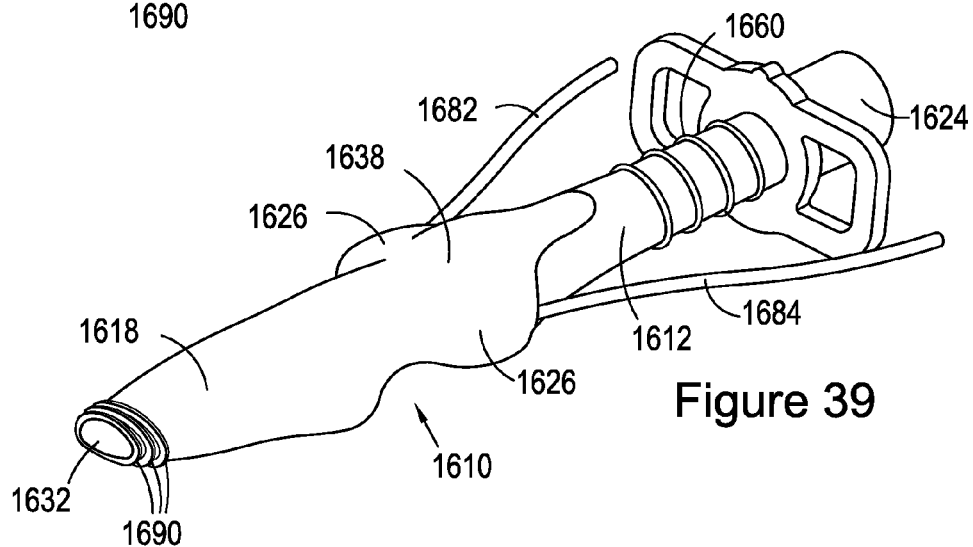
FIG. 39 is a top perspective view of an airway device according to a thirteenth embodiment of the present invention.
Figure 40:
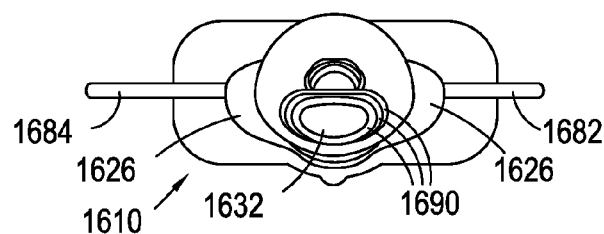
FIG. 40 is an end view of an airway device according to a thirteenth embodiment of the present invention.
Figure 49:
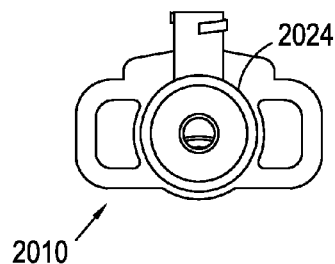
FIG. 49 is a back end view of an airway device according to an eighteenth embodiment of the present invention.
Figure 50:
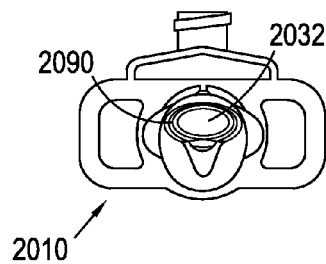
FIG. 50 is a front end view of an airway device according to an eighteenth embodiment of the present invention.
Figure 51:
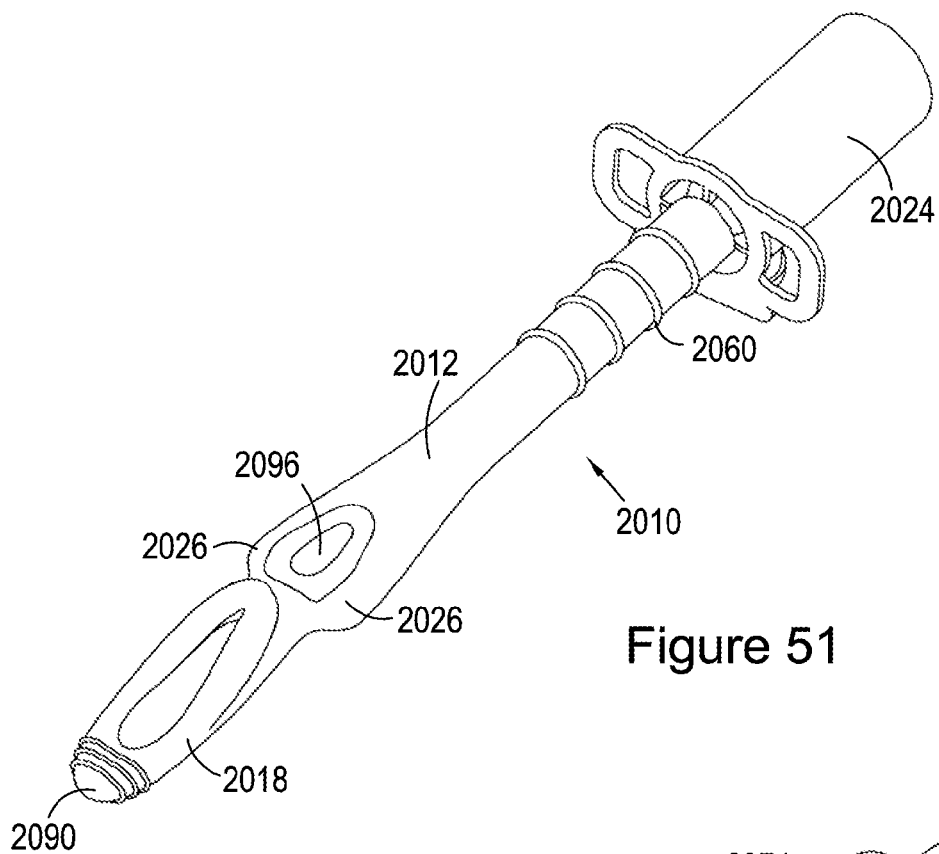
FIG. 51 is a bottom perspective view of an airway device according to an eighteenth embodiment of the present invention.
Figure 52:
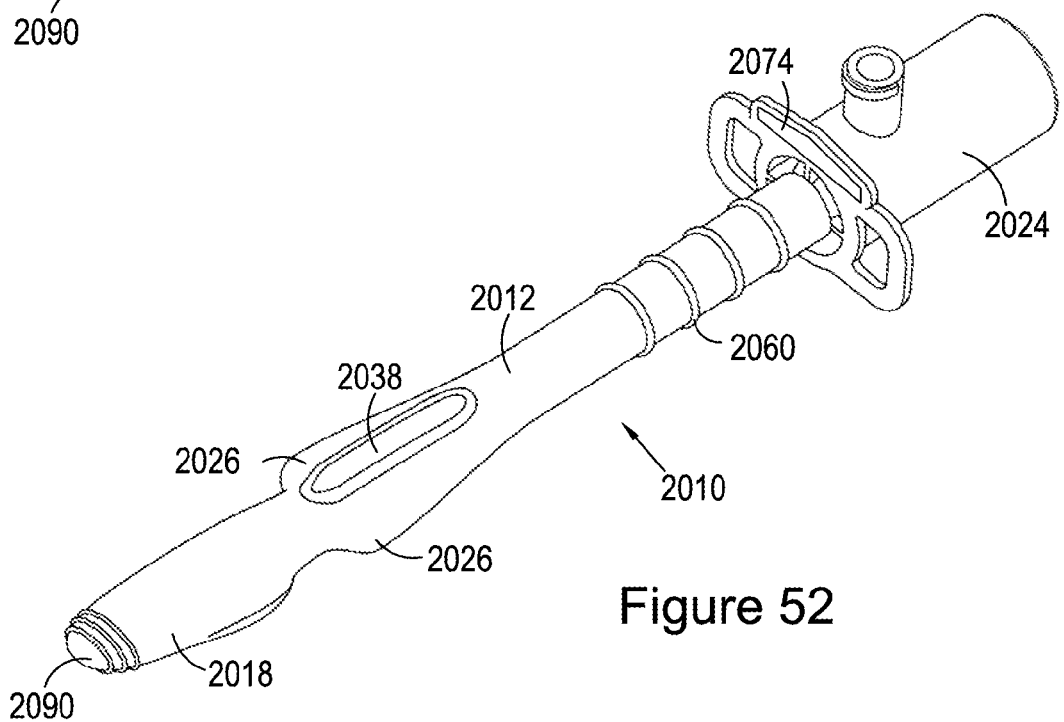
FIG. 52 is a top perspective view of an airway device according to an eighteenth embodiment of the present invention.
Figure 53:
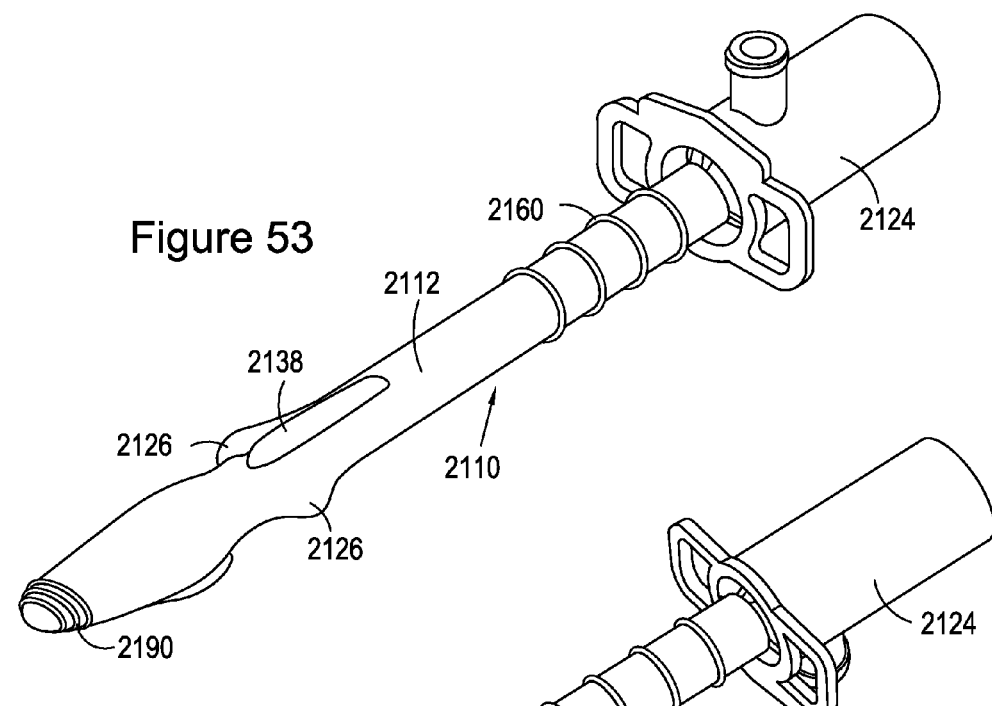
FIG. 53 is a top perspective view of an airway device according to a nineteenth embodiment of the present invention.
Figure 54:
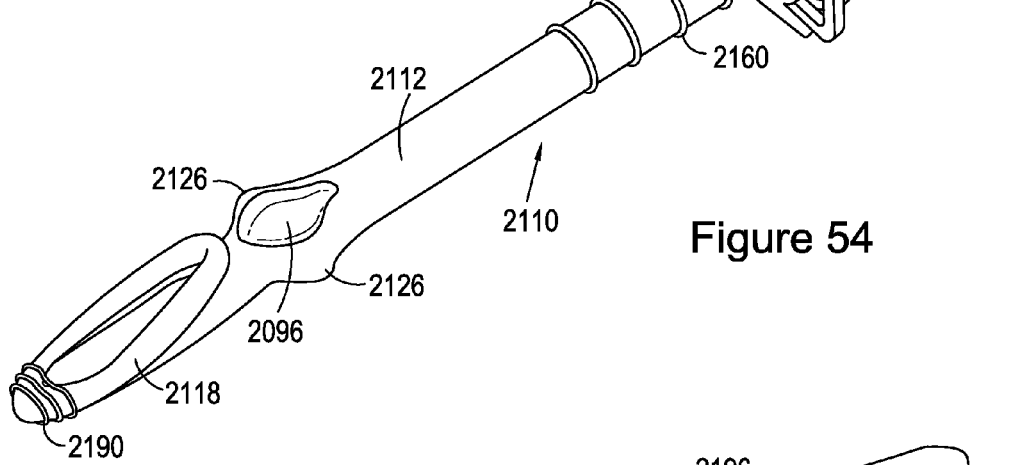
FIG. 54 is a bottom perspective view of an airway device according to a nineteenth embodiment of the present invention.
Figure 55:
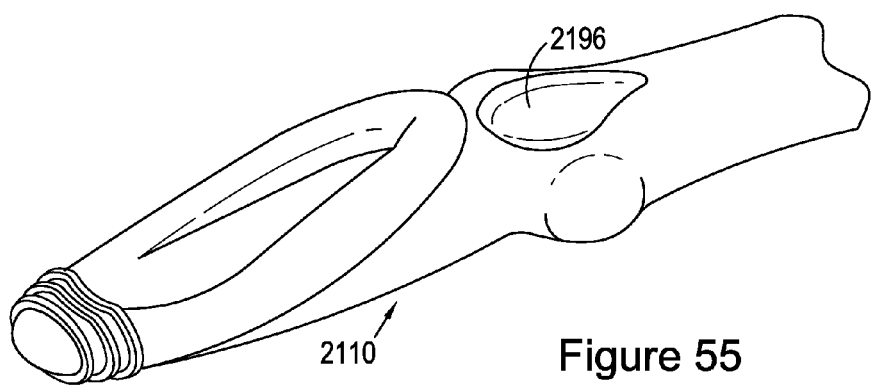
FIG. 55 is a bottom perspective view of a portion of an airway device according to a nineteenth embodiment of the present invention.
Figure 56:
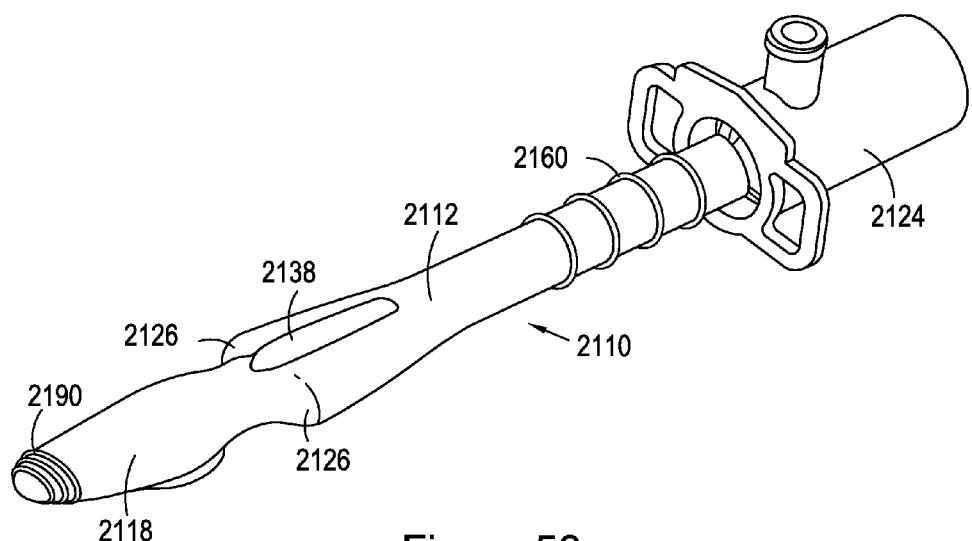
FIG. 56 is a top front perspective view of an airway device according to a nineteenth embodiment of the present invention.
Figure 57:
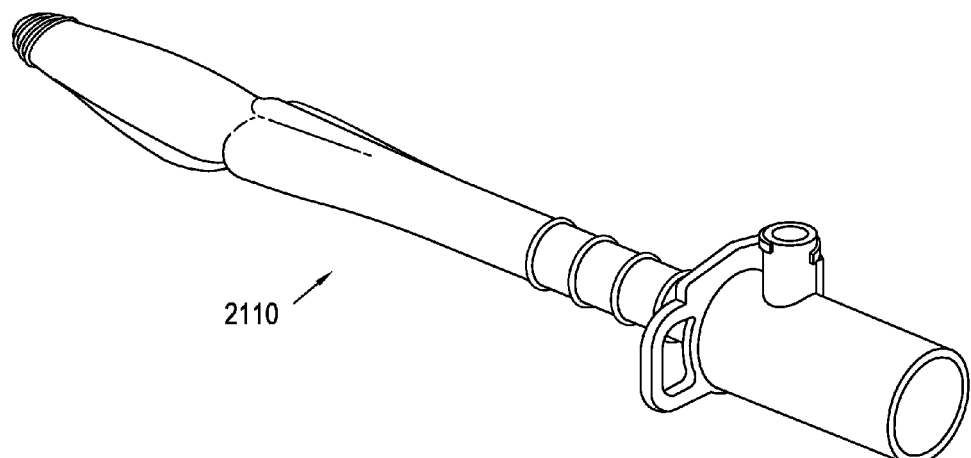
FIG. 57 is atop rear perspective view of an airway device according to a nineteenth embodiment of the present invention.
Figure 58:
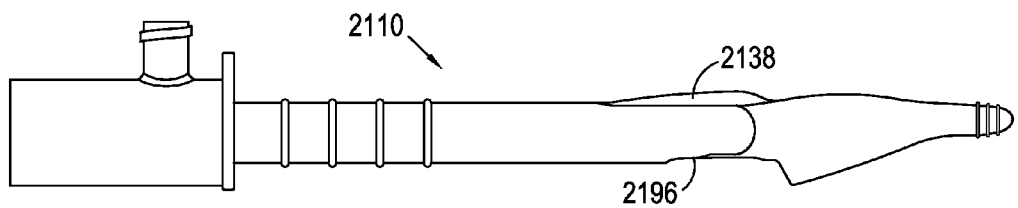
FIG. 58 is a side view of an airway device according to a nineteenth embodiment of the present invention.
Figure 59:
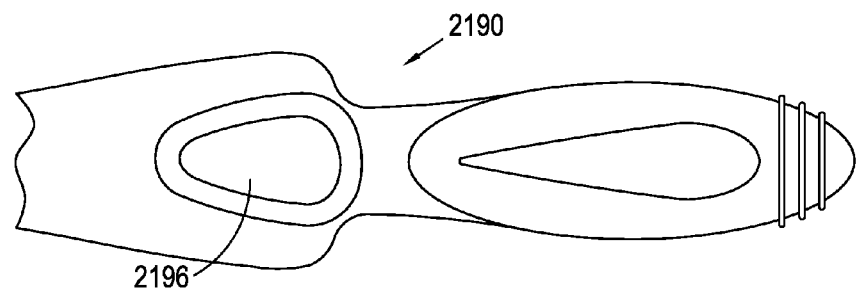
FIG. 59 is a bottom view of a portion of an airway device according to a nineteenth embodiment of the present invention.

FIGS. 38 to 40 illustrate another embodiment of an airway device 1610. In addition to the features of an airway tube 1612, laryngeal cuff 1618 and connector portion 1624, the airway device 1610 is provided with a shoulder portion 1626 and a raised portion 1638 and a plurality of ribs 1660 as discussed above in relation to other embodiments of the present invention. The other features associated with the embodiment of the airway device illustrated in FIGS. 49 and 51 are the presence of two suction channels 1682, 1684. The suction channels 1682, 1684 are provided to assist the removal of fluids which may build up at the back of the mouth. The suction channels 1682, 1684 may be integral with or separate from the oesophageal gastric channel (not shown) if one is provided. The suction channels 1682, 1684 in FIGS. 38 to 40 extend beyond the shoulder portion towards the connector end of the airway device. In addition the tip 1632 of the laryngeal cuff in these embodiments is provided with a series of annular flange sealing portions 1690. The annular flange sealing portions 1690 are provided for improved sealing of the tip 1632 of the laryngeal cuff in the upper esophagus region of the human or animal patient. The annular flange sealing portions 1690 are formed from a soft polymeric or other plastics material with a Shore hardness of between 40 and 000 on the A scale. The annular flange sealing portions 1690 allow for better sealing with a more variable range of upper oesophageal anatomical features.

FIGS. 41 and 42 illustrate another embodiment of an airway device 1710. In this embodiment instead of a laryngeal type airway device it is an endotracheal type airway device. The airway device has an airway tube 1712 with a first end 1714 and a second end 1716. The first end 1714 is provided with a connector 1724 for connecting to the air and/or anaesthetic gas supply and the second end is provided with a cuff 1718.

The cuff 1718 shown in the embodiment is an inflatable cuff and therefore an inflation line 1792 is also provided. The airway device 1710 also has a shoulder 1726. The shoulder portion 1726 is used to prevent over-insertion of the airway device 1710. The shoulder 1726 is located laterally to the direction of flow of the airflow, and thus the airway tube 1712. The shoulder 1726 is used to create a point of contact between the airway device 1710 and faucial pillars located at the back of the mouth of a human or animal patient. This thus creates a positive stopping feature that in use prevents the shoulder 1726 going forward beyond the faucial pillars of the patient to prevent over-insertion of the airway device 1710. In order to further minimize contact and thus reduce trauma around the faucial pillar tissues, the leading edge 30 of the shoulder 1726 may be vertically angled.

In the embodiment illustrated in FIGS. 41 and 42 the shoulder 1726 is formed integrally with the airway device 1710. In the alternative, the shoulder 1726 can be separately attached through using combined materials welding process techniques or by using various bonding or mechanical attachment methods to the airway tube 1712. Further in the alternative the shoulder may include an inflatable region. Yet further in the alternative the shoulder may have a hard core covered in a softer skin to minimize trauma yet provide a rigid structure, particularly in the case of stronger animals such a horses.

The airway device 1710 is further provided with a raised portion 1738, which is located on the airway tube 1712 above and extending just behind the shoulder region 1726 towards the second end 1716 of the airway tube. When in situ in a patient, the raised portion 1738 corresponds to location of the cavity of the upper mouth arch of the patient called the palatoglossal arch. In the embodiment shown in FIGS. 41 and 42 the raised portion 1738 is a bulge, however in alternative embodiments the raised portion 1738 may be a plurality of ribs or fins. Further in the alternative the raised portion may include an inflatable region. Yet further in the alternative the raised portion may have a hard core covered in a softer skin to minimize trauma yet provide a rigid structure, particularly in the case of stronger animals such a horses.

FIG. 43 illustrates another alternative embodiment of an airway device 3810. In this embodiment a perforated plate 3840 has been provided. The perforated plate 3840 is provided to prevent the epiglottis of the patient from occluding the airway if the epiglottis should become downfolded.

FIG. 44 illustrates another alternative embodiment of an airway device 2810. In this embodiment a mesh 2840 has been provided. The mesh 2840 is provided to prevent the epiglottis of the patient from occluding the airway if the epiglottis should become downfolded.

Figure 45:
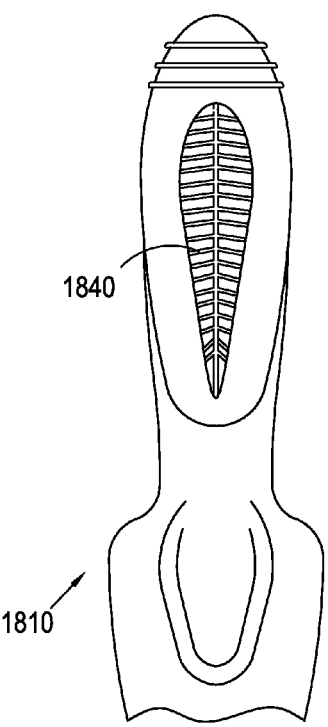
FIG. 45 is a bottom view of a portion of an airway device according to an seventeenth embodiment of the present invention.
Figure 46:
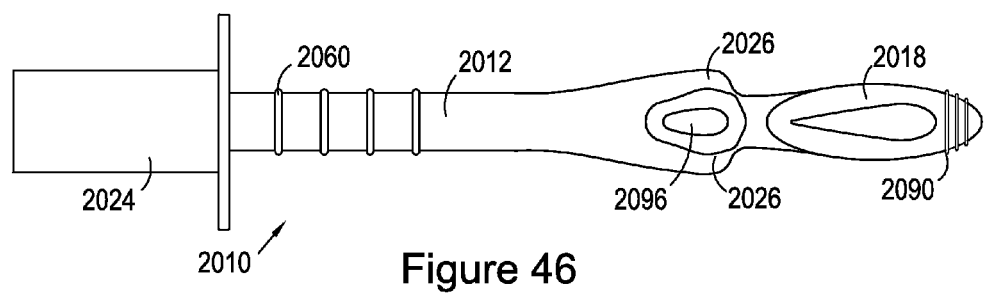
FIG. 46 is a bottom view of an airway device according to an eighteenth embodiment of the present invention.
Figure 47:
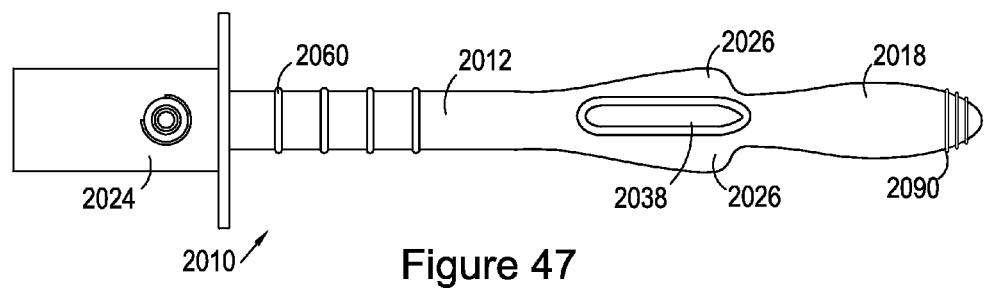
FIG. 47 is a top view of an airway device according to an eighteenth embodiment of the present invention.
Figure 48:
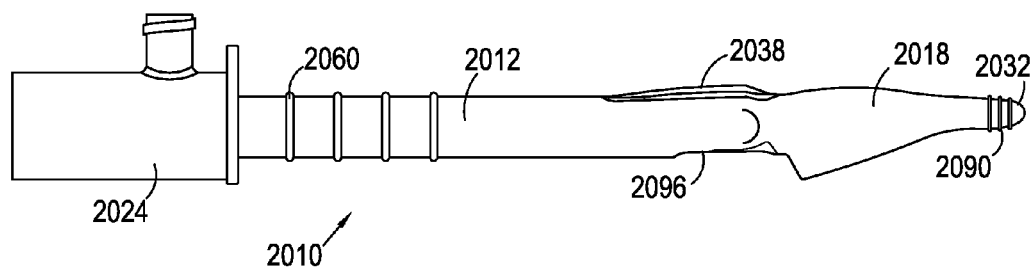
FIG. 48 is a side view of an airway device according to an eighteenth embodiment of the present invention.

FIG. 45 illustrates another alternative embodiment of an airway device 1810. In this embodiment a series of ribs 1840 have been provided in the form of a skeleton. The ribs 1840 are provided to prevent the epiglottis of the patient from occluding the airway if the epiglottis should become downfolded.

FIGS. 46 to 52 illustrate another embodiment of an airway device 2010. In addition to the standard features of an airway tube 2012, laryngeal cuff 2018 and connector portion 2024, the airway device 2010 is provided with a shoulder 2026 and a raised portion 2038, annular flanges 2090 around the tip of the laryngeal cuff and a plurality of ribs 2060 near the connector portion 2024 as discussed above in relation to other embodiments of the present invention. The main additional feature associated with the embodiment of the airway device illustrated in FIGS. 46 to 52 is the presence of a concave portion or scallop 2096 which is provided in the airway tube 2012. The concave portion or scallop 2096 is located on the opposite side of the airway tube 2012 to the raised portion 2038 around the location of the shoulder 2026. The concave portion or scallop 2096 is located at the back of the tongue of the human or animal patient in use. The concave portion or scallop 2096 acts to reduce the amount of pressure being applied to the convex portion at the back of the tongue. When pressure is applied to the convex portion at the back of the tongue, this results in the formation of blue tongue in the human or animal patient because the pressure to the tongue constricts the blood vessels.

In this embodiment a marker 2094 is provided on the connector 2024 to indicate which orientation the device is in after the device has been inserted into the patient. This provides a double check that the device is correctly orientated and inserted into the correct position leaving no doubt to the clinician. The indicator is particularly important in veterinary use whereby its critical to know which orientation the airway device has been inserted as a further fail safe feature. Sometimes animals are placed on their front and back and vets can easily forget which is the right orientation for device to be inserted as the animal is placed into position first and then the device is inserted.

FIGS. 53 to 59 illustrate another embodiment of an airway device 2110. In addition to the standard features of an airway tube 2112, laryngeal cuff 2118 and connector portion 2124, the airway device 2110 is provided with a shoulder 2126 and a raised portion 2138, annular flanges 2190 around the tip of the laryngeal cuff and a plurality of ribs 2160 near the connector portion 2124 as discussed above in relation to other embodiments of the present invention. The main additional feature associated with the embodiment of the airway device illustrated in FIGS. 53 to 59 is the presence of a concave portion or scallop 2196 which is provided in the airway tube 2112. The concave portion or scallop 2196 is located on the opposite side of the airway tube 2112 to the raised portion 2138 around the location of the shoulder portion 2126. The concave portion or scallop 2196 is located at the back of the tongue of the human or animal patient in use. The concave portion or scallop 2196 acts to reduce the amount of pressure being applied to the convex portion at the back of the tongue. When pressure is applied to the convex portion at the back of the tongue, this results in the formation of blue tongue in the human or animal patient because the pressure to the tongue constricts the blood vessels.

Figure 60:
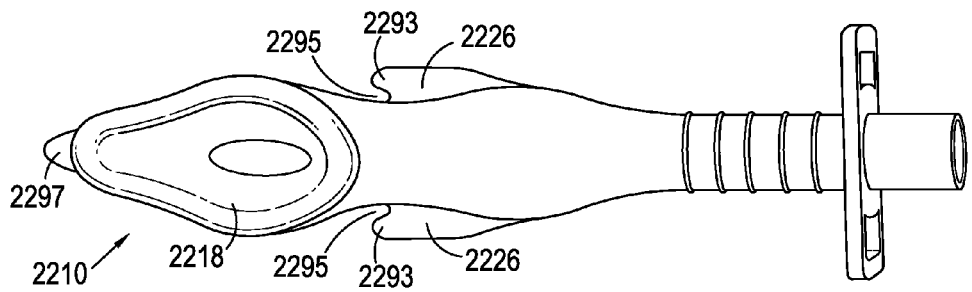
FIG. 60 is a bottom view of an airway device according to a twentieth embodiment of the present invention.
Figure 61:
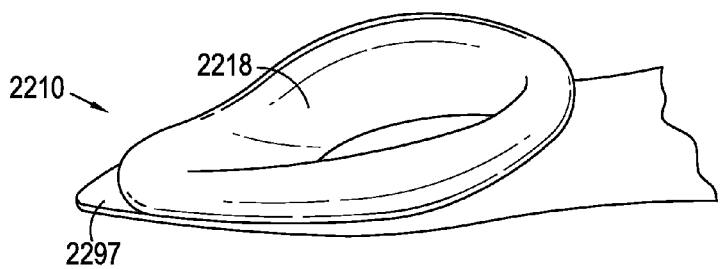
FIG. 61 is a bottom perspective view of a portion of an airway device according to a twentieth embodiment of the present invention.

FIGS. 60 and 61 illustrate another embodiment of an airway device 2210. This embodiment exemplifies the feature of the forward facing protrusions 2293, seen earlier in respect of the embodiment illustrated in FIGS. 4 to 6. The forward facing protrusions 2293 are located on the leading edge of the shoulder 2236. The forward facing protrusions 2293 are adapted to locate into anatomical cavities which are present in dogs, for example, after the pharyngeal arches. In general dogs have a very wide pharyngeal arch as they are designed to consume large volumes of food very rapidly. The forward facing protrusions 2293 being adapted to fit into the anatomical cavity region to make the whole airway device 2210 fit more securely and not easily by-pass the pharyngeal arches. It is worth bearing in mind that the pharyngeal arches are particularly elastic in dogs. Cavities 2295 are adapted to fit the thin protruding pharyngeal arches of the dog, without which the shoulders 2226 may be able to extend beyond. The cuff 2218 of the airway device 2210 is further provided with a blade like tip 2297. The blade like tip 2297 is used to "flick" or peel the epiglottis of a dog downwards as the airway device 2210 is inserted in a single action. The size of the tip is such that it also fits closely within the esophagus.

Figure 62:
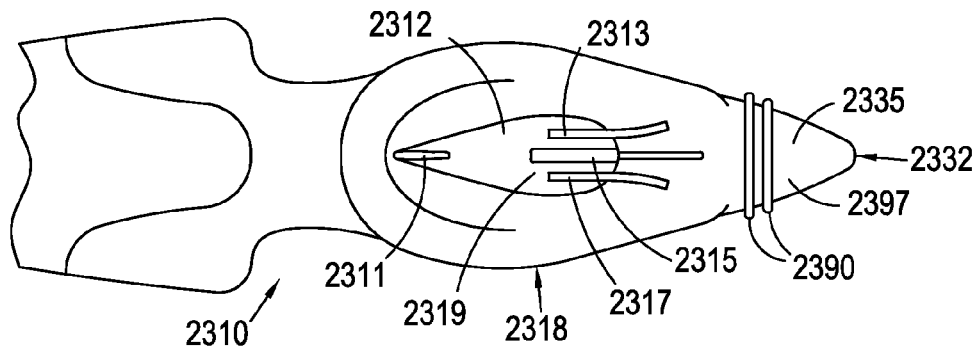
FIG. 62 is a bottom view of a portion of an airway device according to a twenty-first embodiment of the present invention.
Figure 63:
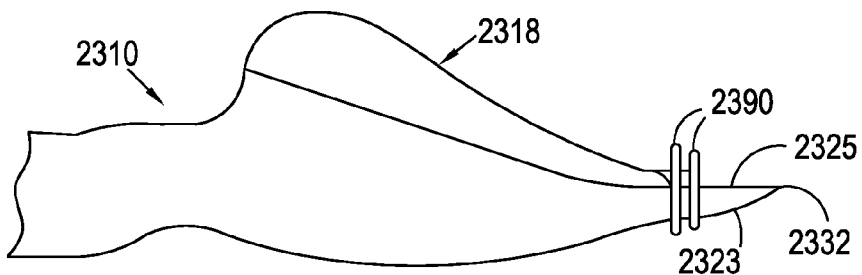
FIG. 63 is a side view of a portion of an airway device according to a twenty-first embodiment of the present invention.

FIGS. 62 and 63 show an alternative embodiment of the cuff 2318 for the airway device 2310. In this embodiment a bracket 2311 has been provided at the proximal end of the cuff 2318 to provide a rest for the epiglottis of the patient to prevent the epiglottis from downfolding and blocking the airflow. In addition a series of further brackets 2313, 2315, 2317 have been provided at the distal end of the cuff 2318 to further strengthen the cuff 2318 and in particular the tip 2397 to enable the tip 2397 to manipulate the epiglottis of the patient during insertion of the airway device 2810. The further brackets 2313, 2315, 2317 also provide a rest for any particularly large epiglottis, if downfolded, from blocking the airflow. In one alternative the brackets 2311, 2313, 2315, 2317 simply extend horizontally in the plane of the cuff 2318. In an alternative the brackets extend both horizontally and vertically in the plane of the cuff such that they extend to the back 2319 of the cuff opening 2321. In this embodiment the tip 2322 is a blade like tip 2397. The blade like tip 2397 is contoured on the dorsal portion of the tip 2323 in line with the dorsal portion of the cuff and substantially planar on the front face portion of the tip 2325. The blade like tip 2397 is used to "flick" or peel the epiglottis of the patient downwards before the airway device 2310 is inserted. Finally in this embodiment the tip 2392 of the cuff is further provided with a series of annular flange sealing portions 2390. The annular flange sealing portions are provided for improved sealing of the tip 2332 of the laryngeal cuff 2318 in the upper esophagus region of the human or animal patient. The annular flange sealing portions 2390 are formed from a soft polymeric or other plastic material with a Shore hardness of between 40 and 000 on the A scale. The annular flange sealing portions 2390 allow for better sealing with a more variable range of upper oesophageal anatomical features.

Figure 64:
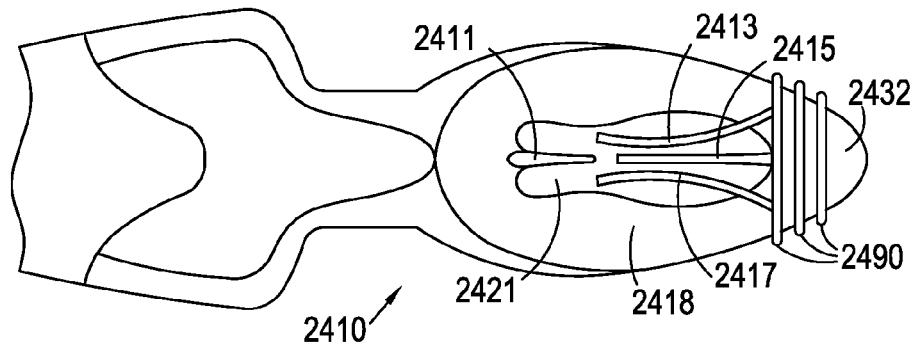
FIG. 64 is a bottom view of a portion of an airway device according to a twenty-second embodiment of the present invention.
Figure 65:
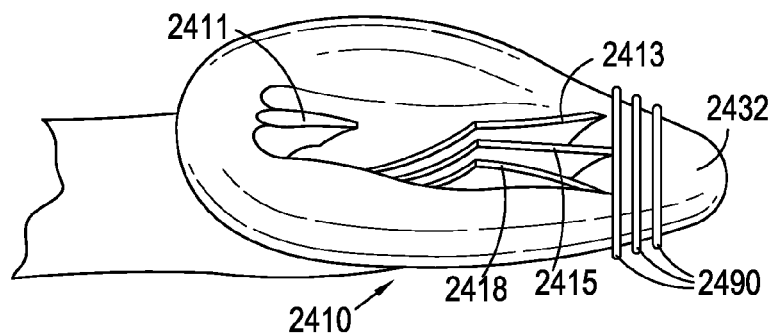
FIG. 65 is a bottom perspective view of a portion of an airway device according to a twenty-second embodiment of the present invention.

FIGS. 64 and 65 illustrate an alternate embodiment of an airway device 2410 and the brackets 2411, 2413, 2415, 2417 described in respect of FIGS. 64 and 65 above. In this embodiment the proximal end of the cuff 2418 rather than being v-shaped is w-shaped with a bracket 2411 provided in the centre of the w-shape. The w-shape provides a greater area of the opening 2421 of the cuff 2418. This means that if the epiglottis of the patient should downfold and the rest on the bracket 2411 there will be space either side of the downfolded epiglottis that is still open to airflow. The further brackets 2413, 2415, 2417 provide the same function as described in FIGS. 64 and 65 above. This embodiment has also been provided with annular sealing portions 2490 at the tip of the cuff 2432 also as described in relation to FIGS. 64 and 65 above.

Figure 66:
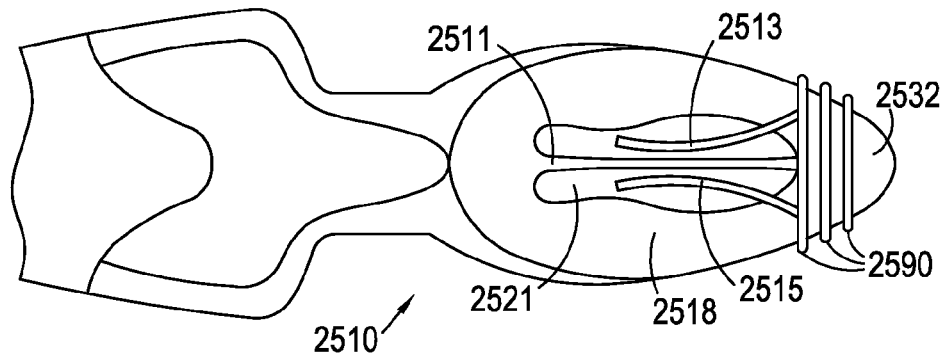
FIG. 66 is a bottom view of a portion of an airway device according to a twenty-third embodiment of the present invention.

FIG. 66 illustrates a further alternative embodiment of an airway device 2510 to that shown in FIGS. 64 and 65 above. In this embodiment the bracket 2511 extends from the proximal end of the cuff opening to the distal end of the cuff opening across the full length of the cuff opening 2521. This provides for the situation that the epiglottis is longer than the first bracket at the proximal opening of the cuff described in FIGS. 64 and 65 above, but not long enough to reach the further bracket at the distal opening of the cuff, so that the epiglottis does not fall down in the centre of the brackets and occlude the airflow. In addition the full length bracket 2511 provides further strength to the overall cuff 2518. Further brackets 2513, 2518 are provided at the distal opening of the cuff to provide additional strength. In this embodiment the tip of the cuff 2532 is further provided with annular sealing portions 2590 as described in FIGS. 64 and 65 above.

Figures 67, 68:
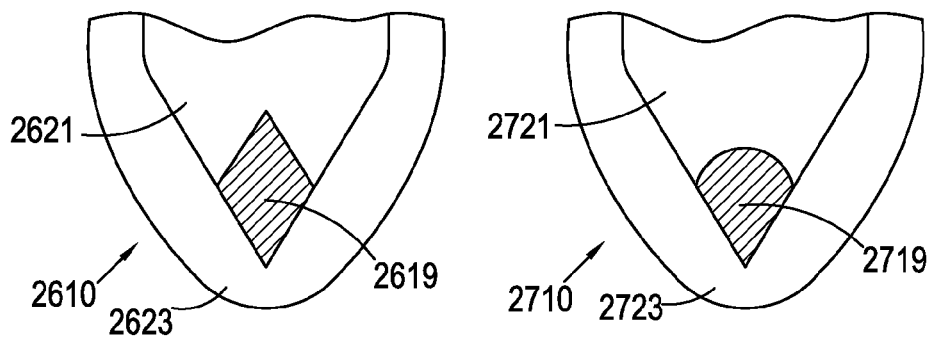
FIG. 67 is a bottom view of a portion of an airway device according to a twenty-fourth embodiment of the present invention.
FIG. 68 is a bottom view of a portion of an airway device according to a twenty-fifth embodiment of the present invention.

FIGS. 67 and 68 illustrate two alternative tip 2632, 2732 arrangements for airway devices 2610, 2710. In these embodiments instead of providing brackets at the distal opening of the cuff 2621, 2721 an area of rigid material 2619, 2719 is provided. As well as strengthening the tip 2632, 2732, the rigid material 2679, 2719 acts as a flow director and also as a means to prevent the epiglottis of the human or animal patient from becoming downfolded and blocking the airflow.

Figure 69:
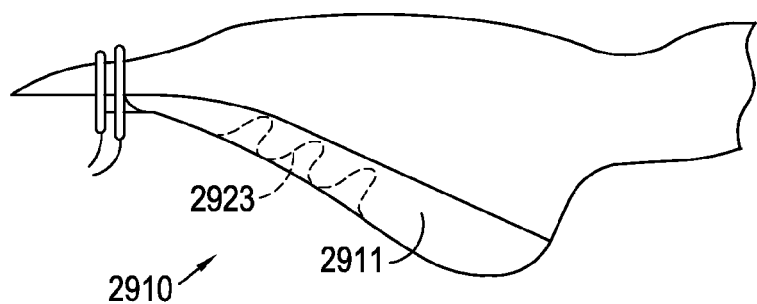
FIG. 69 is a bottom view of a portion of an airway device according to a twenty-sixth embodiment of the present invention.
Figure 70:
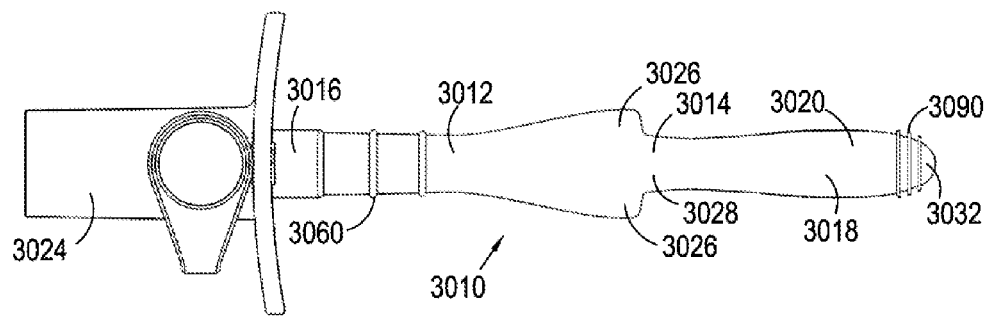
FIG. 70 is a top view of an airway device according to a twenty-seventh embodiment of the present invention.
Figure 71:
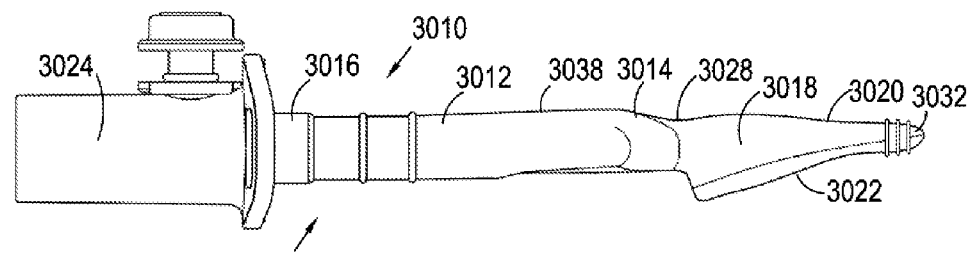
FIG. 71 is a side view of an airway device according to a twenty-seventh embodiment of the present invention.
Figure 72:
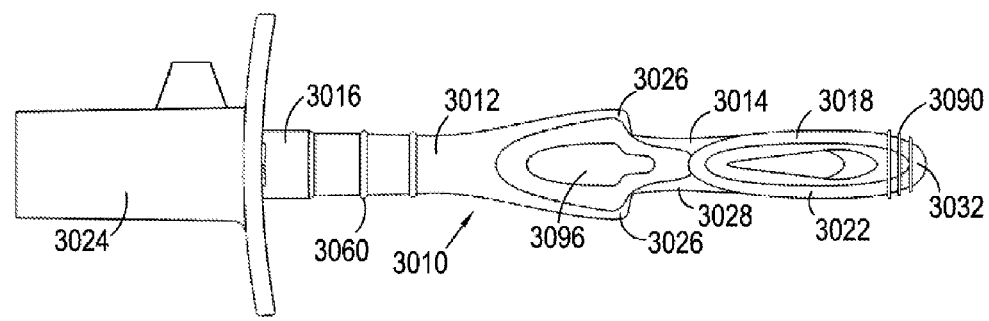
FIG. 72 is a bottom view of an airway device according to a twenty-seventh embodiment of the present invention.
Figure 73:
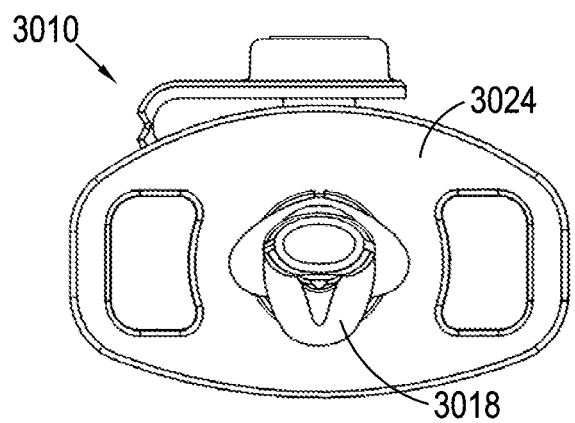
FIG. 73 is a front end view of an airway device according to a twenty-seventh embodiment of the present invention.
Figure 74:
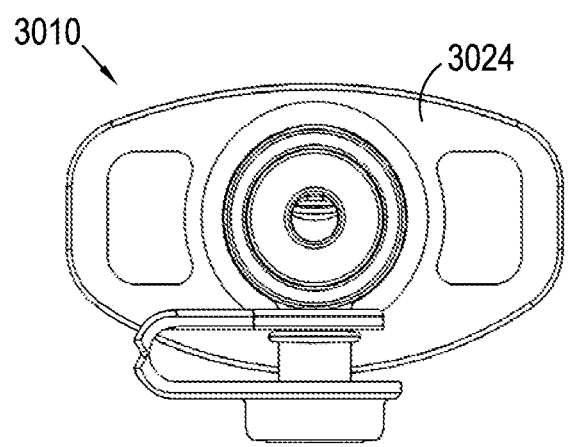
FIG. 74 is a rear end view of an airway device according to a twenty-seventh embodiment of the present invention.
Figure 75:
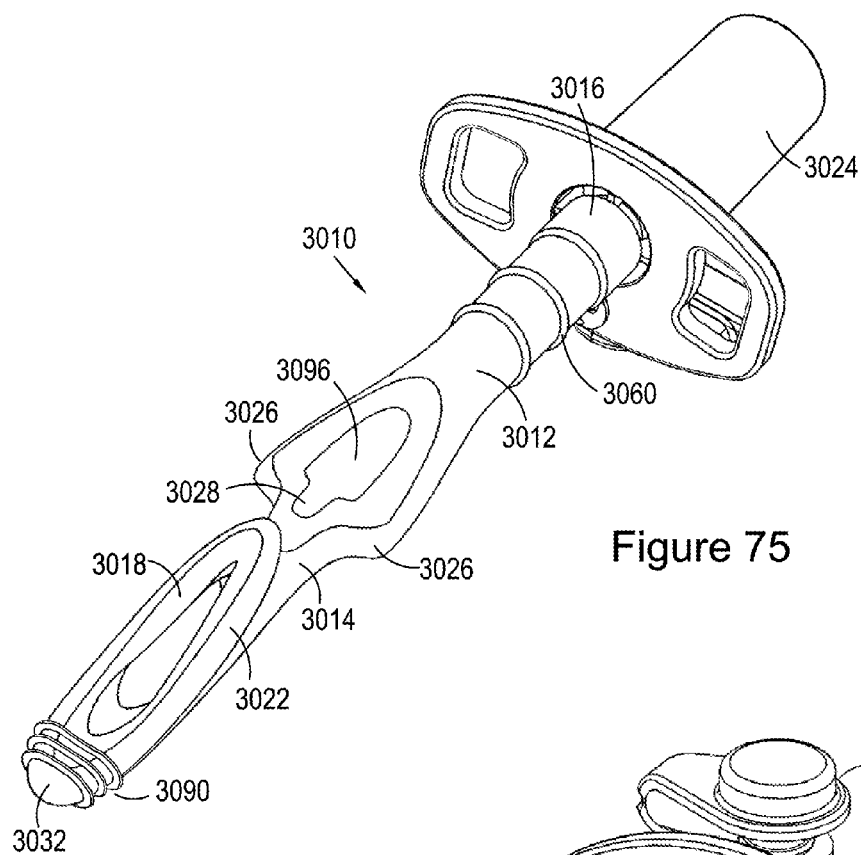
FIG. 75 is a bottom perspective view of an airway device according to a twenty-seventh embodiment of the present invention.
Figure 76:
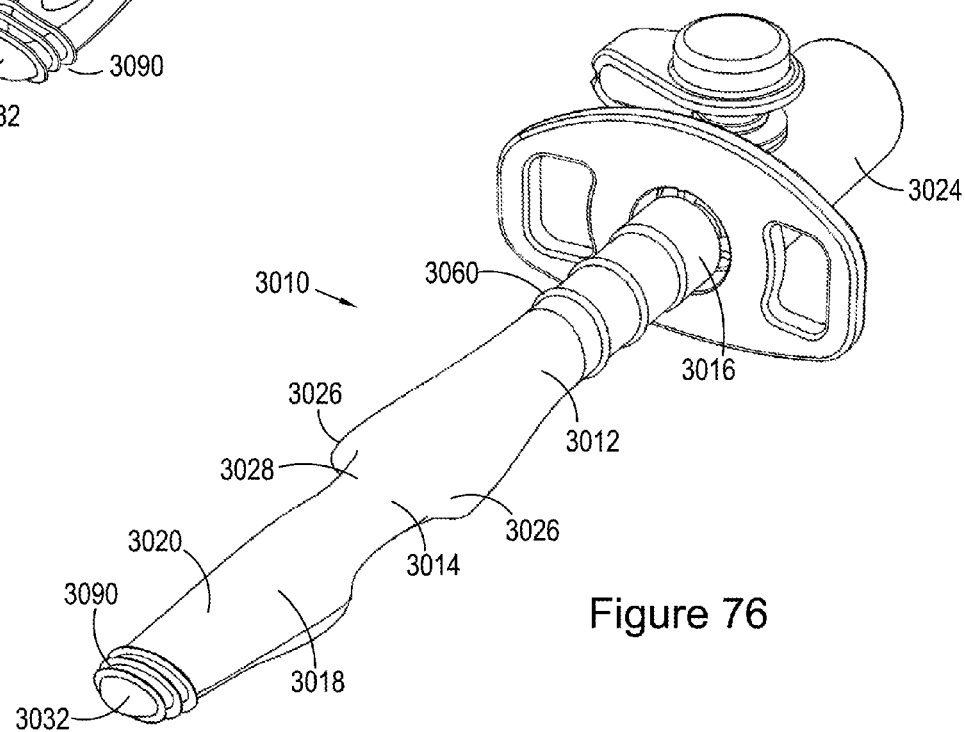
FIG. 76 is a top perspective view of an airway device according to a twenty-seventh embodiment of the present invention.
Figure 77:
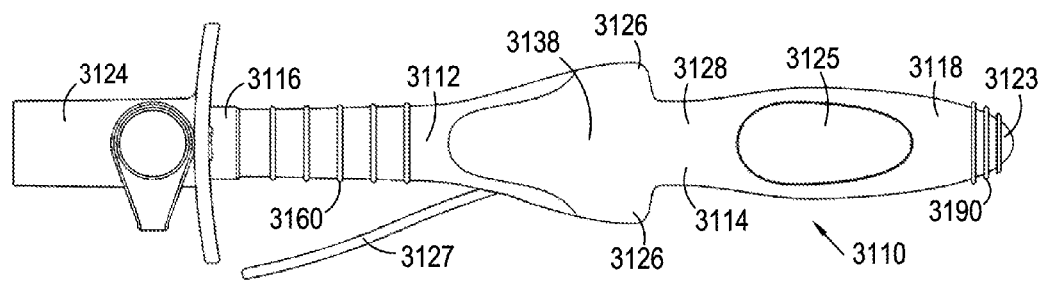
FIG. 77 is a top view of an airway device according to a twenty-eighth embodiment of the present invention.
Figure 78:
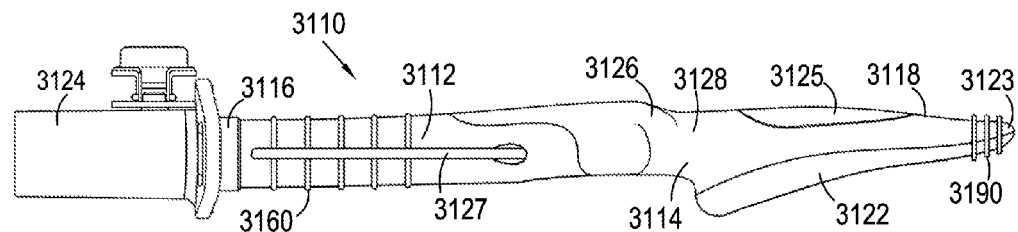
FIG. 78 is a side view of an airway device according to a twenty-eighth embodiment of the present invention.
Figure 79:
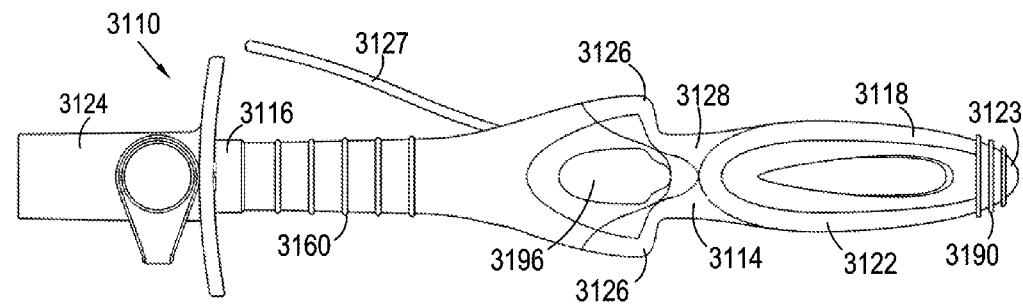
FIG. 79 is a bottom view of an airway device according to a twenty-eighth embodiment of the present invention.
Figure 80:
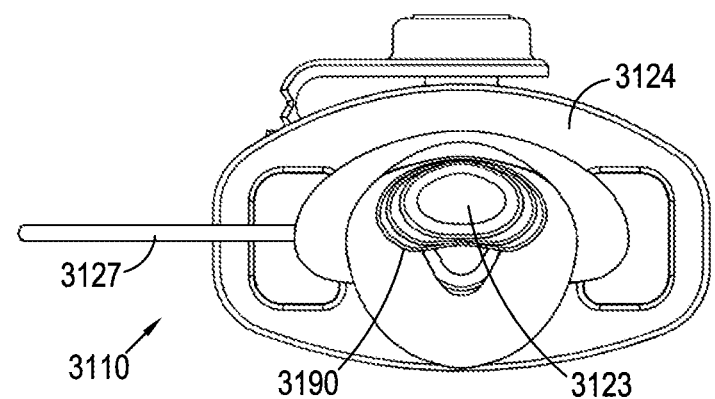
FIG. 80 is a front end view of an airway device according to a twenty-eighth embodiment of the present invention.
Figure 81:
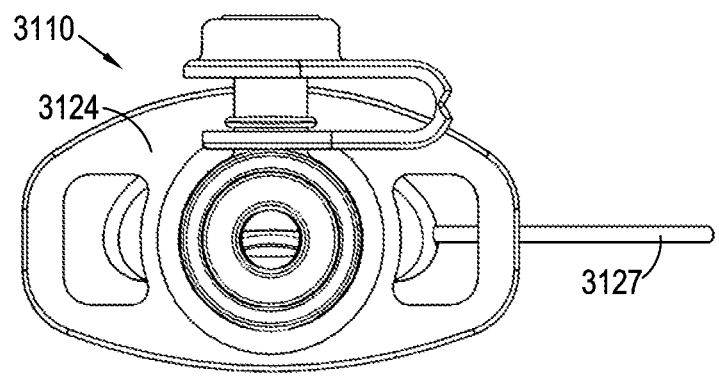
FIG. 81 is a rear end view of an airway device according to a twenty-eighth embodiment of the present invention.
Figure 89:
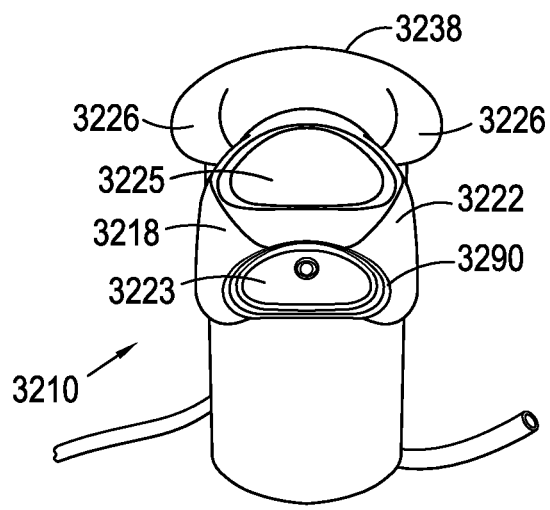
FIG. 89 is a front end view of an airway device according to a twenty-ninth embodiment of the present invention.
Figure 90:
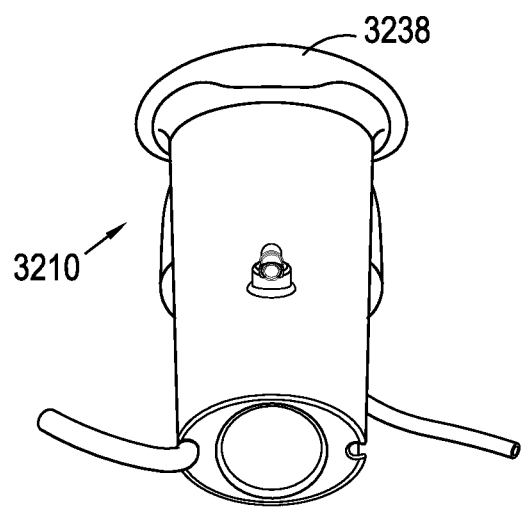
FIG. 90 is a rear end view of an airway device according to a twenty-ninth embodiment of the present invention.
Figure 96:
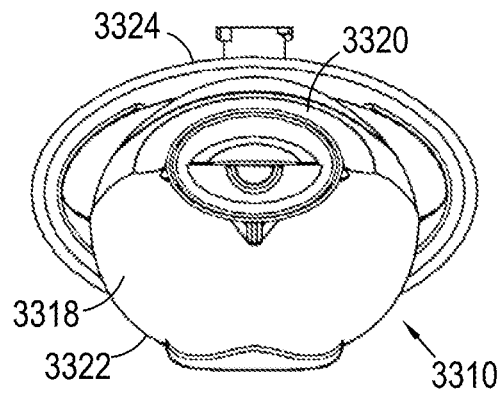
FIG. 96 is a front end view of an airway device according to a thirtieth embodiment of the present invention.
Figure 97:
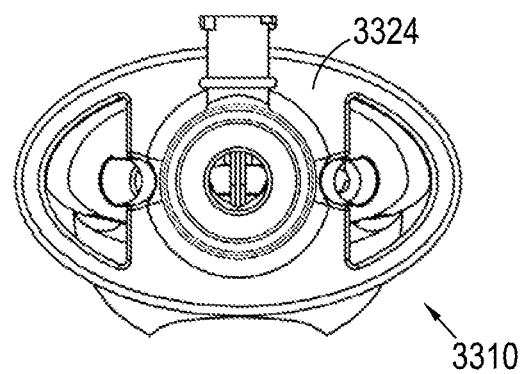
FIG. 97 is a rear end view of an airway device according to a thirtieth embodiment of the present invention.

FIG. 69 shows a modification that may be made to the brackets illustrated in FIGS. 62 to 68. In this embodiment the brackets 2911 may be provided with out outs or notches or grooves 2923 along the front surface of the brackets 2911 to form a wave like shape. In this embodiment, should the epiglottis of the human or animal patient become downfolded and rest on the brackets air will still be able to flow freely in between the brackets to avoid any turbulent air effects which might occur otherwise.

FIGS. 70 to 76 illustrate an embodiment of the airway device 3010 specifically designed for use with a rabbit. The airway device 3010 has an airway tube 3012 with a first end 3014 and a second end 3016. The first end 3014 of the airway tube 3012 is surrounded by a laryngeal cuff 3018. The cuff 3018 has a back dorsal portion 3020 and a front face portion 3022. The front face portion 3022 is shaped to form an anatomical fit over the laryngeal inlet of a rabbit. The second end 3016 of the airway tube is fitted with a connector 3024 such that the second end 3016 of the airway tube 3012 can be connected to the relevant gas supply. The airway device 3010 also has a shoulder 3026. The shoulder 3026 is used to prevent over-insertion of the airway device 3010. The shoulder 3026 is located laterally and substantially perpendicular to the direction of the airflow, and thus the airway tube 3012. The shoulder 3026 is located just above the neck 3028 of the airway device 3010 where the laryngeal cuff 3018 appears to join the airway tube 3012 at the second end 3014. The shoulder 3026 is used to create a point of contact between the airway device 3010 and the faucial pillars of the rabbit located at the back of the rabbits mouth. This thus creates a positive stopping feature that in use prevents the shoulder 3026 going forward beyond the faucial pillars of the rabbit and thus prevents over-insertion of the airway device 3010.

The airway device 3010 is further provided with a raised portion 3038. The raised portion 3038 is located on the airway tube 3012 above and extending just behind the shoulder 3026 towards the second end 3016 of the airway tube, when in situ in the rabbit, the raised portion 3038 corresponds to the location of the cavity of the upper mouth arch of the rabbit called the palatoglossal arch. The raised portion 3038 aids in preventing over-insertion of the airway device by being adapted to locate in the cavity of the palatoglossal arch, due to the contouring of the raised portion, and provides resistance on being moved beyond this position. The raised portion 3038 is not meant to be in constant contact with the palatogiossal arch but simply to locate into this cavity to prevent over-insertion and resist movement of the device when in situ.

The airway device 3010 is also further provided with a plurality of ribs 3060 near the second end 3016 of the airway tube 3012 near to the connector 3024. The ribs 3060 provide a friction point for tying the device around the rabbit's head as it is generally not possible to use tape as in humans due to the rabbit's fur.

The tip 3032 of the laryngeal cuff 3018 is also provided with a series of annular flange sealing portions 3090. The annular flange sealing portions 3090 are provided for improved sealing of the tip 3032 of the laryngeal cuff 3018 in the upper esophagus region of the rabbit. The annular flange sealing portions are formed of a soft polymeric or other plastics material with a Shore hardness of between 40 and 000 on the A scale. The annular flange sealing portion 3090 allows for better sealing with a more variable range of upper oesophageal features.

The airway device 3010 is also provided with a concave portion or scallop 3096 on the airway tube 3012. The concave portion or scallop 3096 is located on the opposite side of the airway tube 3012 to the raised portion 3038 around the location of the shoulder 3026. The concave portion of scallop 3096 is located at the back of the tongue of the rabbit in use. The concave portion or scallop 3096 acts to reduce the amount of pressure being applied to the convex portion of back of the tongue. When pressure is applied to the convex portion at the back of the tongue, this results in the formation of blue tongue in rabbits because the pressure to the tongue constricts blood vessels.

FIGS. 77 to 83 illustrate an embodiment of the airway device 3110 specifically designed for use with a cat. The airway device 3110 has an airway tube 3112 with a first end 3114 and a second end 3116. The first end 3114 of the airway tube 3112 is surrounded by a laryngeal cuff 3118. The cuff 3118 has a back dorsal portion 3120 and a front face portion 3122. The front face portion 3122 is shaped to form an anatomical fit over the laryngeal inlet of a cat. The second end 3116 of the airway tube is fitted with a connector 3124 such that the second end 3116 of the airway tube 3112 can be connected to the relevant gas supply. The airway device 3110 also has a shoulder 3126. The shoulder 3126 is used to prevent over-insertion of the airway device 3110. The shoulder 3126 is located laterally and substantially perpendicular to the direction of the airflow, and thus the airway tube 3112. The shoulder 3126 is located just above the neck 3128 of the airway device 3110 where the laryngeal cuff 3118 appears to join the airway tube 3112 at the second end 3114. The shoulder 3126 is used to create a point of contact between the airway device 3110 and the faucial pillars of the cat located at the back of the cats mouth. This thus creates a positive stopping feature that in use prevents the shoulder portion 3126 going forward beyond the faucial pillars of the cat and thus prevents over-insertion of the airway device 3110.

The airway device 3110 is further provided with a raised portion 3138. The raised portion 3138 is located on the airway tube 3112 above and extending just behind the shoulder 3126 towards the second end 3116 of the airway tube, when in situ in the cat, the raised portion 3138 corresponds to the location of the cavity of the upper mouth arch of the cat called the palatoglossal arch. The raised portion 3138 aids in preventing over-insertion of the airway device by being adapted to locate in the cavity of the palatoglossal arch due to the contouring of the raised portion and provides resistance on being moved beyond this position. The raised portion 3138 is not meant to be in constant contact with the palatoglossal arch but simply to locate into this cavity to prevent over-insertion and resist movement of the device when in situ.

The airway device 3110 is also further provided with a plurality of ribs 3160 near the second end 3116 of the airway tube 3112 near to the connector 3124. The ribs 3160 provide a friction point for tying the device around the cat's head as it is generally not possible to use tape as in humans due to the cat's fur.

The tip 3132 of the laryngeal cuff 3118 is also provided with a series of annular flange sealing portions 3190. The annular flange sealing portions 3190 are provided for improved sealing of the tip 3132 of the laryngeal cuff 3118 in the upper esophagus region of the cat. The annular flange sealing portions are formed of a soft polymeric or other plastics material with a shore hardness of between 40 and 000 on the A scale. The annular flange sealing portion 3190 allows for better sealing with a more variable range of upper oesophageal features.

The airway device 3110 is also provided with a concave portion or scallop 3196 on the airway tube 3112. The concave portion or scallop 3196 is located on the opposite side of the airway tube 3112 to the raised portion 3138 around the location of the shoulder 3126. The concave portion of scallop 3196 is located at the back of the tongue of the cat in use. The concave portion or scallop 3196 acts to reduce the amount of pressure being applied to the convex portion of back of the tongue. When pressure is applied to the convex portion at the back of the tongue, this results in the formation of blue tongue in cats because the pressure to the tongue constricts blood vessels.

In addition for the airway device 3110 specifically designed for use in cats the airway device 3110 is further provided with an inflatable back cuff 3125 and inflation line 3127 to inflate the inflatable back cuff 3125. The inflatable back cuff 3125 is designed to lay flush with the profile of the back dorsal portion 3120 of the laryngeal cuff 3118 when not inflated, such that the inflatable back cuff 3125 does not interfere with the insertion of the device 3110. The inflatable back cuff 3125 is provided to give flexibility of fit of the device in different breeds of cat which may have much different sized architecture compared with rabbits to ensure a good seal across all breeds of cat.

FIGS. 84 to 90 illustrate an embodiment of the airway device 3210 specifically designed for use with a horse. The airway device 3210 has an airway tube 3212 with a first end 3214 and a second end 3216. The first end 3214 of the airway tube 3212 is surrounded by a laryngeal cuff 3218. The cuff 3218 has a back dorsal portion 3220 and a front face portion 3222. The front face portion 3222 is shaped to form an anatomical fit over the laryngeal inlet of a horse. The second end 3216 of the airway tube is fitted with a connector 3224 such that the second end 3216 of the airway tube 3212 can be connected to the relevant gas supply. The airway device 3210 also has a shoulder 3226. The shoulder 3226 is used to prevent over-insertion of the airway device 3210. The shoulder 3226 is located laterally and substantially perpendicular to the direction of the airflow, and thus the airway tube 3212. The shoulder 3226 is located just above the neck 3228 of the airway device 3210 where the laryngeal cuff 3218 appears to join the airway tube 3212 at the second end 3214. The shoulder 3226 is used to create a point of contact between the airway device 3210 and the faucial pillars of the horse located at the back of the horses mouth. This thus creates a positive stopping feature that in use prevents the shoulder portion 3226 going forward beyond the faucial pillars of the horse and thus prevents over-insertion of the airway device 3210.

The airway device 3210 is further provided with a raised portion 3238. The raised portion 3238 is located on the airway tube 3212 above and extending just behind the shoulder 3226 towards the second end 3216 of the airway tube, when in situ in the horse, the raised portion 3238 corresponds to the location of the cavity of the upper mouth arch of the horse called the palatoglossal arch. The raised portion 3238 aids in preventing over-insertion of the airway device by being adapted to locate in the cavity of the palatoglossal arch due to the contouring of the raised portion and provides resistance on being moved beyond this position. The raised portion 3238 is not meant to be in constant contact with the palatoglossal arch but simply to locate into this cavity to prevent over-insertion and resist movement of the device when in situ.

The airway device 3210 is also further provided with a plurality of ribs 3260 near the second end 3216 of the airway tube 3212 near to the connector 3224. The ribs 3260 provide a friction point for tying the device around the horse's head as it is generally not possible to use tape as in humans due to the horse's fur.

In order to further discourage over-insertion, the tip 3232 of the laryngeal cuff 3218 is angled upwards away from the horizontal plane of the laryngeal cuff 3218. The tip 3232 may be angled from 5° to 80°. The angle of the tip 3232 has the effect of increasing the surface area of the tip 3232. The tip 3232 engages to seal with the top of the esophagus of the patient when the airway device 3210 is correctly inserted. The larger tip 3232 surface area creates some resistance with the top of the esophagus during insertion which would be felt by the clinician during insertion to determine that the airway 3210 device has been correctly inserted. The tip is formed from materials of two different hardnesses. A soft material is used for the front face portion of the tip 3234 and a harder material is used for the rear dorsal portion of the tip 3236. This results in a tip which has strength to prevent the tip folding over on itself and soft to prevent damage to the esophagus upon contact.

The tip 3232 of the laryngeal cuff 3218 is also provided with a series of annular flange sealing portions 3290. The annular flange sealing portions 3290 are provided for improved sealing of the tip 3232 of the laryngeal cuff 3218 in the upper esophagus region of the horse. The annular flange sealing portions are formed of a soft polymeric or other plastics material with a shore hardness of between 40 and 000 on the A scale. The annular flange sealing portion 3290 allows for better sealing with a more variable range of upper oesophageal features.

The airway device 3210 is also provided with a concave portion or scallop 3296 on the airway tube 3212. The concave portion or scallop 3296 is located on the opposite side of the airway tube 3212 to the raised portion 3238 around the location of the shoulder 3226. The concave portion of scallop 3296 is located at the back of the tongue of the horse in use. The concave portion or scallop 3296 acts to reduce the amount of pressure being applied to the convex portion of back of the tongue. When pressure is applied to the convex portion at the back of the tongue, this results in the formation of blue tongue in horses because the pressure to the tongue constricts blood vessels.

In addition for the airway device 3210 specifically designed for use in horses the airway device 3210 is further provided with an inflatable back cuff 3225 and inflation line 3227 to inflate the inflatable back cuff 3225. The inflatable back cuff 3225 is designed to lay flush with profile of the back dorsal portion 3220 of the laryngeal cuff 3218 when not inflated, and this does not interfere with the insertion of the device 3210. The inflatable back cuff 3225 is provided to give flexibility of fit of the device in different breeds of horse which may have much different sized architecture compared with rabbits to ensure a good seal across all breeds of horse.

Furthermore the airway device 3210 is provided with an oesophageal gastric channel 3280.

Furthermore the distal opening of the cuff 3218 is provided with a series of brackets 3211, 3213, 3215 to provide strength to the top 3232 of the device 3210 and to prevent downfolding of the horse epiglottis into the opening of the cuff 3221 and blocking the air flow.

The airway tube 3212 is designed in two portions 3229 and 3230 such that the device 3210 can be split into two portions to fit into standard sized autoclaves for sterilization between uses as the device 3210 for horses is much larger than that for other animals or humans. So that the oesophageal gastric channel 3280 and inflation line 3227 do not interfere with the disassembly of the device the oesophageal gastric channel 3210 and inflation line 3222 are housed within the first portion of the airway tube 3229 and removably fit into grooves 3233, 3235 provided in the second portion of the airway tube 3231. This means that when the device 3210 is disassembled the oesophageal gastric channel 3280 and the inflation line 3227 can simply be removed from their respective grooves 3233, 3235.

FIGS. 91 to 97 illustrate an embodiment of the airway device 3310 specifically designed for use with a dog. The airway device 3310 has an airway tube 3312 with a first end 3314 and a second end 3316. The first end 3314 of the airway tube 3312 is surrounded by a laryngeal cuff 3318. The cuff 3318 has a back dorsal portion 3320 and a front face portion 3322. The front face portion 3322 is shaped to form an anatomical fit over the laryngeal inlet of a dog. The second and 3316 of the airway tube is fitted with a connector 3324 such that the second end 3316 of the airway tube 3312 can be connected to the relevant gas supply. The airway device 3310 also has a shoulder 3326. The shoulder 3326 is used to prevent over-insertion of the airway device 3310. The shoulder 3326 is located laterally and substantially perpendicular to the direction of the airflow, and thus the airway tube 3312. The shoulder 3326 is located just above the neck 3328 of the airway device 3310 where the laryngeal cuff 3318 appears to join the airway tube 3312 at the second end 3314. The shoulder 3326 is used to create a point of contact between the airway device 3310 and the faucial pillars of the dog located at the back of the dogs mouth. This thus creates a positive stopping feature that in use prevents the shoulder portion 3326 going forward beyond the faucial pillars of the dog and thus prevents over-insertion of the airway device 3310.

In addition for the airway device 3310 specifically for use in dogs the shoulder 3326 is provided with forward facing protrusions 3393 located on the leading edge thereof. The forward facing protrusions 3393 are adapted to locate into anatomical cavities which are present in dogs, for example, after the pharyngeal arches. In general dogs have a very wide pharyngeal arch as they are designed to consume large volumes of food very rapidly. The forward facing protrusions 3393 being adapted to fit into the anatomical cavity region to make the whole airway device 3310 fit more securely and not easily by-pass the pharyngeal arches. It is worth bearing in mind that the pharyngeal arches are particularly elastic in dogs. Cavities 3395 are adapted to fit the thin protruding pharyngeal arches of the dog, without which the shoulders 3326 may be able to extend beyond.

The airway device 3310 is further provided with a raised portion 3338. The raised portion 3338 is located on the airway tube 3312 above and extending just behind the shoulder 3326 towards the second end 3316 of the airway tube when in situ in the dog, the raised portion 3338 corresponds to the location of the cavity of the upper mouth arch of the dog called the palatoglossal arch. The raised portion 3338 aids in preventing over-insertion of the airway device by being adapted to locate in the cavity of the palatoglossal arch due to the contouring of the raised portion and provides resistance on being moved beyond this position. The raised portion 3338 is not meant to be in constant contact with the palatoglossal arch but simply to locate into this cavity to prevent over-insertion and resist movement of the device when in situ.

The airway device 3310 is also further provided with a plurality of ribs 3360 near the second end 3316 of the airway tube 3312 near to the connector 3324. The ribs 3360 provide a friction point for tying the device around the dog's head as it is generally not possible to use tape as in humans due to the dog's fur.

In this embodiment the tip 3332 is a blade like tip 3397. The blade like tip 3397 is curved on the dorsal portion of the tip 3323 and planar on the front face portion of the tip 3351. The blade like tip 3397 is used to "flick" or peel the epiglottis of the dog downwards at the same time as the airway device 3310 is inserted in a single action.

The tip 3332 of the laryngeal cuff 3318 is also provided with a series of annular flange sealing portions 3390. The annular flange sealing portions 3390 are provided for improved sealing of the tip 3332 of the laryngeal cuff 3318 in the upper esophagus region of the dog. The annular flange sealing portions are formed of a soft polymeric or other plastics material with a shore hardness of between 40 and 000 on the A scale. The annular flange sealing portion 3390 allows for better sealing with a more variable range of upper oesophageal features.

The airway device 3310 is also provided with a concave portion or scallop 3396 on the airway tube 3312. The concave portion or scallop 3396 is located on the opposite side of the airway tube 3312 to the raised portion 3338 around the location of the shoulder 3326. The concave portion of scallop 3396 is located at the back of the tongue of the dog in use. The concave portion or scallop 3396 acts to reduce the amount of pressure being applied to the convex portion of back of the tongue. When pressure is applied to the convex portion at the back of the tongue, this results in the formation of blue tongue in dogs because the pressure to the tongue constricts blood vessels.

In addition for the airway device 3310 specifically designed for use in dogs the airway device 3310 is further provided with an inflatable back cuff 3325 and inflation line 3327 to inflate the inflatable back cuff 3325. The inflatable back cuff 3325 is designed to lay flush with profile of the back dorsal portion 3320 of the laryngeal cuff 3318 when not inflated, and this does not interfere with the insertion of the device 3310. The inflatable back cuff 3325 is provided to give flexibility of fit of the device in different breeds of dog which may have much different sized architecture compared with rabbits to ensure a good seal across all breeds of dog.

Furthermore the airway device 3310 is provided with an oesophageal gastric channel 3380.

Furthermore the distal opening of the cuff 3318 is provided with a bracket 3311 to provide strength to the tip 3332 of the device 3310 and to prevent downfolding of the large dog epiglottis into the opening of the cuff 3321 and blocking the air flow.

Again it should be made clear that the features which are described above which include but are not limited to the shoulder, the raised portion, the angled tip of the laryngeal cuff, the annular flanges around the tip of the laryngeal cuff, the ribs on the airway tube, the mesh, the perforated plate, the skeleton formation, the brackets, the inflatable back cuff, the portional hard plastics material, the blade like tip and the scallop or concave portion can all be used individually from each other in separate embodiments of the invention and that some features are shown and described in combination with other features is not intended to be limiting and it is intended that each feature can be used independently from any of the other features and also in combination with any or all of the other features described herein including but not limited to those listed above.

The invention claimed is:

1. An airway device for human or animal use, the device comprises an airway tube having a first end and a second end, wherein the device has a horizontal plane, wherein the device further comprises a shoulder portion, the shoulder portion extending laterally from the airway tube, the shoulder portion having a substantially planar leading face extending 90°±15° relative to the airway tube horizontal plane, which is adapted to contact the faucial pillars of the human or animal patient upon insertion to create a positive stop to prevent the shoulder portion of the device moving beyond the faucial pillars of the human or animal patient in use, the horizontal plane going through the leading face extending from the first end to the second end of the tube, and further wherein the leading face is angled vertically to the horizontal plane, whereupon after impacting the faucial pillars upon insertion, the shoulder portion will bounce back and come to rest without being in direct contact with the faucial pillars of the human or animal.

2. The airway device as claimed in claim 1, wherein the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal against the laryngeal inlet of the patient.

3. The airway device as claimed in claim 1, for insertion into the trachea or bronchi of a human or animal patient comprising a cuff located at or near the first end of the airway tube, wherein the cuff is adapted to engage the wall of the trachea or bronchi in use.

4. The airway device as claimed in claim 1, wherein the shoulder portion includes a harder interval portion and a soft external covering.

5. The airway device as claimed in claim 1, wherein the leading face is provided with a forward facing protrusion.

6. The airway device as claimed in claim 1, wherein the leading face is provided with a forward facing indentation or cavity.

7. The airway device as claimed in claim 1, wherein the shoulder portion is provided with a suction channel.

8. The airway device as claimed in claim 1, wherein he airway tube has a back dorsal portion, and wherein the back dorsal portion includes a raised portion.

9. The airway device as claimed in claim 8, wherein the raised portion is adapted to fill the cavity of the palatoglossal arch of the human or animal patient in use.

10. The airway device as claimed in claim 8, wherein the raised portion includes a harder internal portion and a soft external covering.

11. The airway device as claimed in claim 9, wherein the raised portion includes a harder internal portion and a soft external covering.

12. The airway device as claimed in claim 2, wherein the laryngeal cuff has a tip portion.

13. The airway device as claimed in claim 12, wherein the laryngeal cuff has a back dorsal portion, and wherein the tip portion is angled towards the heck dorsal portion of the laryngeal cuff.

14. The airway device as claimed in claim 13, wherein the tip portion is angled between and including 5° to 80° from the horizontal plane.

15. The airway device as claimed in claim 12, wherein the tip portion has a back dorsal portion and a front face portion, the back dorsal portion being formed from a harder material than the front face portion.

16. The airway device as claimed in claim 14, wherein the tip portion has a back dorsal portion and a front face portion, the hack dorsal portion being formed from a harder material than the front face portion.

17. The airway device as claimed in claim 12, wherein the tip portion includes an annular flange sealing portion.

18. The airway device as claimed in claim 17, wherein the annular flange sealing portion is adapted to wedge into upper esophagus region of the human or animal patient.

19. The airway device as claimed in claim 12, wherein the tip portion is blade shaped.

20. The airway device as claimed in claim 17, wherein the tip portion has a back dorsal portion which is contoured and a front face portion which is substantially planar.

21. The airway device as claimed in claim 1, wherein the airway tube is provided with at least one concave portion.

22. The airway device as claimed in claim 21, wherein the at least one concave portion is in use adapted to contact the convex portion of the back of the tongue of the human or animal patient.

23. The airway device as claimed in claim 21, wherein the at least one concave portion is a plurality of concave portions.

24. The airway device as claimed in claim 23, wherein the plurality of concave portions are formed from protrusions.

25. The airway device as claimed in claim 23, wherein the plurality of concave portions are formed from depressions.

26. The airway device as claimed in claim 22, wherein the at least one concave portion is a plurality of concave portions.

27. The airway device as claimed in claim 26, wherein the plurality of concave portions are formed from protrusions.

28. The airway device as claimed in claim 26, wherein the plurality of concave portions are formed from depressions.

29. The airway device as claimed in claim 2, wherein the laryngeal cuff has an opening in fluid communication with the airway tube and wherein the opening is provided with a bracket.

30. The airway device as claimed in claim 29, wherein the bracket extends from the distal end of the opening.

31. The airway device as claimed in claim 29, wherein the bracket extends from the proximal end of the opening.

32. The airway device as claimed in claim 29, wherein the bracket extends the full length of the opening.

33. The airway device as claimed in claim 29, wherein the bracket is provided with notches or grooves in its front face surface.

34. The airway device as claimed in claim 2, further comprising inflatable cuff located on the back dorsal portion of the laryngeal cuff.

35. The airway device as claimed in claim 34, wherein the inflatable cuff has a defined perimeter.

36. The airway device as claimed in claim 34, wherein the inflatable cuff is formed from a soft material of Shore Hardness on the A scale of 20 or less.

37. The airway device as claimed in claim 34, wherein the inflatable cuff is formed from a soft material of Shore Hardness on the A scale of 20 or less.

38. The airway device as claimed in claim 34, wherein when deflated the inflatable cuff is substantially flush with the back dorsal portion of the laryngeal cuff.

* * * * *